(12) United States Patent
Granot et al.

(10) Patent No.: US 9,199,028 B2
(45) Date of Patent: Dec. 1, 2015

(54) USE OF ENTRAINED NEUTROPHILS TO TREAT METASTATIC AND MICROMETASTATIC DISEASE IN AT RISK PATIENTS

(75) Inventors: Zvi Granot, New York, NY (US); Robert Benezra, Hampton Bays, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 601 days.

(21) Appl. No.: 13/521,982

(22) PCT Filed: Jan. 14, 2011

(86) PCT No.: PCT/US2011/021408
§ 371 (c)(1),
(2), (4) Date: Nov. 1, 2012

(87) PCT Pub. No.: WO2011/088402
PCT Pub. Date: Jul. 21, 2011

(65) Prior Publication Data
US 2013/0072844 A1    Mar. 21, 2013

Related U.S. Application Data

(60) Provisional application No. 61/336,044, filed on Jan. 15, 2010.

(51) Int. Cl.
| | | |
|---|---|---|
| *C12N 5/0787* | (2010.01) | |
| *A61K 35/15* | (2015.01) | |
| *A61M 1/36* | (2006.01) | |
| *A61K 38/19* | (2006.01) | |
| *C12N 5/07* | (2010.01) | |
| *A61K 35/12* | (2015.01) | |

(52) U.S. Cl.
CPC .......... *A61M 1/3687* (2013.01); *A61K 38/193* (2013.01); *C12N 5/06* (2013.01); *C12N 5/0642* (2013.01); *A61K 2035/124* (2013.01); *C12N 2501/21* (2013.01)

(58) Field of Classification Search
CPC ............... A61K 2035/124; A61K 2300/00; C12N 5/0642; C12N 2501/21
See application file for complete search history.

(56) References Cited

U.S. PATENT DOCUMENTS

| 5,179,078 A | 1/1993 | Rollins et al. ........... 514/19.2 |
| 5,714,578 A | 2/1998 | Yoshimura et al. ........ 530/324 |
| 5,770,402 A * | 6/1998 | Beutler et al. ............ 435/69.5 |

OTHER PUBLICATIONS

Bozic et al., Journal of Immunology Jun. 1, 1995 vol. 154 No. 11 6048-6057.*
Wengner et al., Blood. Jan. 1, 2008; 111(1): 42-49.*
Cohn, in *The Baltimore Sun*, p. 2 of 5 (2010).
Colombo, et al., "Granulocyte colony-stimulating factor (G-CSF) gene transduction in murine adenocarcinoma drives neutrophil-mediated tumor inhibition in vivo. Neutrophils discriminate between G-CSF-producing and G-CSF-nonproducing tumor cells." *J Immunol*, 149:113-119 (1992).
Combadiere, et al., "Cloning and Functional Expression of CC CKR5, a Human Monocyte CC Chemokine Receptor Selective for MIP-1(Alpha), MIP-1(Beta), and Rantes." *J Leukoc Biol*, 60(1):147-152 (1996).
De Larco, et al., "The Potential Role of Neutrophils in Promoting the Metastatic Phenotype of Tumors Releasing Interleukin-8." *Clin Cancer Res*, 10(15):4895-4900 (2004).
Dehqanzada, et al., "Correlations between Serum Monocyte Chemotactic Protein-1 Levels, Clinical Prognostic Factors, and Her-2/Neu Vaccine-Related Immunity in Breast Cancer Patients." *Clin Cancer Res*, 12(2):478-486 (2006).
DuPre and Hunter, "Murine Mammary Carcinoma 4T1 Induces a Leukemoid Reaction with Splenomegaly: Association with Tumor-Derived Growth Factors." *Exp Mol Pathol*, 82(1):12-24 (2007a).
DuPre, et al., "The Mouse Mammary Carcinoma 4T1: Characterization of the Cellular Landscape of Primary Tumours and Metastatic Tumour Foci." *Int J Exp Pathol*, 88(5):351-360 (2007b).
Erler, et al., "Hypoxia-Induced Lysyl Oxidase is a Critical Mediator of Bone Marrow Cell Recruitment to Form the Premetastatic Niche." *Cancer Cell*, 15(1):35-44 (2009).
Fridlender, et al., "Polarization of Tumor-Associated Neutrophil Phenotype by TGF-Beta: "N1" Versus "N2" Tan." *Cancer Cell*, 16(3):183-194 (2009).
Gu, et al., "Monocyte Chemoattractant Protein-1." *Chem Immunol*, 72:7-29 (1999).
Gupta and Massague, "Cancer Metastasis: Building a Framework." *Cell*, 127(4):679-695 (2006).
Hicks, et al., "Transferable Anticancer Innate Immunity in Spontaneous Regression/Complete Resistance Mice." *Proc Natl Acad Sci USA*, 103(20):7753-7758 (2006).
Hiratsuka, et al., " MMP9 Induction by Vascular Endothelial Growth Factor Receptor-1 is Involved in Lung-Specific Metastasis." *Cancer Cell*, 2(4):289-300 (2002).
Hiratsuka, et al., "Tumour-Mediated Upregulation of Chemoattractants and Recruitment of Myeloid Cells Predetermines Lung Metastasis." *Nat Cell Biol*, 8(12):1369-1375 (2006).
Huang, et al., "Expression of the JE/MCP-1 Gene Suppresses Metastatic Potential in Murine Colon Carcinoma Cells." *Cancer Immunol Immunother*, 39(4):231-238 (1994).

(Continued)

*Primary Examiner* — Daniel C Gamett
(74) *Attorney, Agent, or Firm* — Medlen & Carroll, LLP

(57) ABSTRACT

The present invention relates generally to compositions and methods for treating cancer patients with a poor prognosis, and to therapeutic modalities for improving prognosis by combating metastasis and abrogating chemoresistance in cancer cells. In particular, the invention relates to the role of white blood cells, i.e. neutrophils and neutrophil-like cells, in preventing the spread of cancer from a primary tumor to secondary locations in the body. The invention provides methods for reducing or delaying the spread of metastatic cancer cells in a patient at risk for metastatic tumor development, at risk for metastatic relapse, i.e. prophylactic methods, and treating patients suffering from metastatic tumors.

20 Claims, 14 Drawing Sheets

(56) References Cited

OTHER PUBLICATIONS

Ishino, et al., "Risk Stratification of Chronic Heart Failure Patients by Multiple Biomarkers: Implications of BNP, H-FABP, and PTX3." *Circ J*, 72(11):1800-1805 (2008).
Itoh, et al., "Experimental Metastasis is Suppressed in MMP-9-Deficient Mice." *Clin Exp Metastasis*, 17(2):177-181 (1999).
Joyce and Pollard, "Microenvironmental Regulation of Metastasis." *Nat Rev Cancer*, 9(4):239-252 (2009).
Kaplan, et al., "VEGFR1-Positive Haematopoietic Bone Marrow Progenitors Initiate the Pre-Metastatic Niche." *Nature*, 438(7069):820-827 (2005).
Kjeldsen, et al., "Subcellular Fractionation of Human Neutrophils on Percoll Density Gradients." *J Immunol Methods*, 232(1-2):131-143 (1999).
Loberg, et al., "Targeting CCL2 with Systemic Delivery of Neutralizing Antibodies Induces Prostate Cancer Tumor Regression in Vivo." *Cancer Res*, 67(19):9417-9424 (2007).
Lu and Kang, "Chemokine (C-C Motif) Ligand 2 Engages CCR2+ Stromal Cells of Monocytic Origin to Promote Breast Cancer Metastasis to Lung and Bone." *J Biol Chem*, 284(42):29087-29096 (2009).
Minn, et al., "Genes That Mediate Breast Cancer Metastasis to Lung." *Nature*, 436(7050):518-524 (2005).
Monti, et al., "The CC Chemokine MCP-1/CCL2 in Pancreatic Cancer Progression: Regulation of Expression and Potential Mechanisms of Antimalignant Activity." *Cancer Res*, 63(21):7451-7461 (2003).
Neote, et al., "Molecular Cloning, Functional Expression, and Signaling Characteristics of a C-C Chemokine Receptor." *Cell*, 72(3):415-425 (1993).
Nozawa, et al., "Infiltrating Neutrophils Mediate the Initial Angiogenic Switch in a Mouse Model of Multistage Carcinogenesis." *Proc Natl Acad Sci U S A*, 103(33):12493-12498 (2006).
Payne and Cornelius, "The Role of Chemokines in Melanoma Tumor Growth and Metastasis." *J Invest Dermatol*, 118(6):915-922 (2002).
Pekarek, et al., "Inhibition of Tumor Growth by Elimination of Granulocytes." *J Exp Med*, 181(1):435-440 (1995).
Ponath, et al., "Molecular Cloning and Characterization of a Human Eotaxin Receptor Expressed Selectively on Eosinophils." *J Exp Med*, 183(6):2437-2448 (1996).
Power, et al., "Molecular Cloning and Functional Expression of a Novel CC Chemokine Receptor cDNA from a Human Basophilic Cell Line." *J Biol Chem*, 270(33):19495-19500 (1995).
Reichel, et al., "Chemokine Receptors Ccr1, Ccr2, and CcrS Mediate Neutrophil Migration to Postischemic Tissue." *J Leukoc Biol*, 79(1):114-122 (2006).
Schmielau and Finn, "Activated Granulocytes and Granulocyte-Derived Hydrogen Peroxide are the Underlying Mechanism of Suppression of T-Cell Function in Advanced Cancer Patients." *Cancer Res*, 61(12):4756-4760 (2001).
Shojaei, et al., "Bv8 Regulates Myeloid-Cell-Dependent Tumour Angiogenesis." *Nature*, 450(7171):825-831 (2007).
Shojaei, et al., "Role of Bv8 in Neutrophil-Dependent Angiogenesis in a Transgenic Model of Cancer Progression." *Proc Natl Acad Sci U S A*, 105(7):2640-2645 (2008).
Singh, et al., "A Simple Activity Staining Protocol for Lipases and Esterases." *Appl Microbiol Biotechnol*, 70(6):679-682 (2006).
Soria and Ben-Baruch, "The Inflammatory Chemokines CCL2 and CCL5 in Breast Cancer." *Cancer Lett*, 267(2):271-285 (2008).
Takahashi, et al., "Chemokine CCL2/MCP-1 Negatively Regulates Metastasis in a Highly Bone Marrow-Metastatic Mouse Breast Cancer Model." *Clin Exp Metastasis*, 26(7):817-828 (2009).
Tonouchi, et al., "Profile of Monocyte Chemoattractant Protein-1 Circulating Levels in Gastric Cancer Patients." *Scand J Gastroenterol*, 37(7):830-833 (2002).
Watanabe, et al., "Decreased Expression of Monocyte Chemoattractant Protein-1 Predicts Poor Prognosis Following Curative Resection of Colorectal Cancer." *Dis Colon Rectum*, 51(12):1800-1805 (2008).
Yan, et al., "Gr-1+CD11b+ Myeloid Cells Tip the Balance of Immune Protection to Tumor Promotion in the Premetastatic Lung." *Cancer Res*, 70(15):6139-6149 (2010).
Yang, et al., "Abrogation of TGF Beta Signaling in Mammary Carcinomas Recruits Gr-1+CD11b+ Myeloid Cells That Promote Metastasis." *Cancer Cell*, 13(1):23-35 (2008).
Youn, et al., "Subsets of Myeloid-Derived Suppressor Cells in Tumor-Bearing Mice." *J Immunol*, 181(8):5791-5802 (2008).
Zhang, et al., "Expression of a Soluble TGF-Beta Receptor by Tumor Cells Enhances Dendritic Cell/Tumor Fusion Vaccine Efficacy." *J Immunol*, 181(5):3690-3697 (2008).
Brown, et al., "Tumor-Derived Chemokine MCP-1/CCL2 is Sufficient for Mediating Tumor Tropism of Adoptively Transferred T Cells." *J Immunol*, 179(5):3332-3341 (2007).
Challacombe, et al., "Neutrophils are a Key Component of the Antitumor Efficacy of Topical Chemotherapy with Ingenol-3-Angelate." *J Immunol*, 177(11):8123-8132 (2006).
Craig and Loberg, "CCL2 (Monocyte Chemoattractant Protein-1) in Cancer Bone Metastases." *Cancer Metastasis Rev*, 25(4):611-619 (2006).
Harding, et al., "Complete Correction of Hyperphenylalaninemia Following Liver-Directed, Recombinant Aav2/8 Vector-Mediated Gene Therapy in Murine Phenylketonuria." *Gene Ther*, 13(5):457-462 (2006).
Hu, et al., "Recombined CC Chemokine Ligand 2 into B16 Cells Induces Production of Th2-Dominant [Correction of Dominanted] Cytokines and Inhibits Melanoma Metastasis." *Immunol Lett*, 113(1):19-28 (2007).
Lebrecht, et al., "Monocyte Chemoattractant Protein-1 Serum Levels in Patients with Breast Cancer." *Tumour Biol*, 25(1-2):14-17 (2004).
Li, et al., "A Destructive Cascade Mediated by CCL2 Facilitates Prostate Cancer Growth in Bone." *Cancer Res*, 69(4):1685-1692 (2009).
Nam, et al., "Chemokine (C-C Motif) Ligand 2 Mediates the Prometastatic Effect of Dysadherin in Human Breast Cancer Cells." *Cancer Res*, 66(14):7176-7184 (2006).
Tanaka, et al., "The Expression of Monocyte Chemotactic Protein-1 in Papillary Thyroid Carcinoma is Correlated with Lymph Node Metastasis and Tumor Recurrence." *Thyroid*, 19(1):21-25 (2009).
Tsuchiyama, et al., "Prolonged, NK Cell-Mediated Antitumor Effects of Suicide Gene Therapy Combined with Monocyte Chemoattractant Protein-1 against Hepatocellular Carcinoma." *J Immunol*, 178(1):574-583 (2007).
Zhang, et al., "Migration of Cytotoxic T Lymphocytes toward Melanoma Cells in Three-Dimensional Organotypic Culture is Dependent on CCL2 and CCR4." *Eur J Immunol*, 36(2):457-467 (2006).

\* cited by examiner

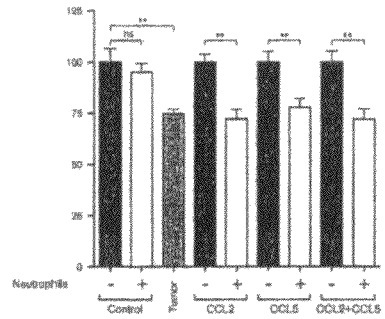
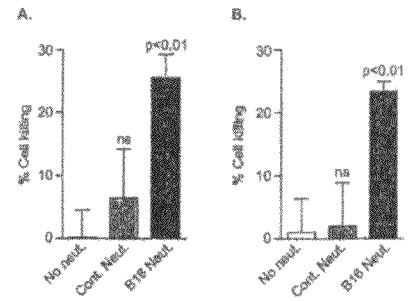
Figure 15    Figure 16
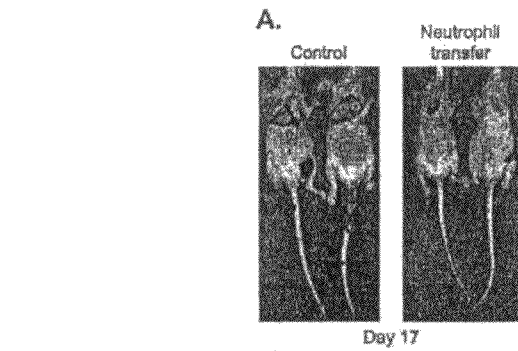
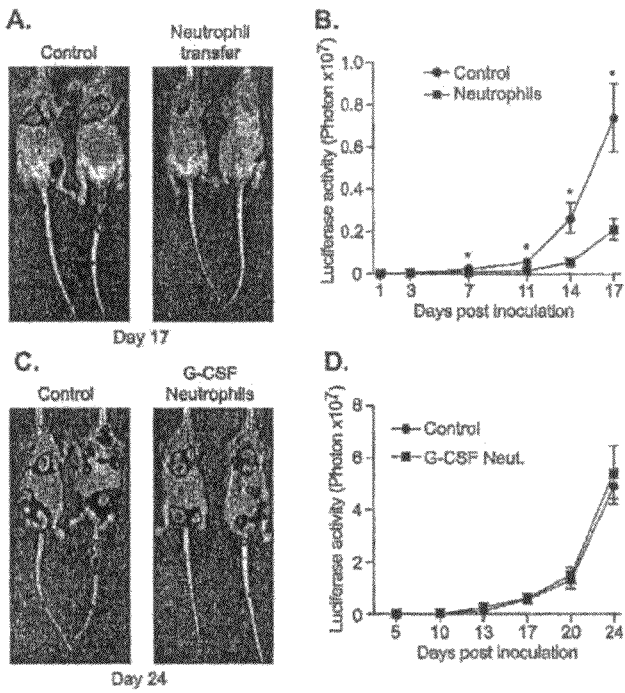
Figure 17    Figure 18
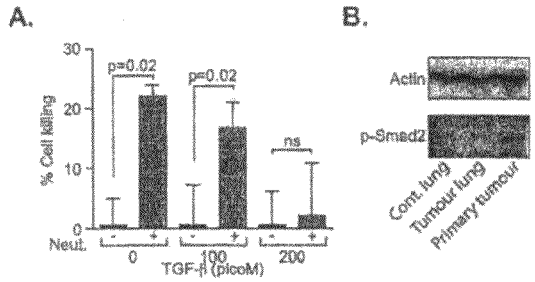
Figure 19

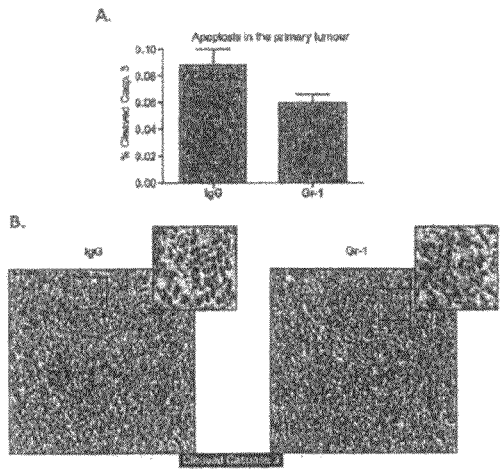
Figure 24
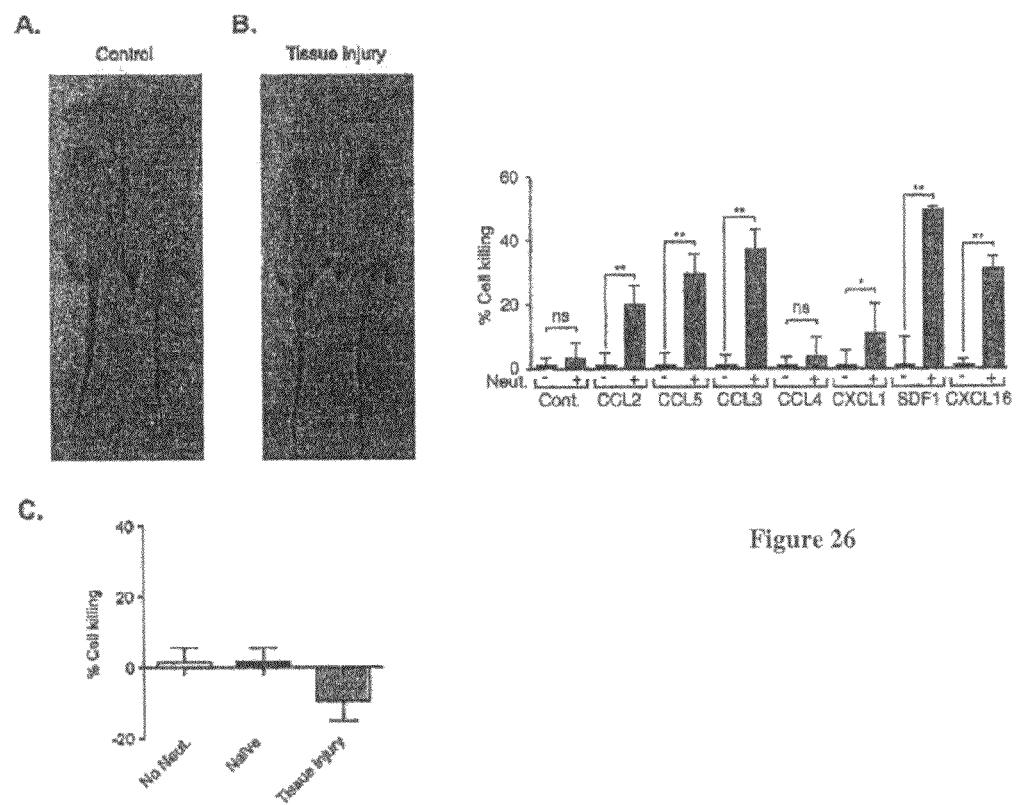
Figure 25
Figure 26

USE OF ENTRAINED NEUTROPHILS TO TREAT METASTATIC AND MICROMETASTATIC DISEASE IN AT RISK PATIENTS

FIELD OF THE INVENTION

The present invention relates generally to compositions and methods for treating cancer patients with a poor prognosis, and to therapeutic modalities for improving prognosis by combating metastasis and abrogating chemoresistance in cancer cells. In particular, the invention relates to the role of subset white blood cells, i.e. neutrophils and neutrophil-like cells, in preventing the spread of cancer from a primary tumor to secondary locations in the body. The invention provides methods for reducing or delaying the spread of metastatic cancer cells in a patient at risk for metastatic tumor development, at risk for metastatic relapse, i.e. prophylactic methods, and treating patients suffering from metastatic tumors.

BACKGROUND

The leading cause of cancer related mortality is metastatic spread of tumor cells to distant sites and the location of these sites varies considerably among different primary tumor types. Although there has been much investigation into the metastatic process, the multiple factors which drive progression of metastasis have not been fully elucidated.

The progression of cancer from an abnormal outgrowth to a life-threatening metastatic tumor is accompanied by a myriad of genetic and epigenetic alterations accumulated along the way. Multiple factors secreted by the primary tumor have been shown to have an impact on the formation of the pre-metastatic niche. However the full range of activities that such secreted factors can have on the pre-metastatic niche is unknown.

The importance of the interplay between the primary tumor site and modulation of the pre-metastatic niche has recently come to light as one such driving force of metastasis.

However the challenge of distinguishing crucial drivers of metastasis from thousands of by-stander alterations remains a major obstacle in the battle against cancer.

Therefore, there is a need for identifying factors that impact formation of the pre-metastatic niche in order to develop treatments to stop development of metastatic tumors.

SUMMARY OF THE INVENTION

The present invention relates generally to compositions and methods for treating cancer patients with a poor prognosis, and to therapeutic modalities for improving prognosis by combating metastasis and abrogating chemoresistance in cancer cells. In particular, the invention relates to the role of white blood cells, i.e. neutrophils and neutrophil-like cells, in preventing the spread of cancer from a primary tumor to secondary locations in the body. The invention provides methods for inhibiting metastasis in a patient at risk for metastatic tumor development, at risk for metastatic relapse, i.e. prophylactic methods, and treating patients suffering from metatastic tumors.

An object of the present invention is a method to treat metastatic and/or micrometastic disease in a cancer patient who is at risk for metastatic relapse and/or is suffering from metastatic disease.

In one embodiment, neutrophils are isolated, expanded ex vivo, and entrained with chemokines. Following treatment of the primary tumor by any standard level of care for any cancer, these entrained neutrophils ("TENs") are reintroduced into the patient. The TENs will home to any metastatic sites and kill and/or prevent metastases and/or micrometastases; thus conferring anti-metastatic protection. Another object of the present invention is a method to produce TENs suitable to confer anti-metastatic protection. Another object of the present invention is the identification of potential therapeutic targets for disrupting the pre-metastatic niche as a second method to treat metastatic disease.

The present inventions provide a method, comprising, a) providing, i) a patient at risk for a tumor, wherein said patient comprises a neutrophil, wherein said neutrophil is capable of being cytotoxic to a tumor cell; and ii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing said neutrophil cytotoxicity; b) isolating said neutrophil from said patient; and c) contacting said neutrophil with said chemokine under conditions for increasing cytotoxic activity of said neutrophil. In one embodiment, said contacting further comprises contacting with an agent for increasing cytotoxicity of a neutrophil. In one embodiment, said contacting further comprises contacting with a transforming growth factor-beta inhibitor. In one embodiment, the method further comprises a test tumor cell, wherein said neutrophil has increased cytotoxicity towards said test tumor cell after said contacting. It is not meant to limit the test tumor cell, indded, a variety of test tumor cell are contemplated including but not limited to a cancer cell of a cell line, a cancer cell isolated from a patient, a tumor cell isolated from a patient, etc. In one embodiment, said increasing cytotoxicity is increasing cytotoxicty for mediating killing of a tumor cell. In one embodiment, said increasing cytotoxicity is increasing capability to induce apoptosis in a tumor cell. In one embodiment, said increasing cytotoxicity is increasing oxidative activity of said neutrophil for providing an oxidative burst capable of killing a tumor cell. In one embodiment, said patient is administered granulocyte colony-stimulating factor prior to said isolation of said neutrophil. In one embodiment, said neutrophil comprises a matrix metallopeptidase 9 marker.

The present inventions provide a method, comprising, a) providing, i) a patient comprising at least one tumor cell capable of metastasis, wherein said patient further comprises a neutrophil, wherein said neutrophil is capable of being cytotoxic to said tumor cell; ii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing, cytotoxicity of said neutrophil; b) isolating said neutrophil from said patient; c) contacting said neutrophil with said chemokine under conditions for increasing cytotoxic activity of said neutrophil; and d) administering said contacted neutrophil to said patient under conditions such that said tumor cell is inhibited from metastasis. In one embodiment, said contacting further comprises contacting with a transforming growth factor-beta inhibitor. In one embodiment, said tumor cell is selected from the group consisting of breast cancer, colon cancer, prostate cancer and lung cancer. In one embodiment, said neutrophil comprises a matrix metallopeptidase 9 marker. In one embodiment, said increasing cytotoxicity is increasing cytotoxicty for mediating killing of a tumor cell. In one embodiment, said increasing cytotoxicity is increasing capability to induce apoptosis in a tumor cell. In one embodiment, said increasing cytotoxicity is increasing oxidative activity of said neutrophil for providing an oxidative burst capable of killing a tumor cell. In one embodiment, said method further comprises administering a granulocyte colony-stimulating factor to said patient prior to said isolation of said neutrophil. In one embodiment, said administering of said neutrophil is prior to detection of said tumor cell metastasis. In one embodiment, said administering, of said neutrophil is after detection of said metastasis.

The present inventions provide a method, comprising, a) providing, i) a pharmaceutical composition, comprising an agent for increasing the number of neutrophils in a blood sample; ii) a patient comprising a tumor cell and circulating neutrophils; iii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing cytotoxicity of a neutrophil; b) administering said pharmaceutical composition under conditions such that said circulating neutrophils are increased in a blood sample of said patient; c) isolating said neutrophils from a blood sample of said patient; d) contacting said a neutrophils with said chemokine under conditions for increasing cytotoxic activity of said neutrophil; and e) administering said contacted neutrophils to said patient under conditions such that said tumor cell is inhibited from metastasis. In one embodiment, said agent is granulocyte colony-stimulating factor.

DEFINITIONS

To facilitate the understanding of this invention a number of terms (set off in quotation marks in this Definitions section) are defined below.

The terms "patient" and "subject" refer to a mammal (human and animal, i.e. non-human animals) which is to be the recipient of a particular treatment including any type of control. Typically, the terms "subject" and "patient" are used interchangeably herein in reference to a human subject.

A "reference subject" herein refers to an individual who does not have cancer, and is used interchangeably with "healthy subject." The "reference subject" thereby provides a basis to which another cell (for example a cancer cell) can be compared.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "cancer" and a number of terms relating to cancer is intended herein to encompass all forms of abnormal or improperly regulated growth of cells in a subject.

As used herein, the term "growth" refers generally to cell division and also to the growth in size of masses of cells, i.e. tumor growth. The growth of cancer cells is characteristically uncontrolled or inadequately controlled, such as when normal death "apoptosis" of such cells does not occur. Local accumulations of such cells result in a tumor.

The term "tumor" or "tumour" or "neoplasm" relates to any tissue that grew abnormally or is growing abnormally because of uncontrolled or inadequately controlled, progressive multiplication of cells, i.e. cancer cells. The tumor or neoplasm may be benign if it no longer has properties of cancer, that is, its growth is self-limited and its cells do not invade adjacent tissues or "metastasize" to distant tissues. Tumors that grow sufficiently so as to encroach upon or invade adjacent tissues or that split off metastatic cells are said to be "malignant."

The term "malignant" in relation to a tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel walls; "intravasate" relates to entering and "extravasate" relates to exiting blood vessels. Tumors capable of releasing such cells are also referred to herein as "metastatic." The term is used herein also to denote any cell in such a tumor cell that is capable of such travel, or that is en route, or that has established a foothold in a target tissue. For example, a metastatic breast cancer cell that attaches in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein.

A "tumor cell" or "TC" refers to a cancer cell derived from a tumor. The cell may be endogenous or exogenous. The cell may be split off from or harvested from a primary tumor or a secondary tumor; the cell may be a metastatic cancer cell or a metastasized cancer cell. The tumor of origin may be associated with any internal organ, including but not limited to colorectum, gastrointestinal tract and associated organs such as liver, pancreas and esophagus, ovary, uterus, prostate, lung, trachea kidney, bladder breast, brain and organs of the head and neck. A "circulating tumor cell" or "CTC" is a turner cell actually circulating in the bloodstream, the lymphatic system or in other fluids such as peritoneal or cerebrospinal fluids.

As used herein, the term "subject at risk for cancer" or "patient at risk for a tumor" refers to a subject with one or more risk factors for developing a specific cancer cell that may or may not give rise to a tumor. Risk factors include, but are not limited to, gender, age, genetic predisposition, environmental exposure, previous incidents of cancer, preexisting non-cancer diseases, lifestyle, a biomarker signature associated with cancer cell development, a biomarker signature associated with tumor development, and the like.

As used herein, the term "subject at risk for metastatic cancer" refers to patients diagnosed with invasive disease which causes them to be at high risk of developing a metastatic disease, such patients are contemplated to benefit from administration of their own TENs. A patient may be considered at risk with a biomarker signature that prognoses increased risk for metastasis. A patient may be considered at risk after being diagnosed with a large tumor and lymph node involvement. In addition, patients with triple negative breast cancer may be considered at high risk.

As used herein, the term "identifying the risk of said tumor metastasizing" refers to the relative risk (e.g., the percent chance or a relative score) of a tumor (e.g., prostate tumor tissue) metastasizing.

As used herein, the term "identifying the risk of said tumor recurring" refers to the relative risk (e.g., the percent chance or a relative score) of a tumor (e.g., prostate tumor tissue) recurring in the same organ as the original tumor (e.g., prostate).

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass in breast tissue or increased PSA level for prostrate cancer) but for whom a confirmatory test (e.g., biopsy and/or histology) has not been done or for whom the stage of cancer is not known. The term further includes subjects who once had cancer (e.g., an individual in remission).

A "subject suspected of having cancer" is sometimes diagnosed with cancer and is sometimes found to not have cancer.

As used herein, the term "subject diagnosed with a cancer" or "patient with cancer" refers to a subject who has been tested and found to have cancerous cells. The cancer may be diagnosed using any suitable method, including but not limited to, biopsy, x-ray, blood test, and diagnostic methods suitable for specific types of cancer. One example of a patient with cancer is a human patient with breast cancer.

As used herein, the term "initial diagnosis" refers to a test result of initial cancer diagnosis that reveals the presence or absence of cancerous cells (e.g., using a biopsy and histology). An initial diagnosis may not include information about the stage of the cancer or the risk of metastatic cancer.

A "sample" refers to a specimen taken from any one of a normal subject, a diagnosed subject or an undiagnosed subject. A "diagnosed subject" relates to a subject known to have a cancer or tumor of interest. An "undiagnosed subject" may be healthy or may have a cancer. A "diagnosed subject sample" refers to a sample containing at least one cell suspended in a fluid such as blood, lymph or ascites, or saline, etc., which cell is a cancer cell of the type of cancer for which the diagnosed subject has been diagnosed. An "undiagnosed subject's sample" is the same except that, by definition, the cell therein can only be suspected of being a cancer cell. A "normal subject sample" does not contain a cancer cell. A sample is characterized herein not only by the subject's diagnosis but also by the site from which the sample is collected. Thus, in a subject diagnosed with ovarian cancer, for example, a sample comprising cells derived from a biopsy of the tumor, a sample comprising cells in ascites fluid drawn from the subject, and a sample obtained from a biopsy of a lymph node of the subject may be treated as different inasmuch as the cancer cell in each sample type may have its own gene expression signature.

A "gene expression signature" or "biomarkers" includes but is not limited to gene expression profiles as generally understood in the art. As used herein, however, a gene expression profile generally requires "editing" to become a gene expression "signature." For example, a gene expression profile of circulating tumor cells in patients with late-stage colon cancer contained about 1200 genes differentially expressed in comparison to normal cells, whereas the gene signature ultimately derived therefrom comprised 24 genes only, because genes not known to be upregulated in cells of epithelial lineage or in metastatic tumors were "edited out" as were some redundant upregulations and downregulations. A gene expression signature is referred to as an "initial signature" when less than all editing steps have been applied to the gene expression profile. In some contexts, reference is made to a "refined signature" simply to distinguish between two steps in the editing process. Thus, an "initial signature" may be refined by removing from it, for example, one or more genes not known to be upregulated in metastatic tumor cells, and further refined by removing one or more genes not known to be associated with cells of epithelial lineage. A signature that contains all the genes that survive editing is referred to herein as an "optimal signature," but less than all of the genes in an optimal signature may nevertheless constitute an "effective signature" herein. A gene that appears in a signature, whether by upregulation, downregulation, or otherwise, is said to be a "constituent" of the signature. For example, the constituent genes for an optimum signature for gene expression at a metastatic niche are described herein, for example, 325 and 912 genes was significantly changed in the lung and liver (respectively) of tumour-bearing mice 7 days after tumour engraftment, and listed in FIG. 1.

A "normal cell sample" or "NC" relates, without limitation, to a sample of blood, a blood fraction such as a leukocyte, epithelial cell, endothelial cell or hematopoietic progenitor cell fraction, another body fluid comprising cells, or a suspension of cells extracted from a tissue or organ such as breast, lung, intestine, ovary, etc., provided only that such sample is collected from a donor considered healthy by conventional standards Primary tumors are thought to derive from a benign or normal cell through a process referred to herein as "cancer progression." According to this view, the transformation of a normal cell to a cancer cell requires changes (usually many of them) in the cell's biochemistry. The changes are reflected clinically as the disease progresses through stages. Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain "genomic gain" or lose "genomic loss" genes, typically because an extra copy of an entire chromosome appears "trisomy" or a region of a chromosome replicates itself "genomic gain" or, in some cases, "genomic amplification") or drops out when the cell divides. Thus, the "copy number" of a gene or a set of genes, largely invariant among normal cells, is likely to change in cancer cells, referred to herein as a "genomic event", which affects the total expression of the gene or gene set and the biological behavior "phenotype" of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes That govern the inheritance of genes in successive generations of cells or individuals.

It is thought that the emergence of metastatic cells entails its own distinct progression, referred to herein as "metastatic progression." The effect of disrupting a tumor on metastatic progression is unclear, but of interest because of "metastatic seeding," herein meaning a "surge" in metastasis that occurs, for example, when a tumor is surgically resected.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, "metastatic cancer" relates to when a cancer spreads (metastasizes) from its original site to another area of the body. Virtually all cancers have the potential to spread this way. Whether metastases develop depends on the complex interaction of many tumor cell factors, including the type of cancer, the degree of maturity (differentiation) of the tumor cells, the location and how long the cancer has been present, as well as other incompletely understood factors.

As used herein, the term "metastasis" refers to formation of progressively growing secondary tumor foci at sites discontinuous from the primary lesion. The metastatic process is a multi-step mechanism in which a metastatic cancer cell escapes from the primary tumor, enters the circulation, invades a distant tissue site and grows into a macroscopic tumor at the target site.

As used herein, "at risk" or "at risk for developing a tumor" in reference to a patient refers generally to a patient in a group including but not limited to "at risk for developing metastatic cancer," "at risk for metastatic relapse," "at risk for developing a primary tumor," and the like.

As used herein, a patient "at risk for developing metastatic cancer" refers to a patient after resection of a primary tumor.

As used herein, a patient "at risk for metastatic relapse" refers to a patient suffering from metastatic disease who is more likely than not to develop metastatic relapse or such and therefore additional therapeutic intervention may be necessary and/or beneficial to combat disease in the at risk patient. Identifying cancer patients who are at risk for metastatic relapse can be carried out using any method known to one skilled in the art, such as analysis of genetic mutations (i.e. carriers of the BRCA2 mutation, K-ras mutation, etc.), gene expression analysis (i.e. measurement of changes in gene expression profile, either up-regulation or down-regulation, characteristic of metastases), loss of tumor suppressor protein (i.e. p53 etc.), upregulation of oncogene (i.e. Erb2, etc.), or protein expression analysis (i.e. measurement of changes in protein expression profiles, either upregulation or downregulation, characteristic of metastases), etc.

The term "control" refers to subjects or patients or samples or cells or antibodies etc. which provide a basis for comparison in an experiment. For instance, the use of control samples when the experiment comprises a test sample permits determinations to be made regarding the efficacy of experimental procedures. In some embodiments, the term "control subject" refers to animals that receive a mock treatment (e.g., PBS alone or normal rabbit IgG in saline), such as isolated neutrophils undergoing an identical entrainment method but without adding an entrainment agent, i.e. CCL2, CCL5, or others such as CXCL12.

The term "purification" or "purify" or "isolated" or "isolating" when used in relation to a cell population, as in "isolating white blood cells" or "isolated neutrophils" or "isolating neutrophils" refers to a population of cells that is separated from at least one other population of cells with which it is ordinarily associated in its natural source, i.e. "isolated white blood cells" refers to separating a population of white blood cells (WBCs) from a mixture of white blood cells and red blood cells found naturally in a whole blood sample, for examples, hypotonic lysis of the whole blood sample would remove red blood cells from WBCs, a buffy coat isolation using Ficoll-Hypaque provides layers of WBCs, (i.e., moncytes, lymphocytes, neutrophils, etc.) and platelets covering the top of the packed red blood cells, Percoll separation, MACS (magnetic antibody cell separation), and the like. In another example, "isolated neutrophils" or "purified neutrophils" or "neutrophil purification" refers to separating a subpopulation of white blood cells from a mixture of isolated white blood cells or a mixture of white blood cells and red blood cells found naturally in a blood sample, for example, methods of purification include but are not limited to discontinuous one-step Ficoll-Hypaque gradient (Ferrante and Thong, 1978, herein incorporated by reference), Histopaque discontinuous gradients, MACS (magnetic antibody cell separation), and any method resulting in a population of neutrophil cells of the present inventions, i.e. white blood cells capable of mediating tumor cell death.

The term "leukocyte" as used herein, refers to cells called white blood cells that help the body fight infections and other diseases, and include for instance granulocytes (e.g., neutrophils, eosinophils, basophils), mononuclear phagocytes, and lymphocytes (e.g., B cells, T cells, natural killer cells).

As used herein, the term "monocyte" refers to a mononuclear phagocyte circulating in blood that will later emigrate into tissue and differentiate into a macrophage.

The term "macrophage" refers to relatively long-lived phagocytic cells of mammalian tissues, derived from blood monocytes. Macrophages from different sites have distinctly different properties. Main types are peritoneal and alveolar macrophages, tissue macrophages (histiocytes), Kupffer cells of the liver and osteoclasts. Macrophages play an important role in killing some bacteria, protozoa and tumour cells, in releasing substances that stimulate other cells of the immune system, and presenting processed antigen to T lymphocytes.

The terms "neutrophil" and "neutrophil-like cell" (collectively referred to herein as neutrophils) refers to granular white blood cells with neutrophil type morphology or partitioning into or adjacent to neutrophil layers during density separations, i.e. separations of which blood cells intending to isolate or purify neutrophils from other white blood cell types. In one embodiment, mouse neutrophils may be identified as $CD11b^{hi}Ly6G^+$, in another embodiment; mouse neutrophils may be identified as "Gr-1+" or "RB6-8C+", in another embodiment; neutrophils may be identified as MMP9+, etc. In one contemplated embodiment, human neutrophils may be identified as comprising cell receptors CCR1, CCR2, CCR4, CCR5, CXCR4 as well as receptors which bind to CCL2, CCL5, CXCL12 and other chemokines which increase cytotoxic activity of a neutrophil for a cancer cell; in another embodiment, human neutrophils may be identified as comprising MMP9 markers.

As used herein, the term "tumor-entrained neutrophils" or "tumour-entrained neutrophils" or "entrained neutrophils" or "TENs" or "TENs-like phenotype" refers to white blood cells of the present inventions isolated from subjects previously diagnosed with cancer or known to have cancer cells wherein said TENs are capable of killing tumor cells directly or after incubation in culture comprising an "entraining formulation" or after ex vivo exposure, i.e. contact, to a chemokine of the present inventions, such as CCL2, CCL5, and the like, such entrained neutrophil can also be referred to herein as a "contacted neutrophil." In one embodiment, TENs refers to cells used in methods of the present inventions, i.e. white blood cells capable of mediating cytotoxic effects upon tumor cells or directly killing tumor cells for example, "cytotoxic neutrophils."

The term "naïve" in reference to a neutrophil as in "naïve neutrophil" refers to neutrophils isolated from a subject believed to be free of cancer cells/tumor cells.

The term "cytotoxic neutrophil" or a cell with a "TENs-like phenotype" refers to the capability of neutrophils to have cytotoxic activity, for example, cytotoxicity due to generation of reactive oxygen species providing a capability for oxidative activity, such as produced by the NAPDH Oxidase complex for providing an "oxidative burst." In other words, a neutrophil of the present inventions capable of killing tumor cells directly or indirectly. In a contemplated embodiment, human cytotoxic neutrophils of the present intentions comprise a MMP9 marker. In other embodiments, human neutrophils of the present inventions comprise receptors for CCL2 and/or CCL5, such as CCR1, CCR2, CCR4, CCR5, and any receptor capable of binding CCL2 or CCL5 or a chemokine with comparable activity. In another embodiment, human neutrophils of the present inventions may be referred to as cytotoxic neutrophils. In yet another embodiment, human neutrophils of the present inventions may be referred to as mediating cancer cell death.

The term refers to a cytotoxic effect or cytotoxic activity resulting in the death of a tumor cell, for example, a cytotoxic effect is an oxidative burst, triggering a receptor on a tumor cell that causes the death of the tumor cell, and the like.

The term "capable of killing" or "neutrophil cytotoxicity" or "cytotoxic activity" or "cytotoxic to a tumor cell" in general refers to the capability of one cell for killing another cell measured in cytotoxicity assays, such as cytotoxic lymphocyte assays. In one example, a target cell, i.e., a tumor cell/cancer cell or control noncancer cell is labeled with compound, such as luciferase, whose reaction for producing light is dependent of ATP produced by living cells. Upon the death of a cell, such as in a co-culture of neutrophil effector cells with target tumor cells, luciferase production is reduced as ATP is depleted. A read out of luciferase activity is proportional to the remaining activity and can be normalized by cell number in order to determine the cell killing capability of an effector cell. An example of an in vitro cytotoxic killing assay, luciferase expressing target cells are incubated with effector cells for 2-6 hours. Luciferin is then added to the cells for optical imaging of a relative light signal. In another example, a target cell, i.e. a tumor cell/cancer cell or control noncancer cell is labeled with compound, such $^{51}C$, that is released upon the death of a cell and measured in collected cell media in order to determine the cell killing capability of an effector cell. In one embodiment, the cell killing capability of a neutrophil of the present inventions is measured and shown in ratios, for example, 10 effector neutrophil of the present inventions is determined to kill 1 cancer cell, i.e. 100:1, 10:1, 1:1, etc.

As used herein, the term "increasing cytotoxic activity" or "increasing cytotoxic activity of a neutrophil" refers to increasing the cell killing capacity of an effector cell, i.e. neutrophil. One example of "increasing cytotoxic activity of a neutrophil" is comparing the level of killing of isolated neutrophils compared to an identical sample of isolated neutrophils contacted with a chemokine, such as CCL2, wherein the % killing was increased, for example, see FIG. 25, * and ** comparisons.

As used herein, the term "neutrophil mediated tumour-cell killing" or "mediating tumor cell death" or "mediating killing" in reference to a neutrophil described herein, refers to causing the death of a tumor cell in a co-culture of tumor cells, i.e. cancer cells with TENs of the present inventions or when TENs, i.e. contacted neutrophils, are administered to a patient for mediating tumor cell death, as one example for inhibiting metastasis of a tumor cell. In one embodiment, tumor cell killing may be mediated by oxidative activity of the neutrophil.

As used herein, the term "neutrophil mediated inhibition of metastasis" refers to the capability of TEN neutrophils to inhibit metastasis including metastatic seeding, growth of a new tumor, such as when a metastatic cell establishes a new tumor, regression of established metastasis or the killing of seeded but quiescent metastasis.

As used herein, the term "apoptosis in a tumor cell" refers to the death of a tumor cell, such as receptor mediated cell death, cell death induced by an oxidative burst of a neutrophil, caspase 3 mediated cell death, and the like.

As used herein, the term "prevention" or "inhibition" or "inhibited" in reference to metastasis in a patient refers to any reduction in symptoms of cancer cell metastasis, i.e. reducing/delaying the spread of cancer cells within a patient, a slowing of progression of metastasis, such as migration outward from a primary tumor, a slowing of progression of metastatic disease, a slowing of tumor growth, reduction in tumor growth, i.e. size, and the like. One example of inhibition of metastasis in a patient, is the reduction in or absence of tumor cells in tissue surrounding the site of a tumor, another example is the reduction in or absence of tumor cells in draining lymph nodes of the primary site of tumor growth, for example in a patient with breast cancer, a lower number of tumor cells than usually observed with metastatic disease in draining lymph nodes, such as axilla (underneath a patient's arm), in other words sentinel lymph nodes.

As used herein, the term "detection of metastasis" or "detection of tumor cell metastasis" refers to identifying a metastatic cancer cell in the tissue surrounding a tumor or in circulating in the blood of a patient or in the tissue near a draining lymph node/in the draining lymph node for the tissue containing the tumor, or found in tissues/organs that were not the location of the initially detected tumor. One example for identification of tumor cells in tissue including lymph nodes is through known biopsy techniques, such as a needle biopsy. One example for identification of tumor cells in a patient, including for staging and monitoring primary (de novo) and metastatic cancer in a patient, and identifying recurrent of metastatic disease, such as a patient with breast cancer, is a Positron Emission Tomography (PET) scan, a computed axial tomography (CAT or CT scan), a Magnetic resonance imaging (MRI), a nuclear magnetic resonance imaging (NMRI), magnetic resonance tomography (MRT), and the like. One example for identification of tumor cells circulating in the blood is a CellSearch™ System, Veridex, LLC.

As used herein, the term "personal ex-vivo therapeutic" refers to a pharmaceutical composition comprising "TENs" as described herein.

As used herein a "pharmaceutical composition" is a pharmaceutically active agent that has been admixed with conventional pharmaceutical buffers, carriers and excipients (i.e., vehicles) and used in the form of aqueous solutions. An agent may be a biological molecule, such as G-CSF. A pharmaceutical composition in reference to neutorphils of the present inventions refers to composition comprising an isolated neutrophil of the present inventions admixed with an aqueous solution. For injection, the pharmaceutical compositions of the invention may be formulated in aqueous solutions, preferably in physiologically compatible buffers such as Hanks' solution, Ringer's solution, or physiologically buffered saline. For example, for administering neutrophils to a patient, the neutrophils may be in a pharmaceutical composition and can be administered intravenously or by another method that distributes the cells within the patient.

As used herein, the term "entraining formulation" refers to a cytokine formulation added to TENs in culture resulting in neutrophils that mediate cell killing in vitro or inhibit metastatic cancer in vivo, prevent metastatic cancer in vivo, and the like.

As used herein, the term "contacting" refers to placing a substance such as a chemokines or agent in a location that will allow it to touch a cell in order to produce "contacted" cells. The contacting may be accomplished using any suitable method. For example, in one embodiment, contacting is by adding the substance to a vial of cells. Contacting may also be accomplished by adding the agent to a culture of the cells. It is not meant to limit how the substance contacts the cells. In one embodiment, contacting may be accomplished by administration of substance to a subject in vivo.

As used herein, the term "cell culture" refers to any in vitro culture of cells. Included within this term are continuous cell lines (e.g., with an immortal phenotype), primary cell cultures, i.e. isolated neutrophils, transformed cell lines, finite cell lines (e.g., non-transformed cells), and any other cell population maintained from hours or days or years in vitro.

As used herein, the term "suspension" and "suspension culture" refers to cells that survive, with or without proliferation, without being attached to a substrate. Suspension cultures are typically produced using hematopoietic cells, such as white blood cells, transformed cell lines, cancer cells, cancer cell lines, and cells from tumors.

As used herein, the term "proliferation" refers to an increase in cell number.

As used herein, the term "agent" refers to a compound added to a formulation, such as GM-CFS, TNF-alpha, lipopolysaccharide, etc.

As used herein, the term "pharmaceutical formulation" refers to a composition which generally comprise an effective amount of a biologically active agent, for example, an active agent G-CSF as a recombinant methionyl human granulocyte colony-stimulating factor in Filgrastim/NEUPOGEN®.

As used herein, the terms "antagonist" and "inhibitor" refer to molecules or compounds that inhibit the action of a "native" or "natural" compound, for example, a TGFbeta inhibitor. Antagonists may or may not be homologous to these natural compounds in respect to conformation, charge or other characteristics. Thus, antagonists may be recognized by the same or different receptors that are recognized by an agonist. Antagonists may have allosteric effects, which prevent the action of an agonist (e.g., prevent native TGFbeta from binding to TGFbeta receptors). In contrast to the agonists, antagonistic compounds do not result in physiologic and/or biochemical changes within the cell such that the cell reacts to the presence of the antagonist in the same manner as if the natural compound was present. Antagonists and inhibitors may include proteins, nucleic acids, carbohydrates, or any other molecules that bind or interact with TGFbeta binding proteins or which prevent the function of TGFbeta, for example, "fmlp" (N-formyl-methionine-leucine-phenylalanine), and SB 431542 (Tocris Biosciences).

When a "+" sign is associated with the name of a marker it refers to the presence of that marker, for example, "Gr-1+" refers to the presence of a Gr-1 marker. Alternatively, when a "-" sign is associated with a marker it refers to the absence of that marker, for example, "Gr-1−" refers to the absence of a Gr-1 marker. A marker may be detected by a variety of methods, such as immunohistochemistry, immunoflouresence, PCR, and the like.

When "hi" is associated with the name of a marker it refers to both the presence of that marker and a relatively high amount of expression often determined by relatively dark staining by immunohistochemistry or a relative higher intensity immunofluorescent signal than low or negative cells in a population by flow cytometry, for example, the population at least such as between the second and third log intensity of signal as opposed to at least between the first second log by flow cytometric analysis, for example, CD11b$^{hi}$ may refer to cells with dark immunohistochemistry staining for a CD11b specific antibody whereas unstained cells in the same sample or control cells in a duplicate sample show no such specific staining. Alternatively, when "lo" is associated with the name of a marker it refers to both the presence of that marker and a relatively low amount of expression often determined by relatively light staining by immunohistochemistry and between the first log intensity of signal by flow cytometric analysis, for example, CD11b$^{hi}$ may refer to cells with dark immunohistochemistry staining for a CD11b specific antibody compared to unstained cells in the same sample or control cells in a duplicate sample that show no such specific staining.

The term "granulocyte-differentiation antigen-1" or "anti-granulocyte receptor-1" or "Gr-1" in reference to a Gr-1 antibody, i.e. "Gr-1 antibody" such as RB6-8C5, refers to an epitope present on neutrophils, dendritic cells, and subpopulations of lymphocytes and monocytes in mice. RB6-8C5 binds to both Ly6G, which is present on neutrophils, and to Ly6C, which is expressed on neutrophils, dendritic cells, and subpopulations of lymphocytes and monocytes. While Ly-6G is considered specific for mouse neutrophils, Ly-6C is expressed on both neutrophils and a subset of monocytes.

The term "Ly6g" or "lymphocyte antigen 6 complex, locus G mouse myeloid differentiation antigen" or "myeloid differentiation antigen Gr-1" or "Gr-1" in reference to a protein or marker refers to a neutrophil specific marker expressed by mouse neutrophils.

As used herein, the term "CD11b" or "integrin αM subunit" or "integrin alpha M" or "ITGAM" or "Mac-1 alpha" or "Mac1A" or "Complement Receptor 3 alpha" or "CR3A" refers to a white blood cell marker. "CD11b" combines with CD18 (integrin β2 subunit) to form the integrin Mac-1, also referred to as complement receptor 3 (CR3).

As used herein, the term "Mac-1" refers to a dimer comprising CD11b, for example expressed on myeloid and natural killer cells, Mac-1, i.e. CD18/CD11b, is a member of the beta2-integrin family of adhesion molecules.

As used herein, the term "clusters of differentiation" or "CD" in reference to a cell marker refers to a nomenclature system developed and intended for the classification of individual cell markers where many monoclonal antibodies (mAbs), generated by different laboratories around the world, are used generating many names for the same antigen for surface molecules (antigens) on leukocytes (white blood cells). In other words, for antibodies that recognize Mac-1 and other antibodies that recognize CR3A are unified under antibodies that recognize the same antigen, i.e. CD11b.

As used herein, the term "Chemokine (C-C motif) ligand 2" or "CCL2" refers to a small cytokine belonging to the CC chemokine superfamily that is also known as "Monocyte chemotactic protein 1" or "MCP-1" or "monocyte chemotactic and activating factor" or "MCAF" (for example, see, Gu, et al. (1999) Chem; Immunol. 72:7, herein incorporated by reference).

As used herein, the term "CCL2" also refers to a ligand for the seven transmembrane domain G-protein-coupled receptor "CCR2" or "chemokine (C-C motif) receptor 2" which refers to a receptor with at least two isoforms. "MCP-1W" shares the CCR2 receptor with several other ligands including MCP-2 (CCL8), MCP-3 (CCL7), MCP-4 (CCL13), and mouse MCP-5.

As used herein, the term "RANTES" or "Regulated upon Activation, Normal T Expressed and Secreted" or "CCL5" refers to a member of the "CC" subfamily of chemokines, i.e. interleukin-8 superfamily of cytokines. CCL5 plays a primary role in the inflammatory immune response via its ability to chemoattract leukocytes and modulate their function. CCL5 is known to interact with four identified seven transmembrane G-protein coupled receptors: CCR1, CCR3, CCR4, and CCR5 (Neote, et al. (1993) Cell 72:415; Ponath, et al. (1996) J. Exp. Med. 183:2437; Power, et al. (1995) J. Biol. Chem. 270:19495; Combadiere, et al. (1996) 60:147, all of which are herein incorporated by reference). CCL5 may bind to any of CCR1, CCR3, CCR4 and CCR5 receptor proteins.

As used herein, the term "chemokines" or "chemotactic cytokines" or "CHEMO-attractant C Family" refer to regulatory proteins produced by many different cells in the body. In general, chemokines, often referred to as cytokines, belong to a family of chemical messenger molecules involved in cell function, in particular white blood cells. Over fifty human chemokines have been identified that can be categorized into at least four groups; CC (i.e. C-C Chemokine), CXC (i.e. CXC-chemokine), $CX_3C$ and C (XCL1 and XCL2); depending on the spacing of their first two cysteine residues in their amino acid sequence. A human chemokine network is made up of at least 50 known chemokine ligands (which bind to chemokines receptors) and approximately two dozen identified chemokine receptors. Different chemokines are made in different tissues at different times and different chemokine receptors are expressed on the surface of different types of inflammatory cells. Those cells can only respond to a chemokine in a given organ or tissue if the cell possesses a receptor that specifically recognizes the chemokine that is present in the local environment. In this way, each chemokine-chemokine receptor combination may direct a different inflammatory response and this response can be tailored by the body based on the type of injury, irritation, or other threat.

As used herein, the term "effective amount" refers to the amount of a pharmaceutical composition comprising TENs sufficient to effect beneficial or desired results. An effective amount can be administered in one or more administrations, applications or dosages and is not intended to be limited to a particular formulation, such as a particular pharmaceutical composition or formulation or administration route.

As used herein, the terms "administration" and "administering" refer to the act of giving an agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "treatment" or grammatical equivalents encompasses the improvement and/or reversal of the symptoms of disease (e.g., neurodegenerative disease). A compound which causes an improvement in any parameter associated with disease when used in the screening methods of the instant invention may thereby be identified as a therapeutic compound.

The term "treatment" refers to both therapeutic treatment and prophylactic or preventative measures. For example, those who may benefit from treatment with compositions and methods of the present invention include those already with a disease and/or disorder (e.g., breast cancer, etc.) as well as those in which a disease and/or disorder is to be prevented (e.g., using a prophylactic treatment of the present invention).

The term "inflammation" as used herein, refers to the tissue response to trauma, characterized by increased blood flow and entry of leukocytes into the tissues, resulting in swelling, redness, elevated temperature and pain.

As used herein, the term "symptom" refers to any subjective evidence of disease or of a patient's condition (e.g., a change in a patients condition indicative of some bodily or mental state). Similarly, the phrase "under conditions such that the symptoms are reduced" in the context of metastatic cancer refers to any degree of qualitative or quantitative reduction in detectable secondary cancer, including but not limited to, a detectable impact on the rate of recovery from disease (e.g., rate of weight gain).

As used herein the term "portion" when in reference to a protein (as in "a portion of a given protein") refers to fragments of that protein. The fragments may range in size from four amino acid residues to the entire amino acid sequence minus one amino acid.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

The terms "sample" and "specimen" are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid, semen, saliva, and wound exudates, as well as solid tissue. However, these examples are not to be construed as limiting the sample types applicable to the present invention.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the inhibition of the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures.

The term "shRNA" or "short hairpin RNA" refers to a DNA molecule that can be cloned into expression vectors to express siRNA (19-21nt RNA duplex) for RNAi interference.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

D. Blood differentials performed on days 5, 8 and 10 show a dramatic increase in circulating neutrophils numbers in tumour-bearing mice (Tumour+IgG) compared to the controls No tumour+IgG). The increase in circulating neutrophils numbers is abolished in mice treated with Gr-1 antibody (Tumour+Gr-1). E. MMP9 immunohistochemistry shows that Gr-1 treatment abolishes the accumulation of neutrophils in the lungs and at the tumour-rim of tumour-bearing mice. F. Colony formation assay performed on lungs from control (No tumour+IgG), tumour-bearing (Tumour+IgG) and neutrophil-depleted tumor-bearing mice (Tumour+Gr-1). While tumour-bearing mice show enhanced seeding of tumour cells in the lung when compared to controls, the depletion of neutrophils results in a further increase in tumour-cell seeding capacity in the lungs.

G. Neutrophil depletion has no significant effect on tumour volume.

Figures 1, 3:
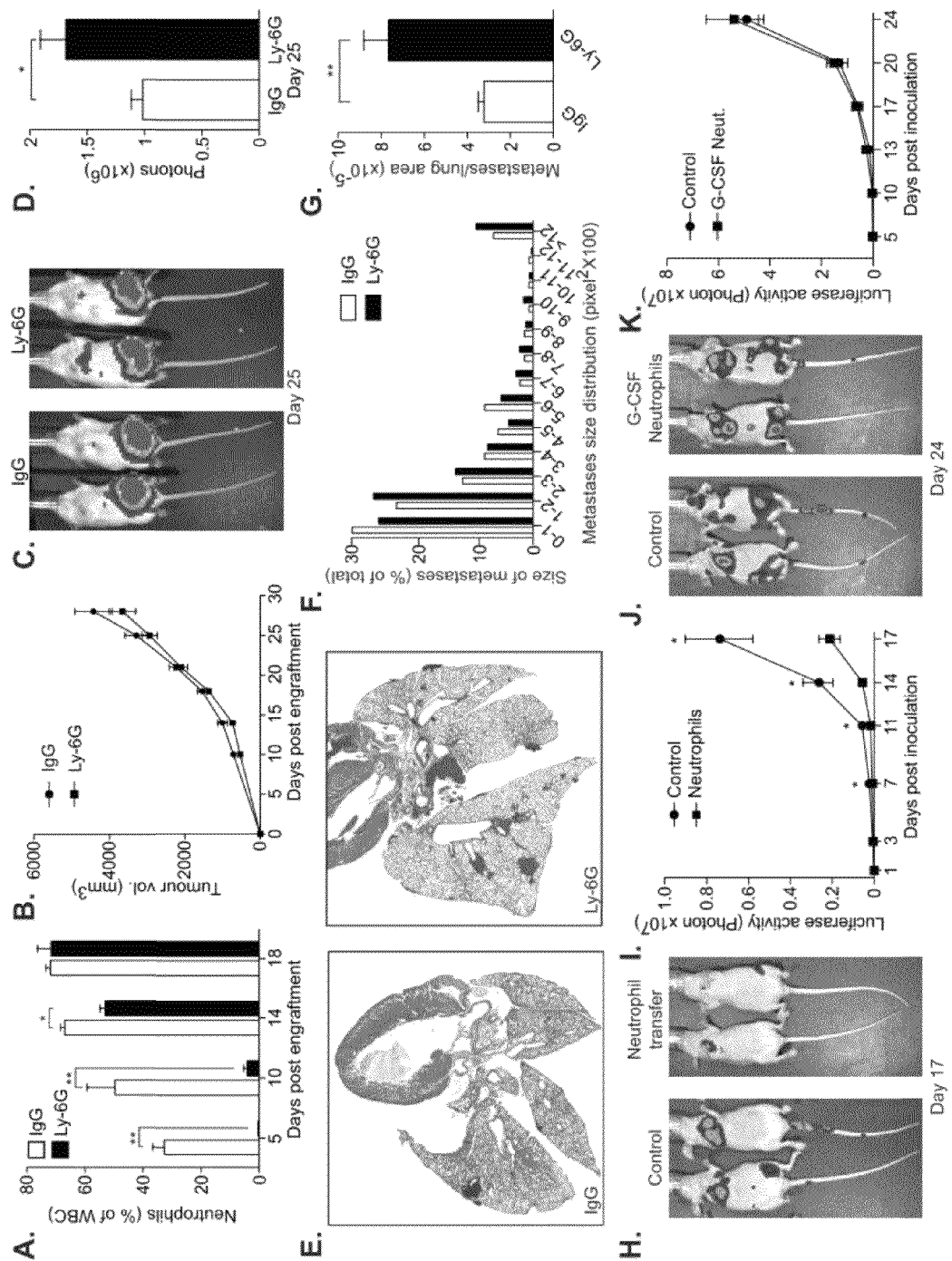
Figures 2, 3:
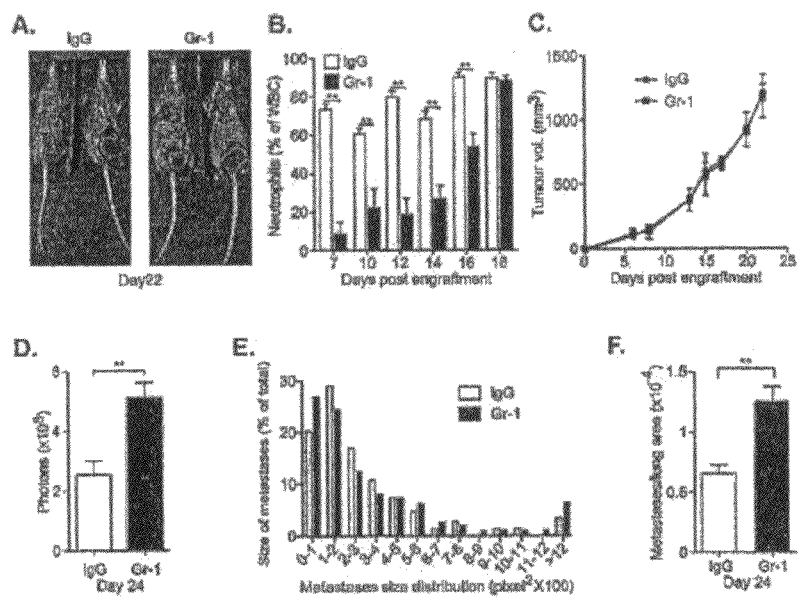
Figure 3:
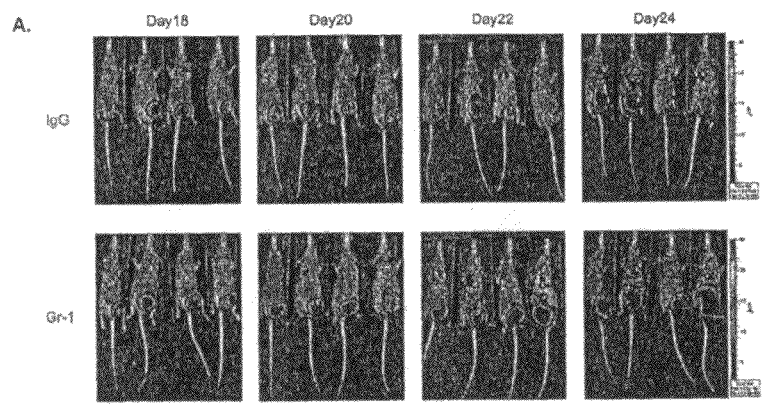

FIG. 3 presents exemplary Gr-1 antibody depleted mice compared to control mice (IgG) attenuated spontaneous formation of lung metastases. Mice were orthotopically (mammary fat pad) engrafted with $5\times10^6$ Luciferase-labelled 4T1 cells. Starting on day 3, the mice were treated with either a neutrophil depleting (Gr-1) or a control (IgG) antibody. Luciferase activity was used to follow the formation of lung metastases in vivo.

A. Representative images showing increased luciferase activity emanating from the lungs of neutrophil depleted mice (Gr-1) compared to control mice (IgG). B. Blood differentials show that neutrophil depletion was highly effective until day 16 after which there was no significant difference between control and Gr-1 treated mice. C. Tumour size measurements throughout the course of the experiment show no significant difference between control and Gr-1 treated mice. D. Quantification of lung specific Luciferase activity shows that metastases form earlier and grow faster in neutrophil-depieted (Gr-1) mice, E. Representative images showing that transfer of TENs attenuates the formation of lung metastases after tail-vein injection of tumour cells. F. Quantification of lung specific Luciferase activity shows that TENs significantly delay the formation of lung metastasis.

G. Similar results were obtained in 3 independent neutrophil-transfer experiments; These results are summarized as averaged ratio of lung specific Luciferase activity of control/neutrophil-transfer mice.

Figure 1:
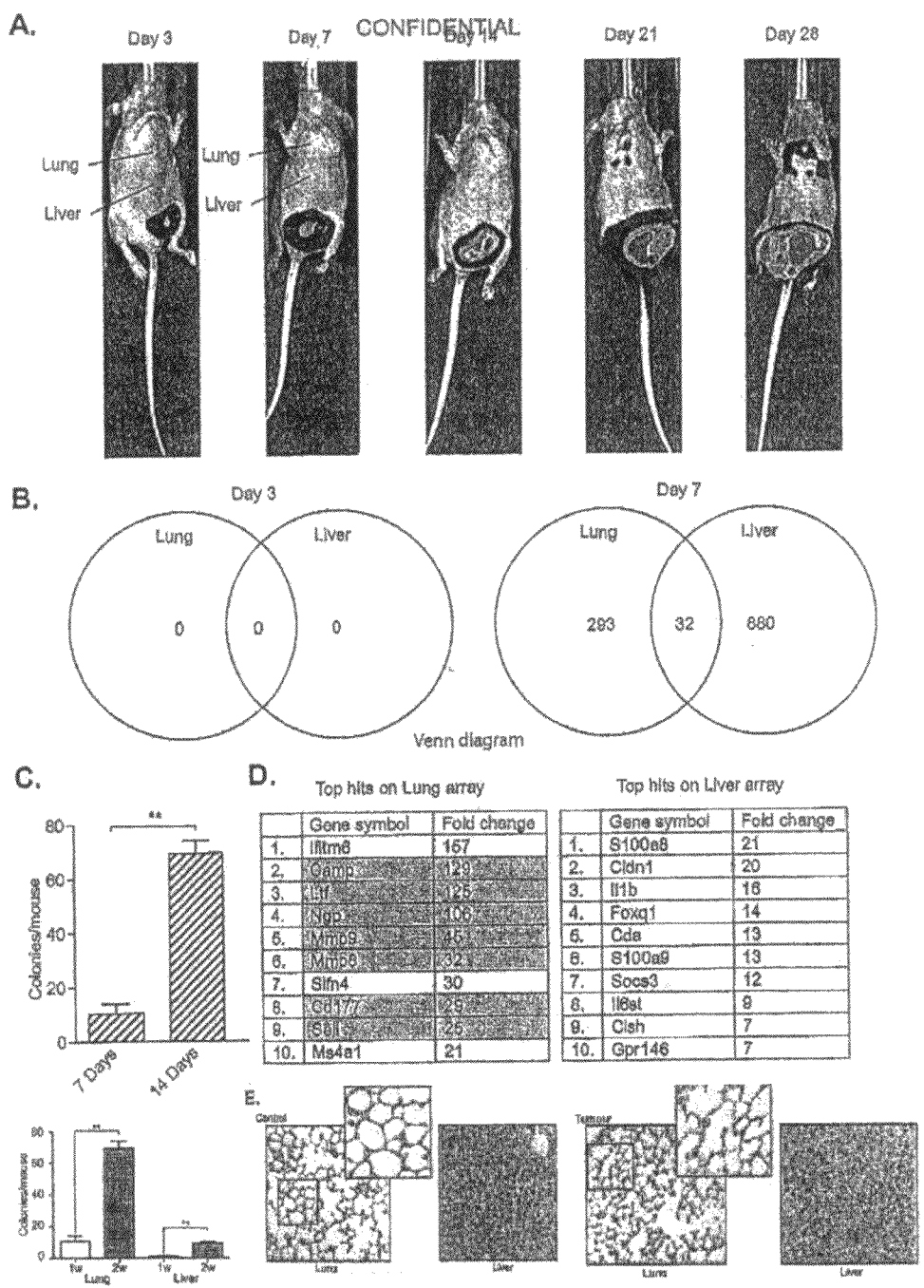
FIG. 1 presents exemplary early transcriptional changes in the pre-metastatic lung and liver. A. Orthotopically engrafted murine mammary Luciferase-labelled 4T1 tumor cells form mammary tumor that spontaneously metastasize to the lungs. Lung specific Luciferase activity, emanating from lung metastases, can be readily visualized by day 21. Lung and liver mRNA samples were taken 3 and 7 days after tumor implantation. B. Venn diagram summarizing the transcriptional changes in the lung and the liver from sham operated vs. 4T1 tumor bearing mice. While there were no significant transcriptional changes on day 3, there were 325 and 912 significantly misregulated genes in the lung and liver (respectively) of tumor bearing mice. Of the misregulated genes, 32 genes were misregulated in both the lung and the liver. C. To quantitate the number of tumor cells in the lungs the number of colony forming cells was measured in a single cell suspension prepared from the lungs of tumor bearing mice on day 7 and 14. There were 10.5+/−3.5 and 69.5+/−4.5 tumor cells per lung on days 7 and 14 respectively (upper graph). D. Top 10 up regulated genes in lung and liver expression array. Highlighted genes are expressed in myeloid cell lineages.

FIG. 3-1 presents exemplary TENs attenuate the spontaneous formation of lung metastases. Female Balb/c mice were orthotopically (mammary fat pad) engrafted with $5\times10^6$ luciferase-labelled 4T1 cells. Starting on day 3, the mice were treated with either a neutrophil depleting (Ly-6G) or a control (IgG) antibody. Luciferase activity was used to follow the formation of lung metastases in vivo. A. Blood differentials show that neutrophil depletion was highly effective until day 14 after which there was no significant difference between control and Ly-6G treated mice. B. Measurements of primary tumour size throughout the course of the experiment show no significant difference between control (IgG) and neutrophil depleted (Ly-6G) mice. C. Representative images showing increased luciferase activity emanating from the lungs of neutrophil depleted mice (Ly-6G) compared to control mice (IgG). D. Quantification of lung specific luciferase activity shows increased metastatic burden in neutrophil-depleted (Ly-6G) mice compared to controls (IgG). E. Representative lung H&E images showing the formation of spontaneous metastases in control (IgG) and neutrophil depleted (Ly-6G) mice by day 25 post tumour engraftment. F. Histological evaluation of metastatic foci size shows that control (IgG) and neutrophil depleted (Ly-6G) mice have the same metastases size distribution. G. Histological evaluation of the number of metastatic foci shows that neutrophil depleted (Ly-6G) mice have significantly more metastatic events per lung area compared with control (IgG) mice. H. Representative images showing that transfer of TENs attenuates the formation of lung foci after tail-vein injection of tumour cells in nude mice. I. Quantification of lung specific luciferase activity shows that TENs significantly delay the formation of lung foci. J. Representative images showing that transfer of G-CSF mobilized neutrophils has no effect on the formation of lung foci after tail-vein injection of tumour cells in nude mice. K. Quantification of lung specific luciferase activity shows that G-CSF mobilized neutrophils do not delay the formation of lung foci. (* $p<0.05$, ** $p<0.01$).

Figure 2:
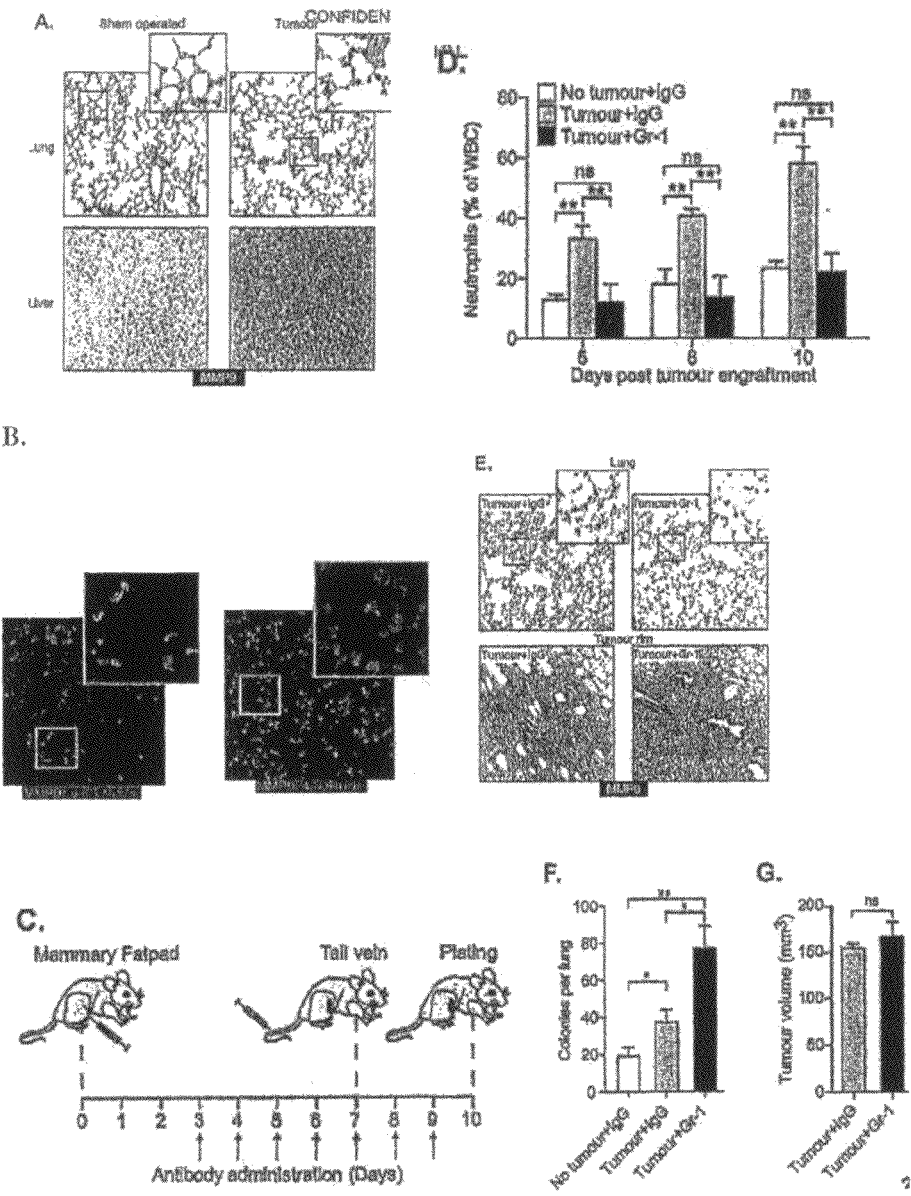
FIG. 2 presents exemplary neutrophil accumulation in the pre-metastatic lung and inhibition of tumour cell seeding, A. MMP9 immunohistochemistry performed on lung and liver tissues from tumor-bearing or sham-operated mice on day 7 shows a dramatic increase in MMP9+ cells in the lungs but not in the liver. B. Co-staining of lung tissue from tumour-bearing mice on day 7 shows that MMP9 (green/light) co-localizes with Ly-6G (red on left panel) but not with F4/80 (red/dark on right panel). C. Experimental design—on day 0, $5 \times 10^6$ 4T1 cells were injected into the mammary fat pad to generate a primary tumour. Control mice were sham operated and injected with PBS. Starting on day 3, the mice were treated with a neutrophil depleting (Gr-1) antibody or with isotypic control IgG. On day 7 all mice were challenged with a tail-vein injection of $5 \times 10^4$ puromicin-resistant cells. On day 10 the mice were sacrificed and a single cell suspension prepared from the lungs was plated on puromicin containing plates.

FIG. 3-2 presents exemplary neutrophil depletion increases the number of metastatic events rather than metastases size in a T-Cell independent mechanism. Female nude mice were orthotopically (mammary fat pad) engrafted with $5\times10^6$ luciferase-labelled 4T1 cells. Starting on day 3, the mice were treated with either a neutrophil depleting (Gr-1) or a control (IgG) antibody. Luciferase activity was used to follow the formation of lung metastases in vivo. A. Representative images showing increased luciferase activity emanating from the lungs of neutrophil depleted mice (Gr-1) compared to control mice (IgG). B. Blood differentials show that neutrophil depletion was highly effective until day 16 after which there was no significant difference between control and Gr-1 treated mice. C. Measurements of primary tumour size throughout the course of the experiment show no significant difference between control and Gr-1 treated mice. D. Quantification of lung specific luciferase activity shows higher metastatic burden in neutrophil-depleted (Gr-1) nude mice. E. Histological evaluation of metastatic foci size shows that control (IgG) and neutrophil depleted (Gr-1) mice have the same metastases size distribution. F. Histological evaluation of the number of metastatic foci shows that neutrophil depleted mice (Gr-1) have significantly more metastatic events per lung area compared with control mice (IgG). (* $p<0.05$, ** $p<0.01$).

FIG. 3-3 shows exemplary depletion of Gr-1+ cells in tumor bearing mice. To test the long-term implications of neutrophil depletion on tumor growth and metastasis 4T1-tumor bearing mice were treated with either a control antibody (IgG) or a neutrophil depleting antibody (Gr-1). In vivo monitoring of lung metastases formation was made possible using Luciferase labeled 4T1 cells. Conclusion—tumor stimulated neutrophils attenuate the lung metastatic process.

Figure 4:
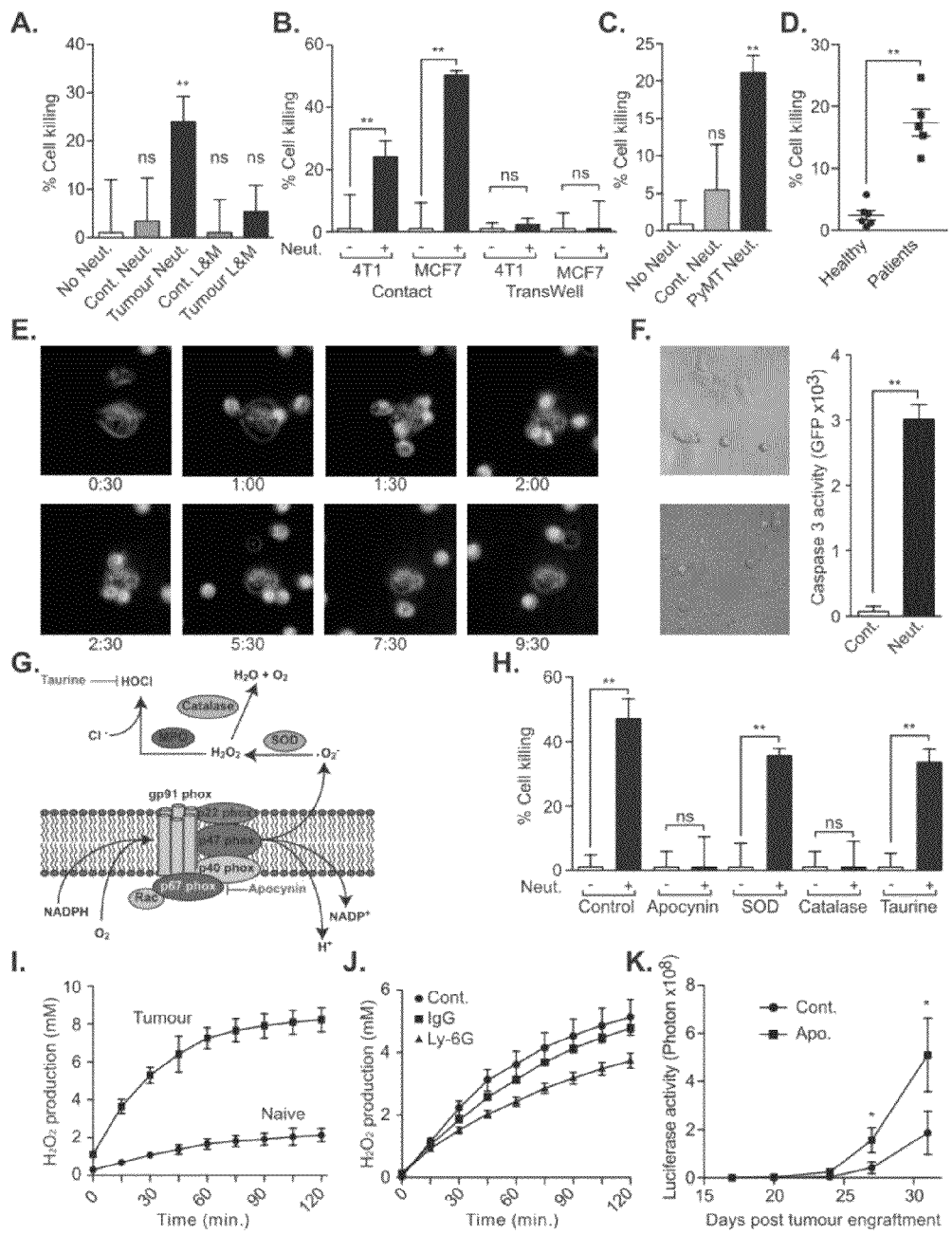

FIG. 4 shows exemplary TENs killed tumour cells through the NADPH Oxidase—$H_2O_2$ pathway. A. Plated luciferase-labelled 4T1 cells were co-cultured with neutrophils (Neut.) or a mixture of Lymphocytes and Monocytes (L&M) purified from the circulation of sham-operated (Cont.) or 4T1 tumour-bearing (Tumour) mice. Cell killing was estimated by luciferase activity. Control neutrophils as well as Lymphocytes and Monocytes purified from either control or tumour-bearing mice, had no cytotoxic effect (compare to 4T1 cells alone—no neut.). In contrast, neutrophils purified from tumour-bearing mice were highly cytotoxic. B. Neutrophils purified from 4T1 tumour-bearing mice have the capacity to kill murine 4T1 breast cancer cells as well as human MCF7 breast cancer cells. No killing is observed when 4T1 or MCF7 cell are cultured with TENs in a TransWell plate suggesting that tumour-cell killing requires physical contact. C. Neutrophils purified from wild type (Cont. Neut.) or mammary tumour-bearing MMTV-PyMT mice (in FVB background) were co-cultured with 4T1 cells. While control neutrophils had no effect on tumour-cell viability, MMTV-PyMT TENs gained the capacity to kill 4T1 cells in vitro. D. Neutrophils purified from healthy human volunteers (Healthy) or breast cancer patients (Patients) were co-cultured with luciferase labelled MDA-MB-231 cells.

While neutrophils purified from healthy volunteers had no significant cytotoxic effect, neutrophils purified from breast cancer patients show a dramatic increase in cytotoxicity. E. Time-lapse microscopy showing a co-culture of GFP labelled TENs (green) purified from 4T1 tumour bearing Ubc-GFP Balb/c mice and CellTracker-Red labelled 4T1 cells (red). As early as 1 h after their addition to the culture, neutrophils initiate physical contact with the adherent 4T1 cells resulting in morphological changes and fragmentation of the tumour cells. F. Representative images showing 4T1 cells pre-labelled with NucView 488 Cleaved Caspase 3 activity reporter cultured alone (top) or in co-culture with TENs (bottom). While no GFP positive (activated Caspase 3) cells are visible in the TEN-free culture, several GFP positive cells are visible in the 4T1+TEN co-culture. Quantification of GFP intensity as an estimate for apoptosis shows a dramatic increase in GFP intensity in the 4T1+TEN co-culture compared with control. G. Neutrophils generate superoxides through the enzymatic activity of the NADPH Oxidase complex. Singlet oxygen generated by oxidizing NADPH can be converted into $H_2O_2$ by cellular superoxide dismutase (SOD). Neutrophil Myeloperoxidase (MPO) can convert $H_2O_2$ to hypochlorous acid (HOCl). The NADPH-Oxidase inhibitor Apocynin inhibits the formation of the NADPH Oxidase complex, exogenous catalase catalyzes the formation of $H_2O$ and $O_2$ from $H_2O_2$, exogenous taurine reacts with HOCl to inhibit cytotoxicity H. Co-culture of 4T1 tumour cells with TENs in the presence of the Apocynin, completely inhibits tumour cell killing. In contrast Superoxide Dismutase (SOD) does not. The presence of Catalase completely inhibits tumour-cell killing. Addition of the Hypochlorous-acid scavenger—Taurine, does not inhibit tumour-cell killing. I. Comparison of $H_2O_2$ production in purified control neutrophils (naïve) and TENs (Tumour) shows that TENs produce dramatically more $H_2O_2$ than control neutrophils. J. $H_2O_2$ production by purified TENs is reduced in the presence of Ly-6G by not by control IgG. K. Quantification of lung specific luciferase activity shows that metastatic progression is enhanced in Apocynin (Apo.) treated tumour-bearing mice compared to control (Cont.). (* $p<0.05$, ** $p<0.01$).

Figure 5:
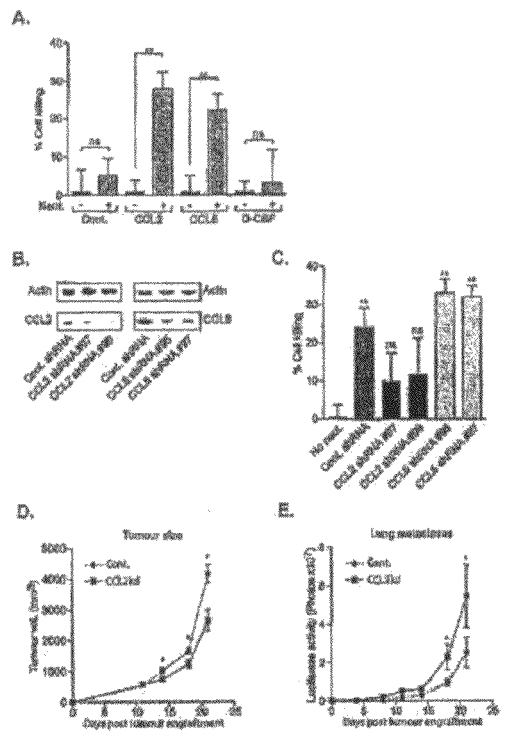
Figures 1, 5:
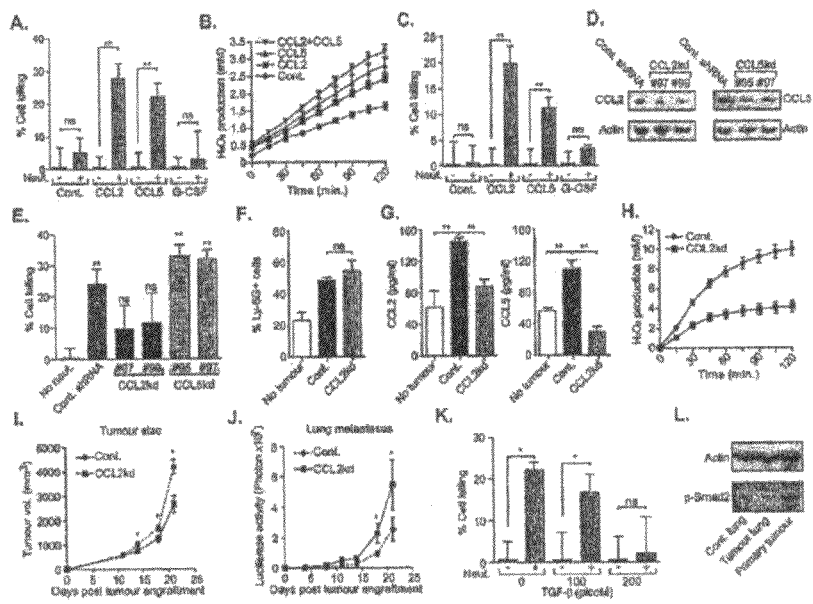

FIG. 5 presents exemplary tumour secreted CCL2 as both required and sufficient for neutrophil entrainment. A. Neutrophils purified from naive mice were co-cultured with 4T1 cells. While naive neutrophils do not kill 4T1 cells, the addition of either CCL2 or CCL5 induces neutrophil mediated cell killing. In contrast, addition of rhG-CSF does not induce neutrophil mediated cell killing, B. CCL2 and CCL5 expression in 4T1 cells transduced with a non-targeting shRNA (cant), CCL2 specific shRNA (#97 and #99), and CCL5 specific shRNA (#95 and #97). C. Mice were orthotopically injected with control, CCL2kd (#97 and #99) and CCL5kd (#95 and #97) 4T1 cells. Neutrophils were purified on day 7 and co-cultured with plated 4T1 cells. While CCL5 knockdown has no effect, loss of CCL2 results in impaired neutrophil induced cell killing. D. Orthotopically injected CCL2kd 4T1 tumours present with growth retardation when compared to control 4T1 tumours. E. CCL2kd tumours have increased spontaneous metastatic potential when compared to control 4T1 tumours.

FIG. 5-1 shows exemplary tumour secreted CCL2 is both required and sufficient for neutrophil entrainment. A. Neutrophils purified from naïve mice were co-cultured with 4T1 cells. While naïve neutrophils do not kill 4T1 cells, the addition of either mCCL2 or mCCL5 induces neutrophil mediated cell killing. In contrast, addition of rhG-CSF does not induce neutrophil mediated cell killing. B. Addition of either CCL2 or CCL5 induces in an increase in $H_2O_2$ production in naïve neutrophils. The presence of both CCL2 and CCL5 has an additive effect on $H_2O_2$ production. C. Neutrophils purified from healthy human volunteers were co-cultured with MDA-MB-231 cells. While naïve neutrophils do not kill MDA-DB-231 cells the addition of both hCCL2 and hCCL5 induces neutrophil mediated cell killing. In contrast, addition of rhG-CSF does not induce neutrophil mediated cell killing. D. CCL2 and CCL5 expression in 4T1 cells transduced with a non-targeting shRNA (cont.), CCL2 specific shRNA (#97 and #99), and CCL5 specific shRNA (#95 and #97). E. Mice were orthotopically injected with control, CCL2kd (#97 and #99) and CCL5kd (#95 and #97) 4T1 cells. Neutrophils were purified on day 7 and co-cultured with plated 4T1 cells. While CCL5 knockdown has no effect, reduced CCL2 levels result in impaired neutrophil induced tumour cell killing. F. FACS analysis of Ly-6G+ neutrophils in the circulation of sham operated mice (no tumour) and mice bearing control (Cont.) or CCL2kd tumours. There is no significant difference between control and CCL2kd tumours in their capacity to mobilize neutrophils. G. Tumour bearing mice (Cont.) have increased circulating levels of CCL2 and CCL5 compared to tumour free mice (no tumour). Mice bearing CCL2kd tumours (CCL2kd) have reduced circulating levels of CCL2 and CCL5 compared to tumour-bearing mice (Cont.). H. The lack of cytotoxic neutrophil entrainment by CCL2kd tumours is manifested in dramatically reduced $H_2O_2$ production compared to TENs entrained by control tumours. I. Orthotopically injected CCL2kd 4T1 tumours present with growth retardation when compared to control 4T1 tumours. J. CCL2kd tumours have increased spontaneous metastatic potential when compared to control 4T1 tumours. K. TGF-β in picomolar concentrations has a dramatic inhibitory effect on TEN mediated in vitro killing of 4T1 cells. L. TGF-β activity in the primary tumour and the lungs as portrayed by phosphorylation of Smad2. Normal lung (Cont. lung) and pre-metastatic lung from tumour-bearing mice (Tumour lung) have very little TGF-β activity (p-Smad2) compared with the primary tumour. (* $p<0.05$, ** $p<0.01$).

Figure 6:
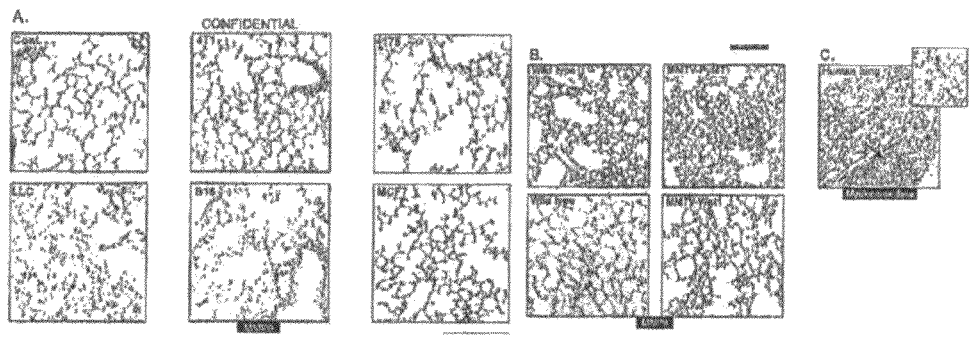

FIG. 6 presents exemplary neutrophils accumulation in the pre-metastatic lung in multiple tumour xenograft and spontaneous murine breast cancer models and in human metastatic lung tissue, A, MMP9 immunohistochemistry on lung tissue from sham-operated (Cont.) and tumor-bearing mice 7 days after orthotopic tumour engraftment. A dramatic increase in MMP9+ cells is visible in the lungs of 4T1 and 4175 tumour-bearing mice (mammary fat-pad) as well as in LLC and B16 (intra-dermal) tumour-bearing mice compared to control, No increase in MMP9+ cells is observed in the lungs of mice orthotopically (mammary fat-pad) injected with MCF7 tumours. B. A dramatic increase in MMP9+ cells is visible in the lungs of mice bearing spontaneous mammary tumours from MMTV-PyMT transgene as well as in mice bearing spontaneous mammary tumours from MM-I-V-Wnt1 transgene compared to control littermates.

C. High levels of myeloperoxidase staining in lung tissue taken form breast cancer patient with lung metastases. The tumor can be seen on the bottom right (arrow).

Figures 1, 7:
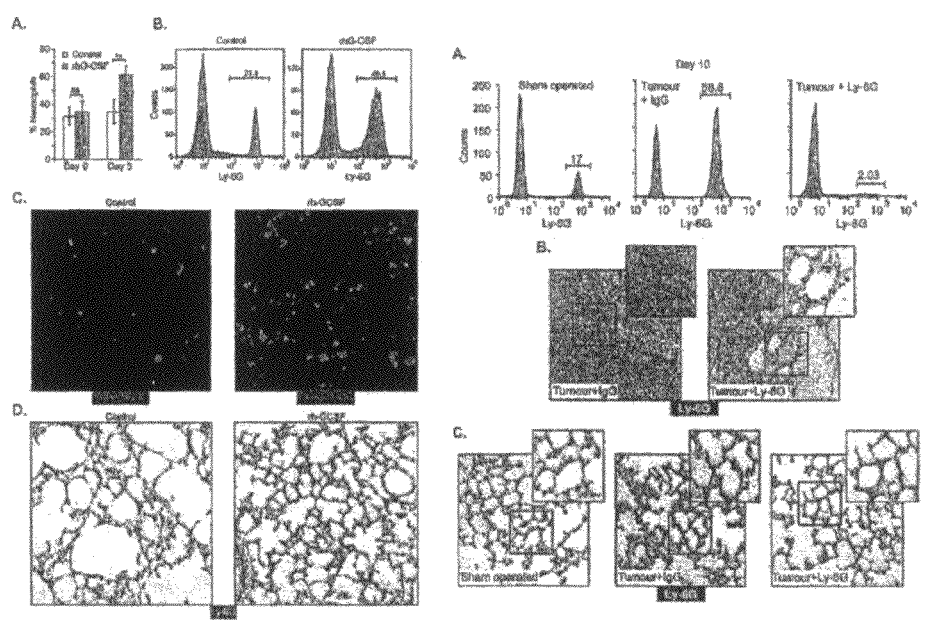

FIG. 7 shows exemplary Ly-6G antibody administration depleted neutrophils from the circulation, the primary tumour and the pre-metastatic lung. A. FACS analysis of Ly-6G+ neutrophils in the circulation on day 10 post tumour engraftment. Tumour-bearing Balb/c mice treated with control IgG (Tumour+IgG) have a dramatic increase in Ly-6G+ neutrophils compared to naive mice. Ly-6G+ neutrophils are depleted in tumour bearing mice treated with Ly-6G antibody (Tumour+Ly-6G). B-C. Ly-6G immunohistochemistry shows that administration of control IgG (Tumour+IgG) has no effect on the accumulation of Ly-6G+ neutrophils in the lungs (compare sham operated and IgG treated tumour bearing mice). Administration of Ly-6G (Tumour+Ly-6G) abolishes the accumulation of neutrophils in the lungs and at the tumour-rim of tumour-bearing mice.

FIG. 7.1 presents exemplary data that rhG-CSF is sufficient for mobilization and lung sequestration of neutrophils, A.

Blood differentials of rhG-CSF and vehicle treated mice showing an increase in circulating neutrophils after 3 days of rhG-CSF administration. (B.) Ly-6G or myeloperoxidase (C,) immunohistochemistry on lung tissue shows that rhG-CSF administration induces an increase in lung-associated neutrophils.

Figure 8:
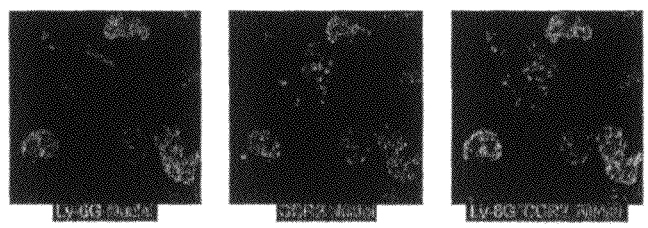

FIG. 8 presents exemplary data for CCR2 expression on lung arrested neutrophils Immunohistochemistry performed on pre-metastatic lungs from 4T1 bearing mice showing co-localization of Ly-6G (green) and CCR2 (red).

Figure 9:
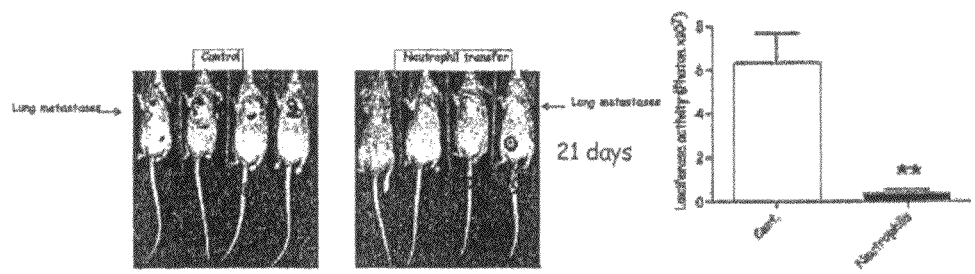

FIG. 9 presents exemplary data on multiple adoptive transfers of TENs nearly cure lung metastases. Exemplary representative images show that multiple infusions of TENs in a host completely attenuate the formation of lung metastases after tail-vein injection of tumor cells. Recipient mouse received TENs transfer at 4, 24, and 48 hours post challenge with tail-vein injection of tumor cells. At 21 days lung metastases were nearly attenuated compared to control infused mouse.

Figure 10:
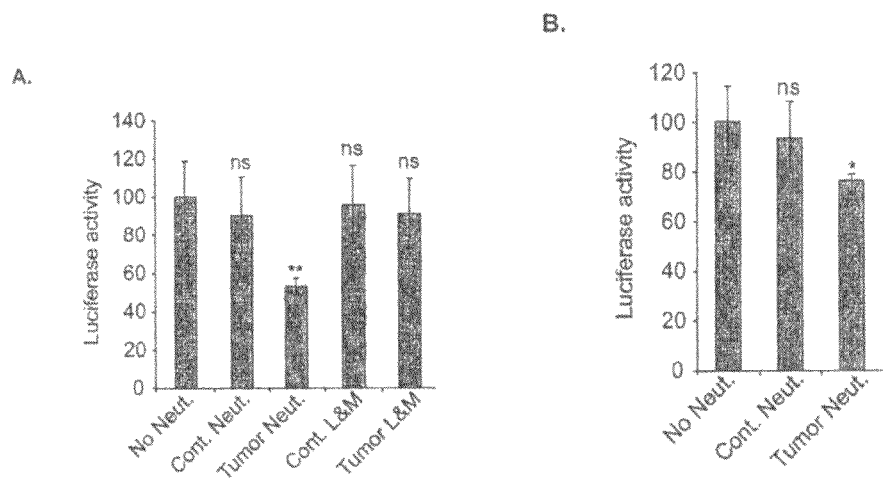

FIG. 10 presents exemplary data on tumor stimulated neutrophils, but not normal neutrophils, normal lymphocytes and monocytes or tumor-stimulated lymphocytes and monocytes, can kill tumor cells in vitro. There is a "cross tumor" training of neutrophils to kill tumor cells. A. Luciferase-labeled 4T1 tumor cells were co-cultured with neutrophils purified from healthy and tumor bearing mice. Cell viability was estimated using a luciferase activity assay. In the presence of neutrophils purified from healthy mice (Cont. Neut.) there is a slight, non-significant reduction in tumor cell viability compared to control 4T1 cultures (No Neut.). Co-culture of 4T1 cell with neutrophils purified from tumor-bearing mice (Tumor Neut.) results in a dramatic reduction in cell viability. Co-culture of 4T1 tumor cells with lymphocytes and monocytes purified from either healthy (Cont. L&M) or tumor-bearing (Tumor L&M) mice does not affect tumor cell viability. B. 4T1 cells were co-cultured with neutrophils from healthy (Cont. Neut.) or B16 melanoma tumor-bearing C57/B6 mice. Again, only a slight reduction in cell viability is observed in the presence of control neutrophils (compare Cont. Neut. to No Neut.) while B16 melanoma entrained neutrophils induce a significant reduction in cell viability (compare Tumor Neut. to No Neut.)

Figure 11:
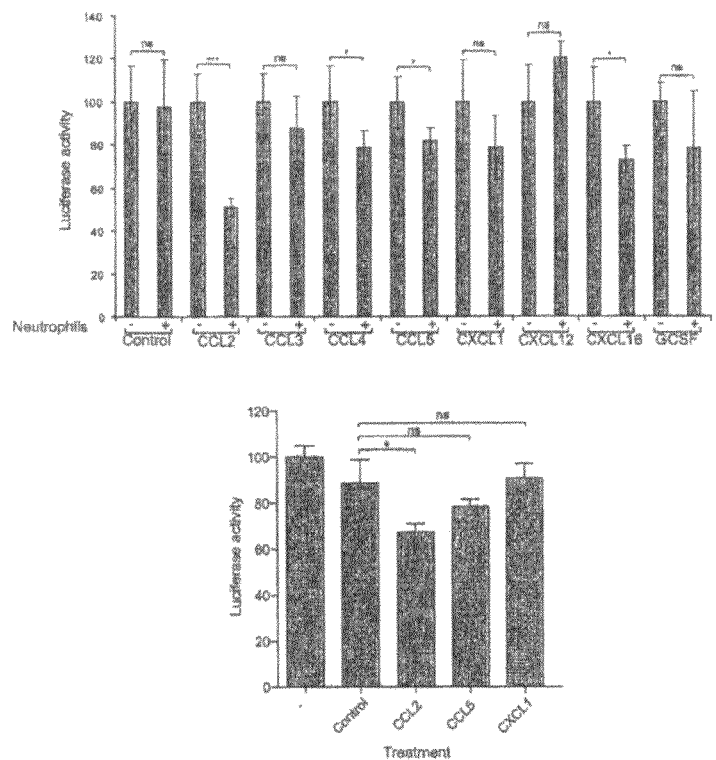

FIG. 11 shows exemplary chemokines for increasing cytotoxicity of mouse naïve neutrophils for killing mouse 4T1 cells (mouse mammary tumor cancer cell line) by reduction luciferase activity in dying cells$_{[p1]}$. A. To test which chemokines may participate in the stimulation of neutrophils, neutrophils purified from healthy mice were co-culture with luciferase labeled 4T1 cells in the presence (20 ng/ml of chemokine) or absence of certain chemokines for an overnight incubation. Of the chemokines capable of inducing a significant reduction in tumor cell viability (CCL2, CCL4, CCL5 and CXCL16), CCL2 has the most dramatic effect. CCL3, CXCL1, CXCL12 and G-CSF had no significant effect on tumor-cell viability. B. To test which chemokines are sufficient for in vivo stimulation of neutrophils healthy mice were treated with G-CSF (to boost neutrophil numbers) and either CCL2, CCL5 or CXCL1. Control mice were treated with G-CSF alone. Neutrophils were purified from these mice and co-cultured with Luciferase-labeled 4T1 cells. G-CSF (Control) and CXCL1 did not significantly stimulate neutrophils and did not induce a reduction in cell viability (compare to 4T1 cell culture without neutrophils (−)). Co-culture of neutrophils purified from mice treated with either CCL2 or CCL5 and 4T1 cells results in a significant reduction in tumor-cell viability. CCL2 was found to be more potent than CCL5 in neutrophil stimulation. Conclusion—CCL2 and to a lesser degree CCL5 can stimulate tumor cell killing both in vitro and in vivo.

Figure 12:
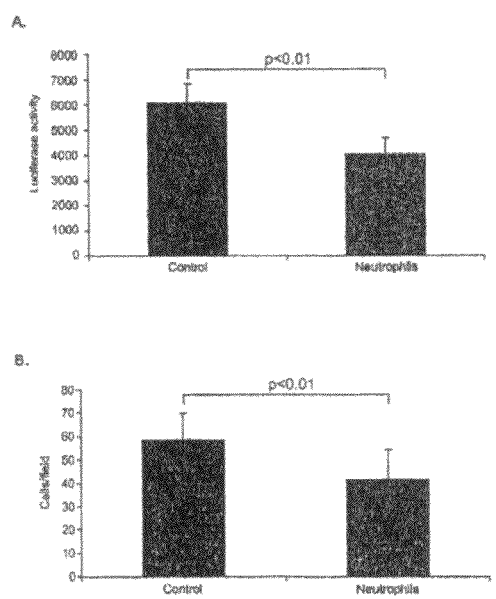

FIG. 12 shows an exemplary comparison of Luciferase activity and actual cell number. A. Luciferase activity (raw numbers) of 4T1 cultured alone (Control) or in co-culture with neutrophils (Neutrophils). B. Measurement of 4T1 cells per field. 4T1 either cultured alone (Control) or in co-culture with neutrophils (Neutrophils).

Figure 13:
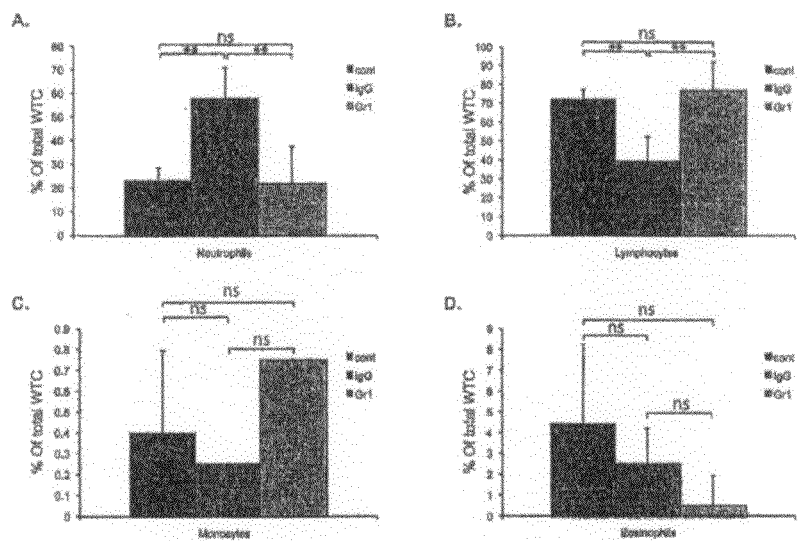

FIG. 13 shows exemplary blood differentials taken on day 10 after tumor inoculation, and 7 days after the beginning of neutrophil depletion treatment. A. Neutrophil counts—tumor bearing mice treated with control antibody (red) have significantly higher neutrophil levels than sham operated mice (blue) or tumor-bearing mice treated with the neutrophil depleting antibody (green). Differences between sham operated mice and neutrophil depleted tumor-bearing mice are not significant B. Lymphocytes tumor bearing mice treated with control antibody (red) have significantly lower neutrophil levels than sham operated mice (blue) or tumor-bearing mice treated with the neutrophil depleting antibody (green). Differences between sham operated mice and neutrophil depleted tumor-bearing mice are not significant. C and D. Although there are differences between the mice groups in the percentage of monocytes and eosinophils they are not significant and consist of few percents (D.) to fractions of a percent (C.). Note scale on C. and D.

Figure 14:
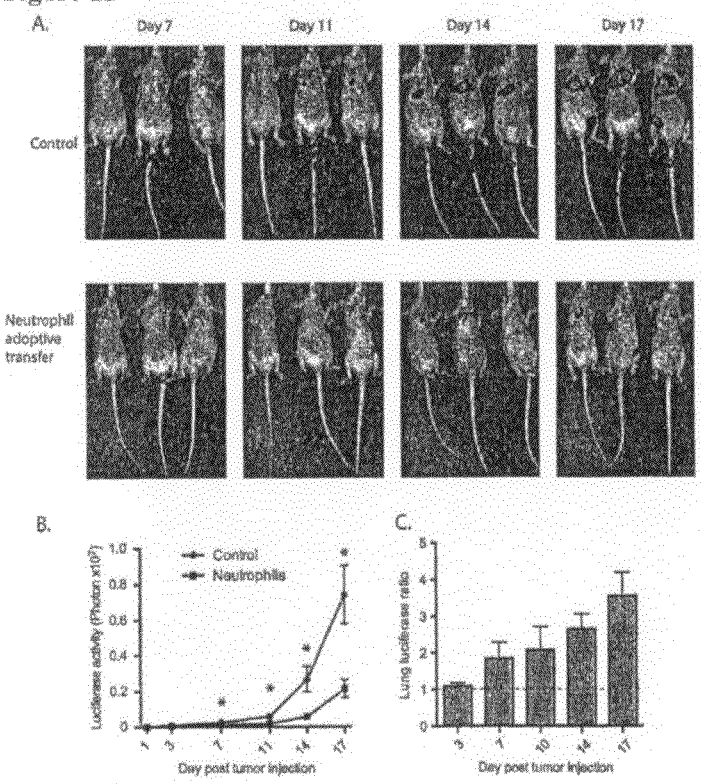

FIG. 14 shows an exemplary neutrophil adoptive transfer experiment. A. All the mice were tail-vein injected with 50,000 luciferase labeled 4T1 cells. 4 hours later, control mice were injected with vehicle (PBS+BSA) and neutrophil-treated mice were injected with 5,000,000 neutrophils purified from tumor bearing mice. Lung metastases were monitored using Luciferase activity emanating from the lungs. B. Quantification of the lung specific Luciferase activity in control and neutrophil treated mice shows that neutrophil transfer delays the formation of lung metastases. C. The average ratios between Luciferase activity emanating from the lungs of control/neutrophil-transfer mice from 3 independent experiments. Increase in ratio indicates are faster progression in metastatic growth.

FIG. 15 shows exemplary in vitro tumor cell killing. In vitro tumor cell killing—there is no significant difference in 4T1 cell number when 4T1 cells are cultured with neutrophils purified from naïve mice (compare Control (−) and (+)). The presence of neutrophils purified from tumor bearing mice (tumor) induces a significant reduction in cell number. In the presence of CCL2 (20 ng/ml), neutrophils from naïve mice gain the ability to kill tumor cells (compare CCL2 (−) and (+)). In the presence of CCL5 (20 ng/ml), neutrophils from naïve mice gain the ability to kill tumor cells (compare CCL5 (−) and (+)). There is no additive effect in combining CCL2 and CCL5 treatments.

FIG. 16 shows exemplary B16-Melanoma TENs (i.e. TENs isolated from mice bearing B16 cancer cells) capable of killing cancer cells. Neutrophils purified from sham-operated or B16 Melanoma-bearing C57/B6 mice were co-cultured with B16 melanoma (A) or 4T1 (B) cells. While control neutrophils had no significant effect on tumor-cell viability, B16-Melanoma TENS gained the capacity to kill both B16 and 4T1 cells in vitro.

FIG. 17 shows exemplary neutrophils purified from control or MMTV-PyMT tumor-bearing mice were co-cultured with 4T1 cells. While control neutrophils had no effect on tumor-cell viability, neutrophils purified from PyMT induced mammary tumor-bearing mice gained the capacity to kill 4T1 cells in vitro.

FIG. 18 shows exemplary attenuation of the formation of lung metastases by transfer of TENs. A. Representative images showing that transfer of TENs attenuates the formation of lung metastases after tail-vein injection of tumor cells. B. Quantification of lung specific luciferase activity shows that TENs significantly delay the formation of lung metastasis. C. Representative images showing that transfer of G-CSF mobilized neutrophils has no effect on the formation of lung metastases after tail-vein injection of tumor cells. D. Quantification of lung specific luciferase activity shows that G-CSF mobilized neutrophils does not delay the formation of lung metastasis. (* $p<0.05$, ** $p<0.01$).

FIG. 19 shows exemplary data on TGF-β inhibition of TEN mediated killing of tumor cells. A. TGF-β in picomolar concentrations has a dramatic inhibitory effect on TEN mediated in vitro killing of 4T1 cells. B. TGF-β activity in the primary tumor and the lungs as portrayed by phosphorylation of Smad2. Normal lung (Cont. lung) and pre-metastatic lung from tumor-bearing mice (Tumor lung) have very little TGF-β activity (p-Smad2) compared with the primary tumor. (* $p<0.05$, ** $p<0.01$).

Figure 20:
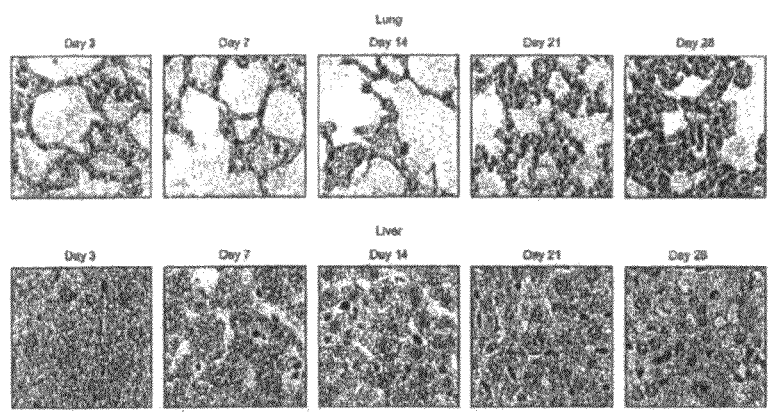

FIG. 20 shows an exemplary embodiment demonstrating neutrophil accumulation in the lung and liver of 4T1 tumor-bearing mice. Nude female mice were orthotopically injected with 4T1 cells into the mammary fat pad. Lung and liver tissues were taken on day 3, 7, 14, 21 and 28 post tumour engraftment and stained with Ly-6G to detect neutrophils. Neutrophils start accumulating in the lungs as early as day 7 post tumour engraftment. Neutrophils start accumulating in the liver in low numbers starting on day 14.

Figure 21:
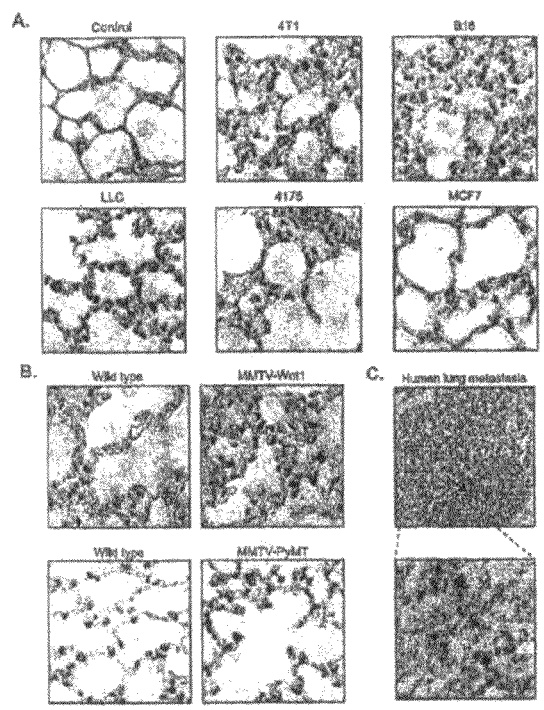

FIG. 21 shows an exemplary embodiment demonstrating that neutrophils accumulate in the pre-metastatic lung in multiple tumour xenografts, in a spontaneous murine breast cancer model and in human metastatic lung tissue. A. Ly-6G immunohistochemistry on lung tissue from sham-operated (Control) and tumour-bearing mice 7 days after orthotopic tumour engraftment. As early as 7 days post tumour engraftment, a dramatic increase in Ly-6G$^+$ cells is visible in the lungs of 4T1 and 4175 tumour-bearing mice (mammary fat-pad) as well as in LLC and B16 (intra-dermal) tumour-bearing mice compared to control. No increase in Ly-6G$^+$ cells is observed in the lungs of mice orthotopically (mammary fat-pad) injected with MCF7 tumours as late as 30 days post tumour engraftment. B. MMTV-Wntl and MMTV-PyMT female mice were sacrificed as soon as a tumour was palpable (approx. 6 and 3 months old for MMTV-Wntl and MMTV-PyMT mice respectively). A dramatic increase in Ly-6G$^+$ cells is visible in the pre-metastatic lungs of mice bearing spontaneous mammary tumours driven by MMTV-Wntl or MMTV-PyMT transgene compared to wild type littermates. C. High levels of myeloperoxidase staining in lung tissue taken from breast cancer patient with lung metastases. The tumour is shown on the bottom right (arrow).

Figure 22:
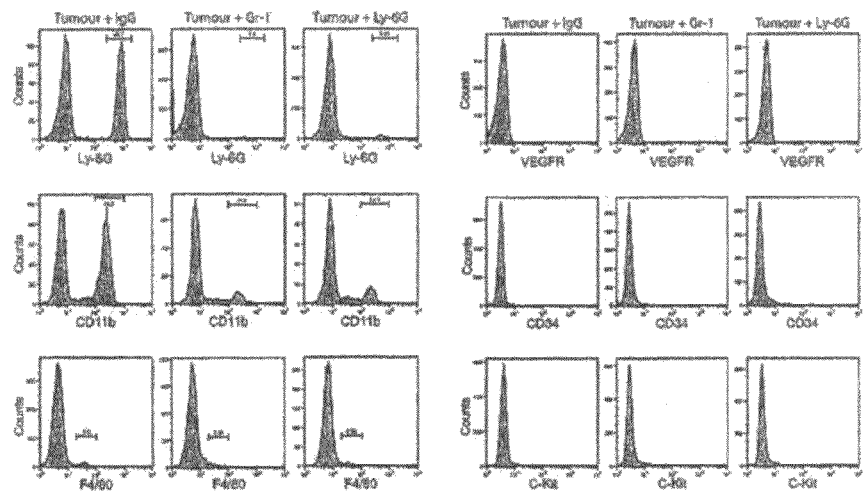

FIG. 22 shows an exemplary embodiment demonstrating a FACS profile of circulating bone marrow derived cells in neutrophil depleted tumour bearing mice. Peripheral blood FACS profile of circulating Ly-6G+, CD11b+, VEGFR+, CD34+ and C-Kit+ cells in day 10 4T1 tumour bearing mice treated with either control antibody (IgG) or neutrophil depleting antibodies (Gr-1 or Ly-6G). Both Gr-1 and Ly-60 efficiently deplete Ly-6G neutrophils. Since neutrophils are CD11b+, the decrease in neutrophil numbers following Gr-1 or Ly-6G administration is also manifested in a dramatic decrease in CD11b+ cells. There was no significant change in F4/80+, VEGFR+, CD34+ or C-Kit+ cell populations detected in the circulation in any of the conditions tested.

Figure 23:
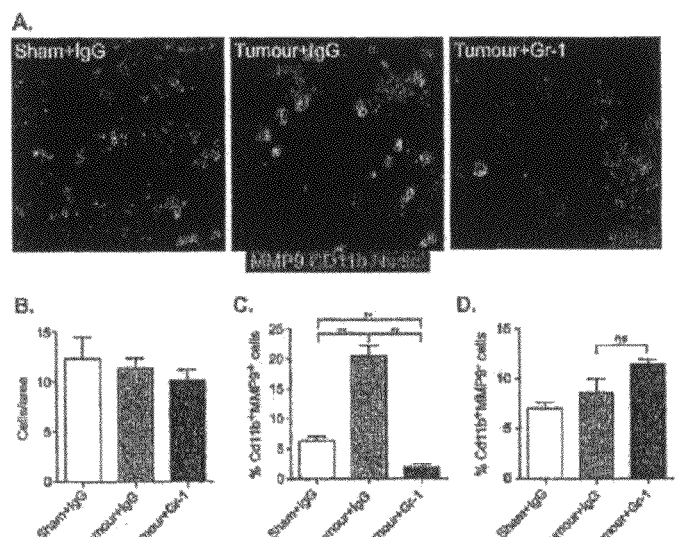

FIG. 23 shows an exemplary embodiment demonstrating that neutrophil depletion has no effect on non-neutrophil leukocytes in the lung.

A. Co-staining of MMP9 (red, neutrophils) and CD11b (green, total leukocytes) on lung tissue from sham operated (Sham+IgG), tumour-bearing mice (Tumour+IgG) and neutrophil-depleted tumour-bearing mice (Tumour+Gr-1). B. There are no significant changes in the total number of cells per lung area in any of the mice. C. Tumour-bearing mice show a dramatic increase in CD11b+MMP9+ cells (neutrophils) in the lungs compared to control. Gr-1 treatment results in a dramatic decrease in CD11b-MMP9+ cells compared to both tumour bearing and control mice. D. There is no significant difference in the CD11b+MMP9– cell population between IgG treated tumour bearing mice (Tumour+IgG) and neutrophil depleted tumour bearing mice (Tumour+Gr-1). (** $p<0.01$).

FIG. 24 shows an exemplary embodiment demonstrating neutrophil depletion has no significant effect on apoptosis at the primary site.

The rate of apoptosis in day 10 4T1 primary tumours from control (IgG) and neutrophil depleted (Gr-1) mice was assessed by immunohistochemical staining for Cleaved Caspase 3. The extent of apoptosis was very low in both control and neutrophil depleted mice as can be the quantification of Cleaved Caspase 3 positive cells per tumour area (A.). B. Representative images showing Cleaved Caspase 3 staining in day 10 tumours from control (IgG) and neutrophil depleted (Gr-1) mice.

FIG. 25 shows an exemplary embodiment to test whether neutrophils can be entrained by tissue injury neutrophils were purified from control (A.) and mice that had a 4 mm in diameter dorsal area of skin surgically removed (B.). C. Co-culture of neutrophils from either injured (Tissue injury) or uninjured (Control) mice showed no significant cytotoxic effect on cultured 4T1 cells. Moreover, neutrophils purified from injured mice provide a pro-survival effect on cultured 4T1 cells.

FIG. 26 shows exemplary chemokines for increasing cytotoxicity of human naïve neutrophils for killing MDA-MB-231 cells (human breast cancer cell line). Luciferase is under a constitutive promoter so cell death results in a decrease in luciferase activity because there is no transcription/translation of the lucierferase gene. The assay itself requires lysing of the cell to release the luciferase to mix with the luciferin and measure the luminescence. But it isn't that they dying cell releases luciferase. More signal means more luciferase which means more live cells. by release of luciferase from dying cells. Multiple chemokines were found to have the capacity to induce cytotoxicity in human neutrophils at 100 ng/ml in an overnight incubation (contacting). Nave human neutrophils were co-cultured with MDA-MB-231 cells. While naïve neutrophils do not kill MDA-DB-231 cells the addition of certain CC and CXC human chemokines induced neutrophil mediated cell killing, see * and ** indicating significant cell death. CCL2, CCL3 and CCL5 but not CCL4 significantly increased neutrophil cytotoxicity. Similarly, SDF1 (CXCL12), CXCL16 and to a lesser extent CXCL1 significantly increased neutrophil cytotoxicity. Cells were seeded at a ratio of human neutrophils:human tumor cells=1:1.

DETAILED DESCRIPTION OF THE INVENTION

The present invention relates generally to compositions and methods for treating cancer patients with a poor prognosis, and to therapeutic modalities for improving prognosis by combating metastasis and abrogating chemoresistance in cancer cells. In particular, the invention relates to the role of white blood cells, i.e. neutrophils and neutrophil-like cells, in preventing the spread of cancer from a primary tumor to secondary locations in the body. The invention provides methods for reducing or delaying the spread of metastatic cancer cells in a patient at risk for metastatic tumor development, at risk for metastatic relapse, i.e. prophylactic methods, and treating patients suffering from metastatic tumors.

An object of the present invention is the therapeutic use of TENs to treat metastatic and/or micrometastic disease in a cancer patient who is at risk for metastatic relapse and/or is suffering from metastatic disease. Another object of the present invention is the method to produce anti-metastatic TENs suitable for such therapeutic use.

In an attempt to further understand the relationship between the primary tumor site and formation of the pre-metastatic niche, a breast cancer mouse model was used. Following establishment of a primary tumor in the mouse, multiple metastatic niches were examined to determine changes in gene expression profiles, infiltration of immune cells, and formation of metastases. It was found that the presence of a primary tumor promoted the infiltration of cytotoxic neutrophils into the metastatic niche and inhibited the progression of metastatic disease. CCL2, CCL5, CXCL6, CXCL12 and the like, secreted by the primary tumor were the factors responsible for the "entrainment" and anti-metastatic activity of the cytotoxic neutrophils. The cytotoxic activity of the neutrophils was found to be mediated by the generation of reactive oxygen species produced by the NAPDH Oxidase complex.

Furthermore, it was also found that the primary tumor altered the gene expression of the pre-metastatic niche; these differentially expressed genes can be used as therapeutic targets to disrupt the formation of the pre-metastatic niche and can be exploited as an additional anti-metastatic treatment option.

If a patient is determined to be at risk for metastatic relapse, the patient's neutrophils are isolated from the blood or bone marrow by any technique known to one skilled in the art, such as dextran sedimentation, differential centrifugation, FACS, or antibody depletion, etc. Alternatively, neutrophils or neutrophil-like cells (collectively referred to herein as neutrophils) can also be obtained from any other appropriate source know to one skilled in the art such as a donor or artificial sources such as via tissue engineering etc. If required, the isolated neutrophils can be expanded ex vivo with an appropriate chemokine such as GM-CSF or G-CSF, etc. Once isolated and/or obtained, and expanded if necessary, the neutrophils are entrained ex vivo with stimulatory, chemokines and/or cytokines, such as CCL2 or CCL5, etc. Any immune stimulatory agent shown to induce a TENs-like phenotype is sufficient for entrainment. The cytotoxic activity of these TENs can be further augmented by the activation of the NAPDH oxidase complex by known complex stimulators such as TNF, LPS, or fMLP, etc. or any other stimulatory agent shown to induce a TENs-like phenotype. It is also possible to use the TENs as a gene therapy vehicle for introducing anti-metastatic gene therapy to the metastatic niche; any anti-metastatic gene therapy known to one skilled in the art will be sufficient. Prior to TENs reintroduction, the primary tumor of the patient can be treated with the appropriate standard of care, such as surgical resection, ablation, chemotherapy, etc.

Another object of the present invention is the identification of therapeutic targets within the pre-metastatic niche. The primary tumor causes gene expression profile changes at distant metastatic sites. Genes that are mis-regulated at the pre-metastatic site will be critical for the establishment and maintenance of an environment conducive to the seeding and outgrowth of metastatic lesions.

Therapeutically targeting these mis-regulated genes by any method known to one skilled in the art, such as small molecule inhibition, RNAi, shRNA, antibody, biologics, etc. will disrupt the metastatic niche rendering it inhospitable for the formation of metastases. The combined use of TENs with such therapeutic agents will have increased potency in combating the progression of metastasis.

It is contemplated that the present invention can be used to treat metastases arising from any tumor of origin including breast, melanoma, lung, colon, prostate, kidney, pancreas, cervical, etc. Furthermore, it is also contemplated that the present invention can be used to treat metastases at any metastatic site including lung, bone, brain, liver, etc. The treatment method disclosed herein can be used to treat patients with established metastatic disease as well as a preventative treatment to block metastases formation in at risk patients who have yet to develop detectable metastases; the cytotoxic activity of the TENS is capable of killing any established metastases as well as preventing the formation of any new metastases.

A leading cause of cancer related mortality is metastatic spread of tumour cells to distant sites. The location of these sites varies considerably among different primary tumour types. Several studies have shown that the site of metastasis may be determined by a specific gene expression pattern, or signature, in primary tumour cells that mediates metastasis to specific distant organs, Gupta, et al. *Cell* 127:679-695 (2006), herein incorporated by reference. On the other hand, tumour induced changes in the microenvironment of distal organs prior to colonization might make certain tissues more receptive for colonization by migrating tumour cells, Pekarek, et al. *J Exp Med* 181:435-440 (1995), herein incorporated by reference. Recent studies have suggested that factors secreted from the primary tumour may modulate the future site of metastasis in a directed fashion Erler, et al. Cancer Cell 15:35-44 (2009), Kaplan, et al. Nature 438:820-827 (2005), herein incorporated by reference. Primary tumours were shown to prepare distal organs for later colonization of metastatic cells by stimulating organ specific infiltration of bone marrow derived cells, Erler, et al. Cancer Cell 15:35-44 (2009), Hiratsuka, et al. Nat Cell Biol 8:1369-1375 (2006), Kaplan, et al. Nature 438:820-827 (2005), herein incorporated by reference.

Although treatments, including chemotherapy, are considered successful for treating tumor growth, many types of metastatic cancers are resistant to known therapies. One example is breast cancer, in particular, triple negative breast cancer. Breast cancer is considered triple negative when three specific markers are not present: in other words, these tumor cells do not have receptors for the hormones estrogen and progesterone, or for the protein human epidermal growth factor (HER2). These receptors and proteins typically contribute to the growth of other types of cancer cells and can occur in any combination. These receptors receive signals from hormones to grow, and the tumors grow at an abnormal rate making these receptors targets for new drugs on the market, including Herceptin, which is boosting survival rates in women with the HBR2 type of cancer.

When a patient is negative for all three markers, there are no special targets for treatment. That leaves traditional methods of surgery, radiation and chemotherapy drugs for triple negative patients, however this type of cancer frequently spreads to other organs. A 2007 study published in the journal Cancer of women with all stages of breast cancer found that 77 percent of triple-negative patients survived at least five years, compared with 93 percent of women with other types of breast cancer.

Thus, "triple negative" breast cancer, refers to an aggressive form of breast cancer which is impervious to both standard and new treatments includig chemotherapy. Triple negative breast cancer is found disproportionately in younger women and African American people.

As with all cancers, statistics are worse for those whose breast cancer has spread to other organs. The median survival for a triple-negative patient with metastasized cancer is about 13 to 14 months. Median survival for those with other types of breast cancer is two to three years, Dr. Katherine H. Rak Tkaczuk, professor of medicine and director of the University of Maryland cancer center's breast evaluation and treatment program, Cohn, The Baltimore Sun, Oct. 2, 2010, Page 2 of 5, herein incorporated by reference.

One drug being tested is Avastin, which has sparked some controversy because it has not been shown to extend life for those with advanced breast cancer and has serious side effects. Therefore new therapies are needed to inhibit, i.e. slow the rate of metastatic cancer development over time, for cancer such as triple negative breast cancer in addition to other types such as colon cancer, etc.

I. Anti-Metastatic Therapy

Targeted Neutrophil Therapeutic

In some embodiments, the present invention provides therapies for slowing or completely inhibiting metastatic cancer (e.g., breast cancer, and in particular triple negative breast cancer). In a preferred embodiment, personal therapies are provided wherein a patient provides white blood cells of the present inventions for contact with entraining formulations ex vivo for injection of said contacted white blood cells, without entraining chemokines, into that patient.

A method of treatment for using a personal therapy comprising administration of a patient's own neutrophils is contemplated herein. This treatment targets tumor cells that have the potential to metastasize and form metastatic cancer. A successful treatment will result in reduced spreading of the tumor to distant tissues. One example of a measure of this success is a patient who does not develop metastatic cancer within 3 months of TENs administration of their own entrained neutrophils, with or without contact with an entraining formulation prior to administration, i.e. a TENs therapy. In another embodiment, a patient may not develop metastatic cancer within 6 months of TENs therapy. In another embodiment, a patient may not develop metastatic cancer within 1 year of TENs therapy.

Treatment methods described herein are contemplated for use as both prophylactic and therapeutic and may therefore be used prior to chemotherapy, after chemotherapy or to concurrently to supplement chemotherapy.

Multiple treatments are contemplated to have an additive beneficial effect (i.e. prevention of metastatic cancer) over years following tumor resection. Patients diagnosed with cancer are routinely followed in the years following diagnosis and initial therapy. This is done for the exact purpose of detecting tumor recurrence and spread to distant organs. Patients at risk for recurrence receiving standard adjuvant therapies will be compared to patients receiving adjuvant therapies plus entrained neutrophils in a prospective, double-blind study to determine the effectiveness of the therapies and methods described herein.

Neutrophil cells are found in the circulation and thus can be isolated from blood samples at any given time during the life of a patient. Thus, in one embodiment, a patient at risk for metastatic cancer is provided with their own TENs at least once every 3 years following tumor resection. In another embodiment, a patient at risk for metastatic cancer is provided with their own TENs at least once every 3 months, at least once every year, at least once every 2 years, at least once every 3 years, following tumor resection. In some embodiments, at the time of tumor excision, tissue/cell samples are frozen and stored to provide tumor cells to add to entrainment formulations months and years after the primary tumor was removed from a patient.

Specifically, methods of the present inventions are described herein. Whole blood was obtained from a subject for providing neutrophils of the present inventions. For experiments comprising human neutrophils, human white blood cells were separated from red blood cells by several methods, including, sedimentation of heparanized whole blood by dextran sedimentation, Ficoll density gradient centrifugation (Histopaque-1077; Sigma) (Kjeldsen, Subcellular fractionation of human neutrophils on Percoll density gradients, Journal of Immunological Methods. 232(1-2):17 pages 131-143, herein incorporated by reference) and hypotonic lysis of red blood cells in the neutrophil-rich pellet. Neutrophil purification was achieved using an inert density gradient. Purity of isolated neutrophils are determined using manual differential counts. Healthy patients are estimated to yield 1 million neutrophils per mL of venous blood.

Isolated neutrophils were cultured in suspension in commercial media (RPMI) supplemented with 2% Fetal Calf Serum (FCS) for exemplary cytotoxic neutrophils obtained here. In other embodiments, the use of endotoxin free (FCS) is contemplated for use in medium formulations. Alternatively, a serum free medium is contemplated for use. For patient administration, i.e. innoculations, of their own cultured TENS with or without contact with an entraining formulation, culture reagents are contemplated for use which were pre-tested for major pathogens, as is standard practice in human clinical trials. Exemplary reagents are commercially available form multiple vendors, such as Invitrogen, Sigma and the like. Thus media and supplements will be tested for toxins and/or contamination prior to neutrophil purification and entrainment. For example, endotoxin/contamination test kits giving very quick results (15 minutes) are commercially available from multiple vendors (such as Lonza).

When an entraining formulation is used, it will be added immediately after neutrophil purification. The entrainment, i.e. contact with the entraining formulation, will take place while cells are in suspension cultures, i.e. contained in vials. In one embodiment, neutrophil entrainment will be done in a co-culture of naïve neutrophils in the presence or absence of entraining chemokines. In one embodiment, neutrophil entrainment will be done in a co-culture of naïve neutrophils in combination with tumor cells and entraining chemokines. Neutrophils were exposed to the entraining agent for 18-24 hours for experiments described herein. In other embodiments, neutrophil entrainment may range from 2-18 hours. In other embodiments, neutrophil entrainment may range from 2-12 hours. Following entrainment the cells are ready for injection. Neutrophil containing vials will then be centrifuged for 5 minutes (400 g) to recover the entrained neutrophils. Prior to use, either in vitro or in vivo, the cells will be washed to remove entraining agents. After centrifugation, in some embodiments, neutrophils will be administered to a patient, i.e. injected, into the patient. In other embodiments, TENs contacted with an entraining formulation will be used in experiments for testing cytotoxicity, for examples, see experiments described herein.

In other embodiments, it is contemplated that neutrophils may be derived from hematopoietic stem cells. These stem cells may be stored as frozen samples long term, i.e. at least one or more years, for additional treatments.

In one embodiment, 10 mls of whole blood are obtained from a human patient for providing human TENs of the present inventions. For example, from a 10 ml blood sample, 20,000,000 to 30,000,000 neutrophil cells were isolated/purified. In one embodiment, larger amounts of blood samples would be used to provide a significantly higher number of neutrophils. In other embodiments, patients would be treated with neutrophil stimulating agents for providing higher numbers of neutrophils in 10 mls of blood. Since neutrophils in 10 mls of blood from a subject with cancer are cytotoxic in vitro after contact with an entraining formulation of the present inventions, these cells are contemplated to provide anti metastatic protection in vivo. Thus it is contemplated that in one embodiment, 20,000,000 to 30,000,000 neutrophils isolated from a patient at risk of metastatic cancer are capable of providing antimetastatic effects following contact with an entrainment formulation of the present inventions, i.e. cytotoxic neutrophils capable of reducing metastatic cancer. In other embodiments, higher numbers of isolated TENs are contemplated for entrainment and use. In further embodiments, early phase clinical trials are contemplated for use in determining the number of isolated neutrophils that would provide antimetastatic effects of administering TENs of the present inventions.

In other examples using mice, neutrophils were identified with several markers, such as Gr-1 antibodies, Ly-6G antibodies, and the like. Gr-1 consists of antibodies identifying two epitopes—Ly-6G and Ly-6C. While Ly-6G is neutrophil specific, Ly-6C is also expressed by a subset of monocytes. To exclude the possibility that cells other than neutrophils are involved in this process, the Gr-1 antibody experiments were repeated with the neutrophil specific Ly-6G antibody. Similar results were obtained with each of these antibodies indicating that the anti-metastatic cytotoxic response was mediated by neutrophils.

In mouse experiments (in vivo) an excess of 250 isolated neutrophils were administered per injected tumor cell. The inventors contemplate that a micrometastatic tumor consists of about 100 tumor cells, thus a minimum number of neutrophils is estimated about 25,000 TENs for the therapy described herein to be successful.

In in vitro studies described herein, showed that a ratio of 1:1 (cancer/tumor cell to TEN) was sufficient for killing of up 50% of the human tumor cells by the entrained human neutrophils contacted with an entraining formulation of the present inventions. In mice, a ratio of 100:1 TENs:cancer cells showed similar cytotoxic effects.

The in vitro experiments described herein, were done with purified neutrophils of the present inventions. Further, the inventors discovered that neutrophils purified from breast cancer patients, but not from healthy volunteers, had significant cytotoxicity towards human cancer cells. Thus, although mouse and human immunological cell types are known to have different subtypes, the cytotoxicity capability of white blood cells in the neutrophil layers isolated from both mice and humans show similar cancer/tumor cell killing effects.

II. Entraining Formulations, i.e. Ex Vivo Contacting with Chemokines

In preferred embodiments, an agent capable of providing TENs with increased cytotoxic activity towards tumor cells is contemplated for use, such as CCL2.

In one embodiment, CCL2 is added to an entraining formulation at a concentration of 100 ng/ml. In other embodiments, CCL2 is added to an entraining formulation at a concentration ranging from 20-500 ng/ml. In one embodiment, CCL2 is a full-length recombinant CCL2 polypeptide. In other embodiments, CCL2 comprises a portion of a recombinant CCL2 polypeptide capable of providing cytotoxic neutrophils of the present inventions. In a preferred embodiment, the CCL2 polypeptide is a copy of a human CCL2 polypeptide encoded by a copy of a human CCL2 gene.

In some embodiments, CCL3 is added to an entraining formulation at a concentration of 100 ng/ml. In other embodiments, CCL3 is added to an entraining formulation at a concentration ranging from 20-500 ng/ml. In one embodiment, CCL3 is a full-length recombinant CCL35 polypeptide. In other embodiments, CCL3 comprises a portion of a recombinant CCL3 polypeptide capable of providing cytotoxic neutrophils of the present inventions. In a preferred embodiment, the CCL3 polypeptide is a copy of a human CCL3 polypeptide encoded by a copy of a human CCL3 gene.

In some embodiments, CCL5 is added to an entraining formulation at a concentration of 100 ng/ml. In other embodiments, CCL5 is added to an entraining formulation at a concentration ranging from 20-500 ng/ml. In one embodiment, CCL5 is a full-length recombinant CCL5 polypeptide. In other embodiments, CCL5 comprises a portion of a recombinant CCL5 polypeptide capable of providing cytotoxic neutrophils of the present inventions. In a preferred embodiment, the CCL5 polypeptide is a copy of a human CCL5 polypeptide encoded by a copy of a human CCL5 gene.

CXC chemokines were also discovered to increase cytotoxic human neutrophil killing of target human cancer cells.

In some embodiments, CXCL1 is added to an entraining formulation at a concentration of 100 ng/ml. In other embodiments, CXCL1 is added to an entraining formulation at a concentration ranging from 20-500 ng/ml. In one embodiment, CXCL1 is a full-length recombinant CXCL1 polypeptide. In other embodiments, CXCL1 comprises a portion of a recombinant CXCL1 polypeptide capable of providing cytotoxic neutrophils of the present inventions. In a preferred embodiment, the CXCL1 polypeptide is a copy of a human CXCL1 polypeptide encoded by a copy of a human CXCL1 gene.

In some embodiments, CXCL6 is added to an entraining formulation at a concentration of 100 ng/ml. In other embodiments, CXCL6 is added to an entraining formulation at a concentration ranging from 20-500 ng/ml. In one embodiment, CXCL6 is a full-length recombinant CXCL6 polypeptide. In other embodiments, CXCL6 comprises a portion of a recombinant CXCL6 polypeptide capable of providing cytotoxic neutrophils of the present inventions. In a preferred embodiment, the CXCL6 polypeptide is a copy of a human CXCL6 polypeptide encoded by a copy of a human CXCL6 gene.

In some embodiments, CXCL12 is added to an entraining formulation at a concentration of 100 ng/ml. In other embodiments, CXCL12 is added to an entraining formulation at a concentration ranging from 20-500 ng/ml. In one embodiment, CXCL12 is a full-length recombinant CXCL12 polypeptide. In other embodiments, CXCL12 comprises a portion of a recombinant CXCL12 polypeptide capable of providing cytotoxic neutrophils of the present inventions. In a preferred embodiment, the CXCL12 polypeptide is a copy of a human CXCL12 polypeptide encoded by a copy of a human CXCL12 gene.

In another embodiment, a TGFbeta inhibitor is added to an entraining formulation prior to contacting an entrained neutrophil at a concentration wherein TGFbeta signaling is inhibited in the neutrophil. Inhibition of TGFbeta signaling will be determined by measuring function of downstream effectors proteins, such as Smad2 phosphorylation amounts or rates. In one embodiment, phosphorylation of SMAD (small mother against Decapentaplegic) protein is measurement of TGFbeta activity, see also Methods in Molecular Biology (2007) V 142: Transforming Growth Factor-Beta Protocols, herein incorporated by reference, for other potential assays. In another embodiment, a TGFbeta inhibitor is added to the entraining formulation at a concentration wherein cytotoxic activity, of the entrained neutrophils is increased over neutrophils contacted with an entraining formulation without a TGFbeta inhibitor. In one embodiment, addition of a TGFbeta inhibitor to the entraining formulation would increase cytotoxicity activity of neutrophils. For example a TGFbeta inhibitor SB431542 (Tocris) is added at IC50=94 nM. In other embodiments, amounts up to 10 fold higher concentrations will be added for increasing antitumor activity of isolated neutrophils.

The inventors contemplate increasing the number of entrained neutrophils isolated from patients, such that an agent for increasing neutrophil numbers in vivo is administered to a subject prior to isolation of neutrophils. Standard methods comprising known agents, such as G-CSF, are contemplated for use in methods described herein. For example, G-CSF, such as in Filgrastim/NEUPOGEN®, will be administered according to the Prescribing Information provided by AMGEN (Thousand Oaks, Calif.). As one example, G-CSF in the dose range of 1 to 70 mcg/kg/day would be administered by intravenous (IV) injection or continuous subcutaneous (SC) infusion prior to isolation of neutrophils.

III. Compositions and Methods

The 4T1 murine mammary tumour model was employed to gain insight into the early transcriptional changes that take place in the pre-metastatic lung. Orthotopically implanted 4T1 tumours spontaneously metastasize primarily to the lung whereas metastases to the liver, brain, and bones are less frequent and arise much later (FIG. 1A). In order to account for the effects of the surgical procedure mRNA microarray analysis was preformed on lung and liver samples from sham-operated versus tumour-bearing mice. No significant differences were found in gene expression 3 days after tumour engraftment. In contrast, the expression of 325 and 912 genes was significantly changed in the lung and liver (respectively) of tumour-bearing mice 7 days after tumour engraftment (FIG. 1B). Of the 325 genes significantly changed in the lung, 293 were lung specific and were not changed in the liver. Only a small number of tumour cells (<10) were found in the lungs or the liver at this point suggesting that tumour-cell contribution to the expression array is negligible (FIG. 1C, lower graph).

Several neutrophil-specific genes (such as cathelicidin and lactoferrin) are acutely upregulated in the pre-metastatic lung but not in the liver (FIG. 1D) suggesting that neutrophils are recruited to the pre-metastatic lung. This hypothesis was confirmed by immunohistological staining with the neutrophil specific antibody Ly-6G showing a dramatic increase in Ly-6G+ neutrophils in the lung by day 7 post tumour engraftment (FIG. 1E). Further immunohistochemical analysis was performed on pre-metastatic lung tissue to test whether acutely upregulated genes co-localize with neutrophils. As can be seen in FIG. 2B, MMP9 (upregulated 45-fold) co-localizes with the neutrophil marker Ly-6G but not with the pan macrophage marker F4/80. Further analyses show that $MMP9^+$ cells in the pre-metastatic lung co-stain with other neutrophil markers such as myeloperoxidase and cathelicidin. Neutrophils continue to accumulate in the lungs with time and start accumulating in the liver on day 14 post tumour engraftment (FIG. 20).

The increase in lung neutrophils was also found in athymic mice bearing other pre-metastatic xenografts as well as in MMTV-Wnt1 and MMTV-PyMT driven spontaneous mammary tumours in immunocompetent mice (FIG. 21). Interestingly, there was no increase in Ly-6G staining in mice with orthotopic MCF7 tumours, which are not metastatic. Lung tissue taken from human breast cancer patients with lung metastases show high levels of myeloperoxidase staining (in 5/5 cases examined) suggesting that neutrophil recruitment to the lungs is also relevant in human breast cancer (FIG. 21C).

Neutrophils have been implicated in pro-tumourigenic processes (Pekarek, et al., J Exp Med 181:435-440 (1995), Shojaei, et al., Nature 450:825-831 (2007), herein incorporated by reference) and $CD11b^+$ bone marrow derived cells were shown to take part in the priming of the pre-metastatic lung and enhance the seeding of circulating tumour cells (Erler, et al., Cancer Cell 15:35-44 (2009), Yan, et al., Cancer Res 70:6139-6149 (2010), herein incorporated by reference). In order to determine the role of neutrophils in the lung pre-metastatic site, the ability to efficiently deplete neutrophils in tumour bearing animals was established. Balb/c mice were orthotopically injected with 4T1 cells to generate a primary tumour and were then treated with either control (IgG) or the neutrophil depleting antibody Ly-6G starting on day 3 post tumour engraftment. Control mice were sham-operated (no tumour) and treated with the control antibody (IgG). Tumour-bearing mice treated with the neutrophil depleting Ly-6G antibody show dramatic and specific reduction in neutrophil numbers in the circulation (FIGS. 7-1A and 22), the primary tumour-rim and the lungs (FIG. 7-1B-C). Further analysis of lung associated CD11b+ cells shows a significant increase in CD11b+MMP9+ cells (which are neutrophils, note Ly-6G-MMP9 colocalization FIG. 2B) in the lungs of tumour-bearing mice (FIG. 23) compared with sham-operated mice. Upon neutrophil depletion there is a dramatic reduction in lung associated CD11b+MMP9+ cells (neutrophils) but no significant effect on the CD11b+MMP9− population (FIG. 23D). This observation suggests that lung associated CD11b+ cell populations, other than neutrophils, are not dramatically affected by neutrophil depletion.

The long-term effects of neutrophil depletion on spontaneous metastasis from the mammary fat pad were tested as one exemplary method for determining inhibition of metastasis. Neutrophil depletion in the circulation was highly effective until day 14 post tumour engraftment after which neutrophil levels were not significantly different in control or neutrophil depleted mice (FIG. 3-1A). Importantly, metastatic seeding of the lung takes place during the period of effective neutrophil depletion. While neutrophil depletion had no significant effect on apoptosis (FIG. 24) or the growth rate of the primary tumour (FIG. 3-1B), neutrophil-depleted tumour-bearing mice had increased metastatic burden (FIG. 3-1C-E). A thorough histological examination shows that while there is no significant difference in metastases size distribution (FIG. 3-1F) there is a dramatic increase in the number of metastatic events (FIG. 3-1G) suggesting that tumour entrained neutrophils (TENs) inhibit seeding in the pre-metastatic lung. Similar results were observed in 4T1 tumour bearing athymic mice suggesting that the anti metastatic effect of TENs is T-cell independent (FIG. 3-2).

In another widely used experimental model of metastasis tumour cells were injected directly into the tail vein of tumour-bearing mice and sham controls to examine the number of seeding tumour cells in the lungs, with and without neutrophil depletion (FIG. 2). Data described herein showed that while the presence of a tumour increased the seeding efficiency of tumour cells in the pre-metastatic lung (perhaps due to previously described processes (Hiratsuka, et al., *Nat Cell Biol* 8L1369-1375 (2006), herein incorporated by reference) there is a further increase in tumour cell seeding in neutrophil depleted tumour bearing mice (FIG. 2). Together, results from both spontaneous metastasis and tail vein injected tumour cells supported the conclusion that although a subset of Gr1+Cd11b+ cells might play a pro-metastatic role (Yan, et al., Cancer Res 70, 6139-6149 (2010), herein incorporated by reference), the net effect of TENs is inhibition of tumour cell seeding in the pre-metastatic lung.

The inventors then sought to determine whether TENs are sufficient to provide anti-metastatic protection independent of T-cell activity. To this end, athymic mice were injected with 4T1 cells via the tail vein to induce experimental metastases and then, 4 hours later, these mice were treated with TENs purified from 4T1 tumour-bearing mice. The transfer of TENs results in a dramatic delay in the formation of lung foci (FIG. 3-1H-I). In contrast, transfer of neutrophils purified from G-CSF treated animals had no significant effect on the formation of lung foci (FIG. 3-1J-K). These observations suggest that while tumour naïve, G-CSF mobilized neutrophils do not affect the formation of lung foci, TENs can provide anti-metastatic protection in vivo.

Since neutrophils are armed with an arsenal of toxic peptides and molecules the inventor's contemplated that TENs may be able to kill tumour cells directly and thereby provide anti-metastatic protection. Thus the tumour-cell killing capacity of TENs in vitro was tested. Neutrophils were purified from sham-operated and tumour-bearing mice and added to a culture of 4T1 cells that were labelled with luciferase to allow selective quantification within the co-culture. While control neutrophils, purified from sham-operated mice had no significant cytotoxic effect, TENs were highly cytotoxic (FIG. 4A). Such cytotoxicity was not observed when tumour cells were co-cultured with a mixture of lymphocytes and monocytes purified from either tumour bearing or sham-operated mice. No killing was observed when the neutrophils and the tumour cells were separated by a membrane demonstrating that physical contact is necessary for neutrophil mediated tumour-cell killing (FIG. 4B). A similar killing pattern was observed with MCF7 cells co-cultured with TENs from 4T1-tumour bearing mice (FIG. 4B). Furthermore, neutrophils purified from C57/B6 mice engrafted with B16 melanoma tumours gained the ability to kill B16 and 4T1 (FIG. 16) cells while neutrophils purified from sham-injected C57/B6 mice did not. To exclude the possibility that neutrophil cytotoxicity in mice bearing implantable 4T1 and B16 tumours is a result of a non specific anti graft immune response neutrophil cytotoxicity was evaluated in mice bearing spontaneous MMTV-PyMT driven mammary tumours. As can be seen in FIG. 4C, neutrophils purified from PyMT induced tumour bearing mice are highly cytotoxic suggesting that neutrophils entrainment is a direct consequence of the presence of a tumour. Furthermore, neutrophil entrainment was not a result of a general response to wounding since neutrophils purified from wounded mice were found to be non-cytotoxic (FIG. 25). Most importantly; while neutrophils isolated from healthy human volunteers were non-cytotoxic, neutrophils isolated from newly diagnosed breast cancer patients (prior to tumour removal or chemotherapy) were highly cytotoxic (FIG. 4D) suggesting that neutrophil entrainment is not limited to murine tumour models but also occurs during the natural course of the human disease.

Interaction between murine TENs and tumour cells using time-lapse microscopy was monitored. As early as 60 minutes after their addition, GFP labelled TENs were seen converging on the adherent 4T1 cells (red, FIG. 4E). The neutrophils initiate physical contact with the tumour cell at which time the tumour cell underwent dramatic morphological changes. Finally, the neutrophils disengaged, leaving behind the fragmented tumour cell (FIG. 4E). To ascertain whether the interaction between TENs and tumour cells results in tumour cell apoptosis was tested for the activation of Caspase 3. This was achieved by labelling the tumour cells with a Caspase 3 fluorescent substrate prior to the addition of TENs. As can be seen in FIG. 4F there were no Caspase 3 positive cells (GFP positive) in the control culture while GFP positive cells can be seen in the 4T1+TEN co-culture. Quantification of GFP intensity as an indicator of Caspase 3 activation shows a dramatic increase in the presence of neutrophils (FIG. 4F). Time-lapse microscopy showed the TENs induced activation of Caspase 3 in tumour cells in real time. Control neutrophils do not form prolonged interaction with tumour cells and fail to activate Caspase 3 and induce apoptosis.

Next the mechanism by which neutrophils kill tumour cells was characterized. Neutrophils can generate reactive oxygen species (ROS) through the activity of the NADPH Oxidase complex and induce cell death by an oxidative burst (FIG. 4G). Indeed, co-culture of TENs with tumour cells in the presence of Apocynin, a specific inhibitor of the NADPH Oxidase complex, completely inhibits the neutrophil mediated tumour-cell killing (FIG. 4H). Next, the reactions downstream from NADPH Oxidase were interfered with using pharmacological inhibitors. Addition of exogenous superoxide dismutase did not inhibit cell death suggesting that superoxides per se are not directly involved in cell killing. In contrast, catalase (which converts $H_2O_2$ to $H_2O$ and $O_2$) completely inhibits cell killing (FIG. 4H). Interestingly, the presence of the hypochlorous acid scavenger, taurine, did not reduce tumour-cell killing by stimulated neutrophils suggesting the killing is by $H_2O_2$ (FIG. 4H). This notion is further supported by the observations that TENs generate more $H_2O_2$ than control neutrophils (FIG. 4I) and $H_2O_2$ production by TENs decreases in the presence of Ly-6G (FIG. 4J) or Gr-1. Finally, to test whether this process through which neutrophils inhibit metastasis was also relevant in vivo, the effect of Apocynin on spontaneous metastasis was tested. Experiments showed that Apocynin treatment enhanced metastasis and that Apocynin treated mice developed spontaneous lung metastases earlier than control mice (FIG. 4K). These results suggest that neutrophils induce tumour cell death through generation of ROS by the NAPDH Oxidase complex. However, it is the generation of $H_2O_2$ rather than superoxides or the $H_2O_2$ chlorine metabolite, hypochlorous acid that is responsible for the killing.

What is the mechanism through which neutrophils are activated by the primary tumour? 4T1 tumour bearing mice have been shown to have high levels of serum G-CSF that may account for neutrophil mobilization (DuPre, et al., Exp Mol Pathol 82, 12-24 (2007), herein incorporated by reference). Indeed, in vivo rhG-CSF administration induces a significant increase in circulating and lung-associated neutrophils (FIG. 7). However, it does not induce a cytotoxic neutrophil response in vivo (FIG. 3-1J-K) or in vitro (FIG. 5-1A). These observations suggest that G-CSF secretion is sufficient for both the mobilization and lung sequestration of neutrophils but that further activation is required for the entrainment of their anti-metastatic behaviour.

The expression array performed on pre-metastatic lungs showed a 7.9 and 4.6 fold increase in CCR1 and CCR2 respectively, both of which are expressed in murine neutrophils, (Reichel, et al., J Leukoc Biol 79, 114-122 (2006), herein incorporated by reference) (FIG. 8). Since 4T1 tumours were shown to secrete CCL2 and CCL5, (DuPre, et al., Int J Exp Pathol 88, 351-360 (2007), herein incorporated by reference) that are potential ligands for CCR2 and CCR1 respectively, these chemokines were tested to find out whether either or both would induce neutrophil-mediated tumour-cell killing. The addition of either mCCL2 or mCCL5 was discovered to stimulate naïve neutrophils and induced tumour cell killing in vitro suggesting that both are sufficient for neutrophil entrainment (FIG. 5-1A). This observation is further substantiated by the fact that CCL2 and CCL5 induce an increase in $H_2O_2$ production in naïve neutrophils (FIG. 5-1B). Similarly, both hCCL2 and hCCL5 can stimulate human neutrophils purified from healthy volunteers and induce the killing of human MDA-MB-231 in vitro (FIG. 5-1C). Since CCL2 and CCL5 expression has been documented in several human tumours (see for example Payne, et al., J Invest Dermatol 118:915-922 (2002), Soria, et al., Cancer Lett 267:271-285 (2008), herein incorporated by reference) this observation suggested that neutrophil entrainment by tumour-secreted factors might also be relevant in human malignancies.

CCL2 knockdown in tumours, with 2 independent shRNAs, blocks neutrophil entrainment (FIGS. 5-1D and 5-1E) without affecting mobilization (FIG. 5-1F). Knockdown of CCL2 leads to a reduction in both CCL2 and CCL5 levels in the circulation (FIG. 5-1G). CCL5 knockdown on the other hand is insufficient to block entrainment perhaps due to redundancy with CCL2. Neutrophils mobilized by CCL2kd tumours were not activated as evidenced by their reduced $H_2O_2$ production when compared to neutrophils mobilized by control tumours (FIG. 5-1H). To further understand the role of tumour secreted CCL2 on tumour growth and metastasis in vivo, the growth and spontaneous metastasis of orthotopically implanted CCL2 knockdown (CCL2kd) were compared to control 4T1 tumours. Consistent with the pro-tumourigenic properties attributed to CCL2 (Loberg, et al. Cancer Res 67:9417-9424 (2007), Lu, et al. J Biol Chem 284:29087-29096 (2009), herein incorporated by reference) it was also found that primary CCL2kd tumours show growth retardation when compared to control tumours (FIG. 5-1I). However, spontaneous metastasis from the CCL2kd tumours occurs earlier (FIG. 5-1J) suggesting that these tumours have increased metastatic potential. Taken together, these observations suggest that while CCL2 secretion by the primary tumour has a beneficial effect and enhances growth at the primary site, it is concomitantly capable of inducing an anti-metastatic neutrophil response and inhibiting tumour cell seeding at a distant site. Furthermore, these observations support the notion that a specific tumour secreted factor, namely CCL2, rather than a non-specific host versus tumour immune response, is responsible for neutrophil entrainment.

Neutrophils have been shown to have a pro-tumourigenic effect at the primary tumour site through enhanced angiogenesis (Nozawa, at al, Proc Natl Acad Sci USA 103:12493-12498 (2006); Shojaei, et al., Proc Natl Acad Sci USA 105: 2640-2645 (2008), herein incorporated by reference), increased degradation of the ECM (De Larco, et al., Clin Cancer Res 10:4895-4900 (2004); Yang, et al., Cancer Cell 13:23-35 (2008), herein incorporated by reference), and immune suppression Schmielau, et al., Cancer Res 61:4756-4760 (2001); Youn, et al., J Immunol 181:5791-5802 (2008), herein incorporated by reference). In addition, an anti-tumourigenic role has been observed following immunologic (Hicks, et al., Proc Natl Acad Sci USA 103:7753-7758 (2006), herein incorporated by reference) or cytokine activation (Colombo, et al., J Immunol 149:113-119 (1992), herein incorporated by reference) as well as through blockade of TGF-Beta (Fridlender, et al., Cancer Cell 16:183-194 (2009), herein incorporated by reference). To gain further insight into the function of CCL2 at the primary site and the pre-metastatic site other tumour secreted factors were tested to find out whether they have the capacity to modulate TENs cytotoxic activity. TGF-Beta, which is known to be secreted by 4T1 tumours (Zhang, et al., J Immunol 181:3690-3697 (2008), herein incorporated by reference) dramatically inhibited TENs cytotoxicity towards tumour cells (FIG. 5-1K). Since 4T1 tumours secrete TGF-Beta, its activity in the vicinity of the primary tumour is high (FIG. 5-1L) resulting in inhibition of TEN cytotoxicity toward the primary tumor. However, at distant sites such as the pre-metastatic lung, TGF-Beta activity is low (FIG. 5-1L) and permits TENs cytotoxicity toward tumor cells providing a plausible explanation for the different effects of CCL2 at the primary and the pre-metastatic sites.

CCL2 was contemplated to have considerably different effects at the primary tumour site and in the future metastatic site. Several studies have shown that CCL2 has a pro-tumourigenic effect and that high CCL2 serum levels in cancer patients are associated with advanced disease (Soria, et al., Cancer Lett 267:271-285 (2008), herein incorporated by reference). Conversely, other clinical studies show that high CCL2 levels are associated with a better prognosis for breast cancer patients (Dehganzada, et al., Clin Cancer Res 12, 478-486 (2006), herein incorporated by reference) and a prolonged overall survival in pancreatic, gastric and colon cancer patients (Monti, et al., Cancer Res 63:7451-7461 (2003); Tonouchi, et al., Scand J Gastroenterol 37:830-833 (2002); Watanabe, et al., Dis Colon Rectum 51:1800-1805 (2008), herein incorporated by reference). These latter studies are consistent with results described herein and provide evidence for the relevance of CCL2 expression to human disease.

Inhibition of TGF-Beta-signalling at the primary tumour site (Fridlender, et al., Cancer Cell 16:183-194 (2009), herein incorporated by reference) was reported to lead to the secretion of factors (primarily from macrophages), which recruit increased numbers of neutrophils to the tumour bed with enhanced tumour cell killing capacity. In vivo, this killing is completely dependent on activated CD8+ T cells. As demonstrated herein, the situation at the metastatic site is considerably different. Neutrophils arrive early at the pre-metastatic site prior to the arrival of detectable metastatic tumour cells and are activated in response to chemokines CCL2/5 secreted by the primary tumour. These neutrophils are not exposed to the inhibitory effect of tumour secreted TGF-β and are capable of killing metastatic cells. This process is independent of activated T cells since it is observed in both immunocompetent and athymic mice. Thus CCL2 secreted by the primary tumour may act as a double-edged sword, promoting the growth of the primary tumour where TGF-β activity is high while at the same time inducing a neutrophil mediated anti-metastatic response at the future metastatic site where TGF-β activity is lower. Unfortunately, the anti-metastatic protection provided by TENs is not complete as eventually tumour cells outcompete TENs and form metastases. In contrast, results obtained during the development of the present inventions suggested a means of entraining neutrophils to suppress metastatic tumour cell growth that may be exploited therapeutically in adoptive transfer procedures like those described here for the management of micrometastatic disease.

Animals
5-7 weeks old nude, Balb/c, C57/B6, FVB and Balb/c-Ubc-GFP mice were purchased from Taconic, Jackson lab and Harlan. Experiments involving animals were approved by MSKCC's Institutional Animal Care and Use Committee (IACUC).
Cell Lines
4T1, B16-F10, and Lewis Lung Carcinoma (LLC) murine tumour cell lines as well as the human MCF7 and MDA-MB-231 mammary tumour cell lines were purchased from the ATCC. The human 4175 (LM2) cell line was described in Minn, et al., Nature 436:518-524 (2005), herein incorporated by reference). CCL2 and CCL5 knockdown 4T1 cells were generated by lentiviral transduction with CCL2 and CCL5 specific shRNAs from the SKI shRNA lentiviral collection. 4T1, MCF7 and 4175 were orthotopically injected into the mammary fat pad. B16-F10 and LLC cells were injected intradermally.
Spontaneous Metastasis Assay
4T1 cells were transduced with pLVX based lentiviral particles encoding for firefly luciferase. Balb/C or nude female mice were orthotopically injected with $5 \times 10^6$ luciferase labelled cells. Metastatic progression was monitored using IVIS200 imaging system to measure lung specific luciferase activity starting on day 3 post tumour engraftment. Analysis of metastases size distribution and number was done histologically.
Tissue Injury
Female FVB mice were anesthetized and shaved at the wounding site. An area of skin (4 mm in diameter) area of skin was surgically removed from the dorsal region. Control mice were anesthetized and shaved but not injured. 48 hours after surgery, the mice were sacrificed and circulating neutrophils were purified.
Microarray
Nude female mice were injected with $5 \times 10^6$ 4T1 cells into the mammary fat pad. Control mice were injected with PBS. 3 or 7 days later, the mice were sacrificed and perfused with ice cold PBS. Lung and liver tissue samples were harvested and flash frozen. mRNA expression was analyzed using microarray chip MOE430A-2 (Affymetrix) on 3 mice per group.
Immunohistochemistry
Mice were euthanized and perfused with PBS prior to tissue excision and fixation. Tissues were embedded in either OCT or paraffin and stained using standard procedures.
Antibodies
Antibodies used for immunohistochemistry—MMP9, F4/80 and CCR2 (all from AbCam), Myeloperoxidase (Dako), Ly-6G and Cd11b (both from BD), and Cleaved Caspase 3 (Cell signalling). Antibodies used for western blotting—Actin (Sigma), CCL2 (AbCam) and CCL5 (R&D) p-SMAD2 (cell signalling). Antibodies used for FACS analysis FITC-Ly-6G, FITC-Cd11b, FITC-F4/80, FITC-Cd34 and FITC-c-Kit (all from BD) and VEGFR1-AP (R&D).
Neutrophil Depletion
Neutrophil depletion was achieved using daily IP injections of 12.5 µg Rat anti-Gr-1 antibody (BD) or Rat anti-Ly-6G antibody (BD) starting on day 3 post tumour engraftment. Starting on day 14, neutrophil depleting antibodies were administered twice daily. Control mice were injected with 12.5 pa Rat isotype control (BD). Neutrophil depletion was monitored by manual blood differentials and FACS analysis.
Flow Cytometry
Peripheral blood was collected into EDTA-coated tubes, washed and resuspended in FACS buffer solution (PBS, 2% heat-inactivated FCS, 5 mM EDTA, and 0.02% sodium azide). The samples were blocked with CD16/34 and then incubated with fluorophore-conjugated antibodies. Erythrocytes were then lysed with FACS lysing solution (BD Biosciences) and the cell suspensions were analyzed on a FACSCalibur (BD Biosciences).
Colony Formation Assay
Female nude mice were orthotopically injected with $5 \times 10^6$ puromicin resistant 4T1 cells. On days 7 and 14 post tumour engraftment the mice were sacrificed and perfused with PBS. The lungs and livers were removed, washed with PBS and dissociated with Collagenase A (Roche). The single cell suspension was then plated onto puromicin containing media and selected for 14 day. Colonies were stained with Methylene-Blue and counted manually.
Mouse Neutrophil Purification
Whole blood was collected by cardiac puncture using heparinized (Sigma) syringe. The blood was diluted with 5 volumes of PBS containing 0.5% BSA and subjected to a discontinuous Histopaque (Sigma) gradient (1.077 and 1.119). Neutrophils were collected from the 1.077-1.119 interface, lymphocytes and monocytes collected from the plasma-1.077 interface. RBCs were eliminated by hypotonic lysis. The cells were washed twice with PBS-BSA and re-suspended in Opti-MEM (Invitrogen) 0.5% FBS in a final concentration of $2 \times 10^6$ cells/ml. Neutrophil purity and viability were determined visually and were consistently >98%.
Human Neutrophil Purification
As part of a Memorial Sloan-Kettering Cancer Center institutionally approved protocol, blood samples (~10 cc) were collected from healthy volunteers or from patients who were already having blood drawn for pre-surgical testing. Patients were consented accordingly as part of the approved protocol. Select patients had a diagnosis of invasive breast cancer based on pathology review of prior core or fine needle aspiration biopsies of their primary tumor. Patients had either mastectomies or lumpectomies planned and had blood drawn prior to definitive surgical removal of their primary tumor or chemotherapy. Blood samples were transferred to the lab for analysis no more than 1 hour post-blood draw. Heparinzed blood (20 U/ml final) was mixed with an equal volume of Dextran 500 (3% in saline) and incubated 30 minutes at room temperature. The leukocyte-rich supernatant was layered on top of histopaque 1077 (Sigma) and centrifuged. Neutrophils, collected in the pellet fraction, were resuspended in 10 ml 0.2% NaCl for 30 seconds to remove contaminating erythrocytes. Isotonicity was restored by the addition of 10 ml 1.6% NaCl. Neutrophils were than washed three times in Hanks's balanced salt solution and resuspended in RPMI+FCS2%.
In vitro Killing Assay
Luciferase labelled cells (5,000/well) were plated on a 96-well, flat bottom white polystyrene tissue culture plate in OptiMEM 0.5% FBS (mouse neutrophils) or RPMI 2% FBS (human neutrophils). 4 hours later, purified neutrophils (100,000/well for mouse neutrophils and 5000 for human neutrophils) were added to the plated tumour cells and co-cultured overnight. Chemokines or inhibitors (Apocynin (100 □M), Catalase (1,000 u/ml), Superoxide Dismutase (1,000 u/ml) and Taurine (50 mM) all from Sigma) were added to the culture immediately after neutrophils were added. Following overnight incubation, the wells were washed once with PBS, the cells were lysed and luciferase activity was measured using the Clarity (Bio-Tek) microplate luminescence reader.
$H_2O_2$ Production Assay
4T1 tumour cells (5,000/well) were plated on a 96-well, clear bottom black polystyrene tissue culture plate in Opti-MEM 0.5% FBS. 4 hours later, purified neutrophils (100,000/well) were added to the plated tumour cells. The production of H₂O₂ was measured with the Invitrogen Amplex Red Hydrogen Peroxide/peroxidise assay kit using a Synergy microplate reader.

In Vivo Administration of Apocynin

Mice were orthotopically injected with 5×10⁶ luciferase labelled 4T1 cells. 24 hours later Apocynin (2.4 g/liter) was administered in sugar sweetened drinking water. Control animals were treated with sugar sweetened water. Drinking water for both Apocynin treated and control mice were replaced every two days.

Time-Lapse Microscopy 20,000 4T1 cells were labelled with CellTracker-Red (molecular Probes) according to the manufacturer instructions and plated on a chamber slide. 4 hours later, 400,000 neutrophils, isolated from 4T1 tumour-bearing Balb/c Ube-GFP mice, were added to the culture. Live imaging of Caspase 3 activation was done by labelling the tumour cells with the Caspase 3 substrate NucView 488 (Biotium) prior to the addition of GFP negative TENs. Images were taken every 10 minutes using the MetaMorph imaging system.

Neutrophil Transfer

Female nude mice were injected with 5×10⁴ luciferase labelled 4T1 cells to the tail vein. 4 hours later, the mice were injected with 5×10⁶ TENs or G-CSF mobilized neutrophils into the tail vein. Control mice were injected with vehicle. Formation of lung metastases was monitored using the IVIS-200 optical in vivo imaging system.

Chemokine Administration rhG-CSF (Neupogen, Amgen) was administered daily (250 microg/kg/day) s.c. for 4 consecutive days. In vitro neutrophil stimulation—neutrophils were isolated from naïve mice and co-cultured with tumour cells in the presence of mCCL2, mCCL5 (both from R&D) or rhG-CSF (all at 20 ng/ml) or with TGF-Beta (R&D) (up to 200 pMolar). Human neutrophils purified from healthy volunteers were stimulated in vitro with hCCL2, hCCL5, hCCL3, hCCL4, hCXCL1, hCXCL12 and hCXCL16 (all from R&D at 100 ng/ml) or with rhG-CSF (20 ng/ml).

Statistical Analysis

For statistical analysis, the data is presented as mean±SEM and were analyses using Students t tests. Differences were considered significant when $p<0.05$.

IV. The Following is an Example of One Embodiment of the Invention

The leading cause of cancer related mortality is metastatic spread of tumor cells to distant sites and the location of these sites varies considerably among different primary tumor types. Several studies have shown that the site of metastasis may be determined by a specific gene expression pattern, or signature, in primary tumor cells that mediates metastasis to specific distant organs (Gupta, et. al., Cell 127:679-695 (2006), herein incorporated by reference). On the other hand, tumor induced changes in the microenvironment of distal organs prior to colonization might make certain tissues more receptive for colonization by migrating tumor cells (Joyce, et. al., Nat Rev Cancer 9:239-252 (2009), herein incorporated by reference). Recent studies have suggested that factors secreted from the primary tumor may modulate the future site of metastasis in a directed fashion (Brier, et. al., Cancer Cell 15:35-44 (2009), Kaplan, et. al., Nature 438:820-827 (2005), herein incorporated by reference).

The 4T1 routine mammary tumor model was employed to gain insight into the early transcriptional changes that take place in the pre-metastatic niche. Orthotopically implanted 4T1 tumors spontaneously metastasize primarily to the lung whereas metastases to the liver, brain, and bones are less frequent and arise much later (FIG. 1A). mRNA microarray analysis of lung and liver samples from tumor-bearing versus sham-operated mice shows no significant differences in gene expression 3 days after turnout engraftment. In contrast, 325 and 912 genes were significantly misregulated in the lung and liver (respectively) of turnout-bearing mice 7 days after tumor engraftment (FIG. 1B). Of the 325 lung misregulated genes, 293 were lung specific and were not misregulated in the liver. Merely a small number of tumor cells were found in the lungs at this point suggesting that tumor-cell contribution to the expression array is negligible (FIG. 1C).

Of the acutely upregulated genes that came up in the expression array (FIG. 1D), MMP9 was of high interest given that this protein is involved in tissue remodeling and metastasis-associated degradation of the extra cellular matrix (Hiratsuka, et. al., Cancer Cell 2:289-300 (2002), Itoh, et. al., Clin Exp Metastasis. 17:177-181 (1999), herein incorporated by reference).

A dramatic increase in cells staining positive for MMP9 can be seen in the pre-metastatic lung but not in the liver (FIG. 2A). The increase in MMP9 staining was not unique to the pre-metastatic lungs of 4T1 tumour bearing mice but was also found in mice bearing other pre-metastatic xenografts and in spontaneous tumor models (FIG. 6). Interestingly, there was no increase in MMP9 staining in mice with orthotopic MCF7 tumours, which fail to colonize the lung.

The inventors contemplated that MMP9+ cells present in the pre-metastatic lung might be neutrophils as several neutrophil-specific genes (such as cathelicidin and lactoferrin) are acutely upregulated in the pre-metastatic expression array (FIG. 1D). Immunohistological analysis performed on pre-metastatic lung tissue shows that the MMP9+ cells in the lungs co-stain with the neutrophil marker Ly-6G (FIG. 2B) but not with the pan macrophage marker F4/80. Further analyses show that MMP9+ cells in the pre metastatic lung co-stain with other neutrophil markers such are myeloperoxidase and Cathelicidin (data not shown). Lung tissue taken from human breast cancer patients with lung metastases show high levels of myeloperoxidase staining (in 5/5 case examined) suggesting that neutrophil recruitment to the lungs is also relevant in human breast cancer (FIG. 6C).

Neutrophils have been implicated in pro tumourigenic processes (Pekarek, et. al., J Exp Med 181:435-440(1995), Shojaei, et. al., Nature 450, 825-831 (2007), herein incorporated by reference) and CD11b+ bone marrow derived cells were shown to take part in the priming of the pre-metastatic niche (Erler, et. al., Cancer Cell 15:35-44 (2009), herein incorporated by reference). The inventors therefore wanted to assess the contribution of tumour-entrained neutrophils (TENs) to the establishment of the pre-metastatic niche. To this end mice were orthotopically injected with 4T1 cells to generate a primary tumour and were then treated with either control (IgG) or a neutrophil depleting antibody (Gr-1) starting on day 3 post tumour engraftment (FIG. 2C). Control mice were sham-operated (no tumour) and treated with the control antibody (IgG). All mice were challenged with i.v. injection of puromicin-resistant 4T1 cells 7 days after primary tumour engraftment (FIG. 2C). The mice were sacrificed 3 days later (day 10) and the number of colony-forming puromicin-resistant tumour cells in the lungs was determined (FIG. 2C). Tumour-bearing mice treated with the Gr-1 antibody show significant reduction of neutrophil numbers in the circulation, lungs and the primary tumour-rim (FIG. 2D-E).

Since the presence of a primary tumor was shown to promote metastasis "priming" the presence of tumor-stimulated neutrophils affects this process. In this experiment lung colonization potential of labeled tumor cells were tested under different conditions. Sham+IgG—mice that were sham operated, do not bear a tumor and treated with a control antibody. Tumor+IgG—mice that were orthotopically injected with a 4T1 mammary tumor and treated with a control antibody. Tumor+Gr-1—mice that were orthotopically injected with a 4T1 mammary tumor and treated with a neutrophil depleting antibody (Gr-1). Consistent with previous studies—the presence of a primary tumor promotes the colonization of tumor cells in the lungs (compare Sham+IgG and Tumor+IgG). Neutrophil depletion with Gr-1 increases the colonization potential of tumor cells in the lungs of tumor bearing mice (compare Tumor+IgG and Tumor+Gr-1) suggesting that the presence of neutrophils inhibits tumor-cell colonization of the lungs. Therefore, tumor stimulated neutrophils (i.e. TENs) inhibited tumor cell colonization in the lung. (FIG. 2F). The 2-fold increase in tumour-cell seeding in the lungs of tumour bearing compared to sham-operated mice, is consistent with previous studies (Hiratsuka, et. al., Cancer Cell 2:289-300 (2002), herein incorporated by reference) and indicated that the metastatic efficiency is enhanced in the presence of a primary tumour (FIG. 2F).

Assuming that priming of the lungs for the arrival of tumour cells from the circulation is mediated by TENs, neutrophil depletion should have reduced the seeding efficiency in the lungs. However, The inventors observed a 2-fold and a 4-fold increase in seeding efficiency compared to tumour bearing mice treated with a control antibody and sham-operated mice respectively, suggesting that TENs attenuate the seeding of tumour cells in the lungs. Interestingly, neutrophil depletion did not affect the growth of the primary tumour (FIG. 2G).

The inventors next tested the long-term effects of neutrophil depletion on spontaneous metastasis from the mammary fat pad. Neutrophil depletion in the circulation was highly effective until day 16 post tumour engraftment after which neutrophil levels were not significantly different in IgG treated or Gr-1 treated mice (FIG. 3B). While neutrophil-depletion had no effect on the growth rate of the primary tumour (FIG. 3C), neutrophil-depleted tumour-bearing mice developed lung metastases earlier than control mice. Moreover, the lung metastases in neutrophil-depleted mice also grew significantly faster than in control mice (FIGS. 3A and 3D).

The inventors sought to determine whether TENs are sufficient for providing anti-metastatic protection. To this end, mice were injected with 4T1 cells via the tail vein and then challenged with neutrophils purified from 4T1 tumour-bearing mice or sham operated control animals. The transfer of TENs results in a dramatic delay in the formation of lung metastases (FIG. 3 E-G). These observations suggest that TENs can provide anti-metastatic protection in vivo. The inventors therefore propose that TENs are sufficient for clearance of lung arrested cancer cells and thus confer anti-metastatic protection.

Since neutrophils are armed with an arsenal of toxic peptides and molecules the inventors postulated that TENs may be able to kill tumour cells directly and thereby provide anti-metastatic protection. The inventors therefore tested the tumour-cell killing capacity of TENs in vitro. Neutrophils were purified from sham-operated and tumour-bearing mice and added to a culture of 4T1 cells that were labeled with luciferase to allow selective quantification within the co-culture. While control neutrophils, purified from sham-operated mice had no significant cytotoxic effect, TENs were highly cytotoxic (FIG. 4A). Such cytotoxicity was not observed when tumour cells were co-cultured with a mixture of lymphocytes and monocytes purified from either tumour bearing or control mice. No killing was observed when the neutrophils and the tumour cells were co-cultured separated by a membrane implying that physical contact is necessary for neutrophil mediated tumour-cell killing (FIG. 4B). A similar killing pattern was observed with MCF7 cells co-cultured with TENs from 4T1-tumour bearing mice. Furthermore, neutrophils purified from C57/B6 mice engrafted with B16 melanoma tumours gained the ability to kill 4T1 cells while purified neutrophils from naive C57/B6 mice could not (FIG. 4C). These results suggest that there is a general mechanism by which TENs gain the capacity to kill tumour cells and thereby inhibit metastasis. The inventors were also able to monitor the interaction between TENs and tumour cells using time-lapse microscopy. As early as 60 minutes after their addition, GFP labeled TENs can be seen converging on the adherent 4T1 cells (red). The neutrophils initiate physical contact with the tumour cell at which time the tumour cell undergoes nuclear blebbing, a morphological change tightly associated with apoptosis. Finally, the neutrophils disengage, leaving behind the fragmented tumour cell (FIG. 4D).

Next the inventors sought to characterize the mechanism by which neutrophils kill tumour cells. Neutrophils can generate reactive oxygen species (ROS) through the activity of the NADPH Oxidase complex and induce cell death by an oxidative burst (FIG. 4E). Indeed, co-culture of TENs with tumour cells in the presence of Apocynin, a specific inhibitor of the NADPH Oxidase complex, completely inhibits the neutrophil mediated tumour-cell killing (FIG. 4F). The inventors then interfered with the reactions downstream from NADPH Oxidase using pharmacological inhibitors. Addition of exogenous superoxide dismutase did not inhibit cell death suggesting that superoxides per se are not directly involved in cell killing. In contrast, catalase (which converts f $H_2O_2$ to $H_2O$ and $O_2$) completely inhibits cell killing (FIG. 4F). Interestingly, the presence of the hypochlorous acid scavenger, taurine, did not reduce tumour-cell killing by stimulated neutrophils suggesting the killing is by $fH_2O_2$ (FIG. 4E). Finally, to test whether this process through which neutrophils inhibit metastasis is also relevant in vivo the inventors tested the effect of Apocynin on spontaneous metastasis. The inventors show that Apocynin treatment enhances metastasis and that Apocynin treated mice developed spontaneous lung metastases earlier than control mice (FIG. 4G). These results suggest that neutrophils induce tumour cell death through generation of ROS by the NAPDH Oxidase complex.

However, it is the generation of $H_2O_2$ rather than superoxides or the f $H_2O_2$ chlorine metabolites that are responsible for the killing. What is the mechanism through which neutrophils are activated by the primary tumour? 4T1 tumour bearing mice have been shown to have high levels of serum G-CSF that may account for neutrophil mobilization 9. Indeed, in vivo rhG-CSF administration induces a significant increase in circulating and lung-associated neutrophil numbers (FIG. 7).

However, it does not induce a cytotoxic neutrophil response in vitro (FIG. 5A). This observation suggests that although neutrophil mobilization through G-CSF may be necessary for the protective role of TENs, further activation is necessary for the entrainment of their anti-metastatic behavior.

The expression array performed on pre-metastatic lungs showed a 7.9 and 4.6 fold increase in CCR1 and CCR2 respectively, both of which are expressed in mouse neutrophils (Reichel, et. al., J Leukoc Biol 79, 114-122 (2006), herein incorporated by reference) (and FIG. 8).

Since 4T1 tumours were shown to secrete CCL2 and CCL5 (DuPre, et. al., Int J Exp Patho 188, 351-360 (2007), herein incorporated by reference) that are potential ligands for CCR2 and CCR1 respectively, the inventors tested whether these chemokines can induce neutrophil-mediated tumour-cell killing. The inventors found that addition of either CCL2 or CCL5 can stimulate naive neutrophils and induce tumour cell killing in vitro implying that both are sufficient for neutrophil entrainment (FIG. 5A). However, while CCL5 knock-down of orthotopically injected 4T1 tumours retained their ability to entrain neutrophils, in vivo CCL2 knockdown turn-outs did not, suggesting that unlike CCL5, CCL2 is both required and sufficient for neutrophil entrainment in vivo (FIGS. 5B and 5C). Several studies have shown that CCL2 has a pro tumorigenic effect and that high CCL2 serum levels in cancer patients are associated with advanced disease (Loberg, et. al., Cancer Res. 67:9417-9424 (2007), Lu, et. al., J Biol Chem 284:29087-29096 (2009), Soria, et. al., Cancer Lett 267:271-285 (2008), each of which is herein incorporated by reference) while others propose that CCL2 has an anti-metastatic role and that high CCL2 serum levels negatively correlate with cancer progression (Dehqanzada, et. al., Clin Cancer Res 12:478-486 (2006), Huang, et. al., Cancer Immunol Immunother 39:231-238 (1994), Takahashi, et. al., Clin Exp Metastasis (2009), Tonouchi, et. al., Scand J Gastroentero 137:830-833 (2002), each of which is herein incorporated by reference). To gain insight into the role of tumour secreted CCL2 on tumour growth and metastasis in vivo, the inventors compared the growth and spontaneous metastasis of orthotopically implanted CCL2 knockdown (CCL2kd) and control 4T1 tumours. Consistent with the pro tumourigenic properties attributed to CCL2 the inventors found that primary CCL2kd tumours show growth retardation when compared to control tumours (FIG. 5D). However, The inventors found that spontaneous metastasis from the CCL2kd tumours occurs earlier (FIG. 5E) suggesting that these tumours have increased metastatic potential. Taken together, these observations suggest that while CCL2 secretion by the primary tumour has a beneficial effect and enhances growth at the primary site, it is concomitantly capable of inducing an anti-metastatic neutrophil response and inhibiting tumour cell seeding at a distant site.

The role of neutrophils in tumourigenesis at a primary tumour site has been investigated in a number of recent studies. A pro-tumourigenic role through enhanced angiogenesis (Nozawa, et. al., Proc Natl Acad Sci U.S.A. 103:12493-12498 (2006), Shojaei, et. al., Proc Natl Acad Sci U.S.A. 105:2640-2645 (2008), each of which is herein incorporated by reference) increased degradation of the ECM 21, and immune suppression have all been reported (Schmielau, et. al., Cancer Res 61:4756-4760 (2001), Youn, et. al., J Immunol 181:5791-5802 (2008), each of which is herein incorporated by reference). In addition, an anti-tumourigenic role has been observed following immunologic (Hicks, et. al., Proc Natl Acad Sci U.S.A. 103:7753-7758 (2006), herein incorporated by reference) or cytokine activation (Colombo, et. al., J Immunol. 149:113-119 (1992), herein incorporated by reference) as well as through blockade of TGFβ (Fridlender, et. al., Cancer Cell 16:183-194 (2009), herein incorporated by reference). In this latter study, inhibition of TGFβ-signalling leads to the secretion of factors (primarily from macrophages), which recruit increased numbers of neutrophils to the tumour bed with enhanced tumour cell killing capacity. In vivo, this killing is completely dependent on activated CD8+ T cells. As the inventors demonstrated here, the situation at the metastatic site is considerably different. Neutrophils arrive early at the pre-metastatic organ prior to the arrival of detectable tumour cells, are activated in response to chemokines CCL2/5 secreted by the primary tumour and are capable of killing metastatic cells. This process is independent of activated T cells since it is observed in athymic mice. Interestingly, the inventors find that CCL2 secreted by the primary tumour acts as a double-ended sword; promoting the growth of the primary tumour while at the same time inducing a neutrophil mediated anti-metastatic response at the future metastatic site. These results suggest a heretofore unknown role of neutrophils in suppressing metastatic tumour cell growth that may have the potential to be exploited therapeutically in the management of micrometastatic disease.

From the foregoing description, one skilled in the art can easily ascertain the essential characteristics of this invention, and without departing from the spirit and scope thereof, can make changes and modifications to the invention to adapt it to various usages and conditions and to utilize the present invention to its fullest extent. The preceding embodiments and examples are to be construed as merely illustrative, and not limiting of the scope of the invention in anyway whatsoever.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in fatty-acid chemistry, molecular biology, biochemistry, chemistry, organic synthesis, paint and varnish manufacturing, botany, human and veterinary nutrition and medicine, or related fields are intended to be within the scope of the following claims.

EXPERIMENTAL

The following are examples that further illustrate embodiments contemplated by the present invention. It is not intended that these examples provide any limitations on the present invention.
In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example I

This example describes exemplary materials and methods used during the development of the present inventions.
Animals: Nude, Balb/C, C57/B16 and Balb/C-Ubc-GFP were purchased from Taconic,
Jackson lab and Harlan. Experiments involving animals were approved by Memorial Sloan-Kettering Cancer Center's Institutional Animal Care and Use Committee (IACUC).
Cell lines: 4T1, B16-F10 and Lewis Lung Carcinoma (LLC) routine tumour cell lines as well as the human MCF7 mammary cell line were purchased from the ATCC. The human 4175 (LM2) cell line. CCL2 and CCL5 knockdown 4T1 cells were generated by lentiviral transduction with CCL2 and CCL5 specific shRNAs from the SKI shRNA lentiviral collection.

Spontaneous metastasis assay: Nude female mice were orthotopically injected with 5×10⁶ luciferase labeled cells. Metastatic progression was monitored using IVIS200 imaging system to measure lung specific luciferase activity starting on day 3 post tumour engraftment.

Microarray: Nude female mice were injected with 5×10⁶ 4T1 cells into the mammary fat pad. Control mice were injected with PBS. 3 or 7 days later, the mice were sacrificed and per/used with ice cold PBS. Lung and liver tissue samples were harvested and flash frozen, mRNA expression was analyzed using microarray chip MOE430A-2 (Affymetrix, Santa Clara, Calif.).

Immunohistochemistry: Mice were euthanized and perfused with PBS prior to tissue excision and fixation. Tissues were embedded in either OCT or paraffin and stained using standard procedures.

Antibodies: Antibodies used for immunohistochemistry—MMP9 (AbCam, Cambridge, Mass.), Ly-6G (BD), F4/80 (AbCam), Myeloperoxidase (Dako, Carpinteria, Calif.) and CCR2 (AbCam). Antibodies used for Western blotting—Actin (Sigma), CCL2 (AbCam) and CCL5 (Research & Diagnostics Systems, Inc. (R&D Systems) Minneapolis, Minn., USA).

Neutrophil depletion: Neutrophil depletion was achieved using daily LP injections of 12.5 µg Rat anti-Gr-1 antibody (BD) starting on day 3 post tumour engraftment. Starting on day 14, Gr-1 was administered twice daily. Control mice were injected with 12.5 µg Rat isotype control (BD). Neutrophil depletion was monitored by manual blood differentials.

Colony formation assay: Female nude mice were orthotopically injected with 5×10⁶ 4T1 cells, control mice were injected with PBS. Starting on day 3 post tumor engraftment, tumor bearing mice were either treated with Gr-1 to deplete neutrophils or treated with isotype control IgG. Control, sham operated mice were treated with isotype control IgG. On day 7 post tumor engraftment, all mice were injected with 5×10⁴ puromicin resistant 4T1 cells to the tail vein. All mice were sacrificed on day 10, lungs flushed with PBS and dissociated with Collagenase A (Roche). The single cell suspension was then plated onto puromicin containing media and selected for 14 day. Colonies were stained with Methylene-Blue and counted manually.

Neutrophil purification: Whole blood was collected by cardiac puncture using heparinized (Sigma) syringe. The blood was diluted with 5 volumes of PBS containing 0.5% BSA and subjected to a discontinuous Histopaque (Sigma) gradient (1.077 and 1.119). Neutrophils were collected from the 1.077-1.119 interface, lymphocytes and monocytes collected from the plasma-1.077 interface. RBCs were eliminated by hypotonic lysis. The cells were washed twice with PBS-BSA and re-suspended in OptiMEM (Invitrogen) 0.5% FBS in a final concentration of 2×10⁶ cells/ml. Neutrophil purity and viability were determined visually and were consistently >98%.

In vitro killing assay: Luciferase labeled cells (5,000/well) were plated on a 96-well, flat bottom white polystyrene tissue culture plate in OptiMEM 0.5% FBS. 4 hours later, purified neutrophils (100,000/well) were added to the plated turnout cells and co-cultured overnight. Chemokines (20 ng/ml) or inhibitors (Apocynin (100 µM), Catalase (1,000 u/ml), Superoxide Dismutase (1,000 u/ml) and Taurine (50 mM) all from Sigma were added to the culture immediately after neutrophils were added. Following overnight incubation, the wells were washed once with PBS, the cells were lysed and luciferase activity was measured using the Clarity (Bio-Tek/microplate luminescence reader.

In vivo administration of Apocynin: Mice were orthotopically injected with 5×10⁶ luciferase labelled 4T1 cells. 24 hours later Apocynin (2.4 g/liter) was administered in sugar sweetened drinking water. Control animals were treated with sugar sweetened water. Drinking water for both Apocynin treated and control mice were replaced every two days.

Time-lapse microscopy: 20,000 4T1 cells were labelled with CellTracker-Red (molecular Probes) according to the manufacturer instructions and plated on a chamber slide. 4 hours later, 400,000 neutrophils, isolated from 4T1 tumour-bearing Balb/C Ubc-GFP mice, were added to the culture. Images were taken every 10 minutes using the MetaMorph imaging system.

Neutrophil transfer: Female nude mice were injected with 5×10⁴ luciferase labelled 4T1 cells to the tail vein. 4 hours later, the mice were injected with 5×10⁶ TENs into the tail vein. Control mice were injected with vehicle. Formation of lung metastases was monitored using the IVIS-200 optical in vivo imaging system.

Chemokine administration: rhG-CSF (Neupogen, Amgen) was administered daily (250 µg/kg/day) s.c. (subcutaneous) for 4 consecutive days.

In vitro neutrophil stimulation—neutrophils were isolated from naive nude mice and co-cultured with tumour cells in the presence of CCL2, CCL5 or rhG-CSF (20 ng/ml). Statistical analysis: For statistical analysis, the data is presented as mean+/−SEM and were analyses using Students t tests. Differences were considered significant when p<0.05.

Example II

This example demonstrates changes in gene expression at premetastatic locations.

The 4T1 routine mammary tumor model was employed to gain insight into the early transcriptional changes that take place in the pre-metastatic niche. Orthotopically implanted 4T1 tumors spontaneously metastasize primarily to the lung whereas metastases to the liver, brain, and bones are less frequent and arise much later (FIG. 1A). mRNA microarray analysis of lung and liver samples from tumor-bearing versus sham-operated mice shows no significant differences in gene expression 3 days after turnout engraftment. In contrast, 325 and 912 genes were significantly misregulated in the lung and liver (respectively) of turnout-bearing mice 7 days after tumor engraftment (FIG. 1B). Of the 325 lung misregulated genes, 293 were lung specific and were not misregulated in the liver. Merely a small number of tumor cells were found in the lungs at this point suggesting that tumor-cell contribution to the expression array is negligible (FIG. 1C).

Of the acutely upregulated genes that came up in the expression array (FIG. 1D), MMP9 was of high interest given that this protein is involved in tissue remodeling and metastasis-associated degradation of the extra cellular matrix (Hiratsuka, et. al., Cancer Cell 2:289-300 (2002), Itoh, et. al., Clin Exp Metastasis 17:177-181 (1999), herein incorporated by reference).

Example III

This example shows exemplary MMP9+ cells present in the pre-metastatic lung. MMP9+ cells have neutrophil markers.

A dramatic increase in cells staining positive for MMP9 were seen in the pre-metastatic lung but not in the liver (FIG. 2A). The increase in MMP9 staining was not unique to the pre-metastatic lungs of 4T1 tumour bearing mice but was also found in mice bearing other pre-metastatic xenografts and in spontaneous tumor models (FIG. 6). Interestingly, there was no increase in MMP9 staining in mice with orthotopic MCF7 tumours, which fail to colonize the lung.

The inventors contemplated that MMP9+ cells present in the pre-metastatic lung might be neutrophils as several neutrophil-specific genes (such as cathelicidin and lactoferrin) are acutely upregulated in the pre-metastatic expression array (FIG. 1D). Immunohistological analysis performed on pre-metastatic lung tissue shows that the MMP9+ cells in the lungs co-stain with the neutrophil marker Ly-6G (FIG. 2B) but not with the pan macrophage marker F4/801 Further analyses show that MMP9+ cells in the pre metastatic lung co-stain with other neutrophil markers such are myeloperoxidase and Cathelicidin. Lung tissue taken from human breast cancer patients with lung metastases show high levels of myeloperoxidase staining (in 5/5 case examined) which indicated that neutrophil recruitment to the lungs is also relevant in human breast cancer (FIG. 6C).

Example IV

This example shows exemplary Gr-1 depletion associated with an exemplary increase in tumor-cell colonization of the lungs.

Mice were orthotopically injected with 4T1 cells to generate a primary tumour and were then treated with either control (IgG) or a neutrophil depleting antibody (Gr-1) starting on day 3 post tumour engraftment (FIG. 2C). Control mice were sham-operated (no tumour) and treated with the control antibody (IgG). Each mouse was challenged with i.v. injection of puromicin-resistant 4T1 cells 7 days after primary tumour engraftment (FIG. 2C). The mice were sacrificed 3 days later (day 10) and the number of colony-forming puromicin-resistant tumour cells in the lungs was determined (FIG. 2C). Tumour-bearing mice treated with the Gr-1 antibody show significant reduction of neutrophil numbers in the circulation, lungs and the primary tumour-rim (FIG. 2D-E).

The 2-fold increase in tumour-cell seeding in the lungs of tumour bearing compared to sham-operated mice, is consistent with previous studies (Hiratsuka, et. al., Cancer Cell 2:289-300 (2002), herein incorporated by reference) and suggested that the metastatic efficiency is enhanced in the presence of a primary tumour (FIG. 2F). Assuming that priming of the lungs for the arrival of tumour cells from the circulation is mediated by TENs, neutrophil depletion should have reduced the seeding efficiency in the lungs. However, The inventors observed a 2-fold and a 4-fold increase in seeding efficiency compared to tumour bearing mice treated with a control antibody and sham-operated mice respectively, suggesting that TENs attenuate the seeding of tumour cells in the lungs. Interestingly, neutrophil depletion did not affect the growth of the primary tumour (FIG. 2G).

Example V

This example shows exemplary shows exemplary depletion of Gr-1+ cells in tumor bearing mice.

The inventors next tested the long-term effects of neutrophil depletion on spontaneous metastasis from the mammary fat pad. Neutrophil depletion in the circulation was highly effective until day 16 post tumour engraftment after which neutrophil levels were not significantly different in IgG treated or Gr-1 treated mice (FIG. 3B). While neutrophil-depletion had no effect on the growth rate of the primary tumour (FIG. 3C), neutrophil-depleted tumour-bearing mice developed lung metastases earlier than control mice. Moreover, the lung metastases in neutrophil-depleted mice also grew significantly faster than in control mice (FIGS. 3A and 3D).

The inventors sought to determine whether TENs are sufficient for providing anti-metastatic protection. To this end, mice were injected with 4T1 cells via the tail vein and then challenged with neutrophils purified from 4T1 tumour-bearing mice or sham operated control animals. The transfer of TENs results in a dramatic delay in the formation of lung metastases (FIG. 3 E-G). These observations suggest that TENs can provide anti-metastatic protection in vivo. The inventors therefore propose that TENs are sufficient for clearance of lung arrested cancer cells and thus confer anti-metastatic protection.

Example VI

This example shows exemplary TENS of the present inventions.

Since neutrophils are armed with an arsenal of toxic peptides and molecules the inventors postulated that TENs may be able to kill tumour cells directly and thereby provide anti-metastatic protection. The inventors therefore tested the tumour-cell killing capacity of TENs in vitro. Neutrophils were purified from sham-operated and tumour-bearing mice and added to a culture of 4T1 cells that were labeled with luciferase to allow selective quantification within the co-culture. While control neutrophils, purified from sham-operated mice had no significant cytotoxic effect, TENs were highly cytotoxic (FIG. 4A). Such cytotoxicity was not observed when tumour cells were co-cultured with a mixture of lymphocytes and monocytes purified from either tumour bearing or control mice. No killing was observed when the neutrophils and the tumour cells were co-cultured separated by a membrane implying that physical contact is necessary for neutrophil mediated tumour-cell killing (FIG. 4B). A similar killing pattern was observed with MCF7 cells co-cultured with TENs from 4T1-tumour bearing mice. Furthermore, neutrophils purified from C57/26 mice engrafted with B16 melanoma tumours gained the ability to kill 4T1 cells while purified neutrophils from naive C57/B6 mice could not (FIG. 4C). These results suggest that there is a general mechanism by which TENs gain the capacity to kill tumour cells and thereby inhibit metastasis. The inventors were also able to monitor the interaction between TENs and tumour cells using time-lapse microscopy. As early as 60 minutes after their addition, GFP labeled TENs can be seen converging on the adherent 4T1 cells (red). The neutrophils initiate physical contact with the tumour cell at which time the tumour cell undergoes nuclear blebbing, a morphological change tightly associated with apoptosis. Finally, the neutrophils disengage, leaving behind the fragmented tumour cell (FIG. 4E).

Next the inventors sought to characterize the mechanism by which neutrophils kill tumour cells. Neutrophils can generate reactive oxygen species (ROS) through the activity of the NADPH Oxidase complex and induce cell death by an oxidative burst (FIG. 4G). Indeed, co-culture of TENs with tumour cells in the presence: of Apocynin, a: specific inhibitor of the NADPH Oxidase complex, completely inhibits the neutrophil mediated tumour-cell killing (FIG. 4H). The inventors then interfered with the reactions downstream from NADPH Oxidase using pharmacological inhibitors. Addition of exogenous superoxide dismutase did not inhibit cell death suggesting that superoxides per se are not directly involved in cell killing. In contrast, catalase (which converts f $H_2O_2$ to $H_2O$ and $O_2$) completely inhibits cell killing (FIG. 4H). Interestingly, the presence of the hypochlorous acid scavenger, taurine, did not reduce tumour-cell killing by stimulated neutrophils suggesting the killing is by f H$_2$O$_2$ (FIG. 4I). Finally, to test whether this process through which neutrophils inhibit metastasis is also relevant in vivo the inventors tested the effect of Apocynin on spontaneous metastasis. The inventors show that Apocynin treatment enhances metastasis and that Apocynin treated mice developed spontaneous lung metastases earlier than control mice (FIG. 4K). These results suggest that neutrophils induce tumour cell death through generation of ROS by the NAPDH Oxidase complex.

Example VII

This example shows exemplary in vivo rhG-CSF administration is sufficient for mobilization and lung sequestration of neutrophils.

A. Blood differentials of rhG-CSF and vehicle treated mice showing an increase in circulating neutrophils after 3 days of rhG-CSF administration. Ly-6G (B.) or myeloperoxidase (C,) immunohistochemistry on lung tissue shows that rhG-CSF administration induces an increase in lung-associated neutrophils.

However, it is the generation of H$_2$O$_2$ rather than superoxides or the f H$_2$O$_2$ chlorine metabolites that are responsible for the killing. What is the mechanism through which neutrophils are activated by the primary tumour? 4T1 tumour bearing mice have been shown to have high levels of serum G-CSF that may account for neutrophil mobilization (DuPre, et. al., Exp Mol Patho 182:12-24 (2007), herein incorporated by reference). Indeed, in vivo rhG-CSF administration induces a significant increase in circulating and lung-associated neutrophil numbers (FIG. 7).

Example VIII

This example demonstrates exemplary CCL2 is both required and sufficient for neutrophil entrainment in vivo.

In vivo rhG-CSF administration induced a significant increase in circulating and lung-associated neutrophil numbers (FIG. 7). However, it did not induce a cytotoxic neutrophil response in vitro (FIG. 5A). This observation indicated that although neutrophil mobilization through G-CSF may be necessary for the protective role of TENs, further activation is necessary for the entrainment of their anti-metastatic behavior.

The expression array performed on pre-metastatic lungs showed a 7.9 and 4.6 fold increase in CCR1 and CCR2 respectively, both of which are expressed in mouse neutrophils (Reichel, et. al., J Leukoc Biol 79, 114-122 (2006), herein incorporated by reference) (and FIG. 8).

Since 4T1 tumours were shown to secrete CCL2 and CCL5 (DuPre, et. al., Int J Exp Patho 188, 351-360 (2007), herein incorporated by reference) that are potential ligands for CCR2 and CCR1 respectively, the inventors tested whether these chemokines can induce neutrophil-mediated tumour-cell killing. The inventors found that addition of either CCL2 or CCL5 can stimulate naive neutrophils and induce tumour cell killing in vitro implying that both are sufficient for neutrophil entrainment (FIG. 5A). However, while CCL5 knockdown of orthotopically injected 4T1 tumours retained their ability to entrain neutrophils, in vivo CCL2 knockdown turnouts did not, suggesting that unlike CCL5, CCL2 is both required and sufficient for neutrophil entrainment in vivo (FIGS. 5B and 5C). Several studies have shown that CCL2 has a pro tumorigenic effect and that high CCL2 serum levels in Ganser patients are associated with advanced disease (Loberg, et. al., Cancer Res. 67:9417-9424 (2007), Lu, et. al., J Biol Chem 284:29087-29096 (2009), Soria, et. al., Cancer Lett 267:271-285 (2008), each of which is herein incorporated by reference) while others propose that CCL2 has an anti-metastatic role and that high CCL2 serum levels negatively correlate with cancer progression (Dehqanzada, et. al., Clin Cancer Res 12:478-486 (2006), Huang, et. al., Cancer Immunol Immunother 39:231-238 (1994), Takahashi, et. al., Clin Exp Metastasis (2009), Tonouchi, et. al., Scand J Gastroentero 137:830-833 (2002), each of which is herein incorporated by reference).

To gain insight into the role of tumour secreted CCL2 on tumour growth and metastasis in vivo, the inventors compared the growth and spontaneous metastasis of orthotopically implanted CCL2 knockdown (CCL2kd) and control 4T1 tumours. Consistent with the pro tumourigenic properties attributed to CCL2 the inventors found that primary CCL2kd tumours show growth retardation when compared to control tumours (FIG. 5D). However, The inventors found that spontaneous metastasis from the CCL2kd tumours occurs earlier (FIG. 5E) suggesting that these tumours have increased metastatic potential. Taken together, these observations suggest that while CCL2 secretion by the primary tumour has a beneficial effect and enhances growth at the primary site, it is concomitantly capable of inducing an anti-metastatic neutrophil response and inhibiting tumour cell seeding at a distant site.

Example IX

This is an exemplary demonstration of increasing cytotoxicity of naïve neutrophils for killing cancer cells.

Naïve human neutrophils were isolated from human subject who were believed to not have cancer. Naïve human neutrophils were co-cultured with MDA-MB-231 cells, a human breast cancer cell line. While naïve neutrophils do not kill MDA-DB-231 cells the addition of different CC and CXC human chemokines induces neutrophil mediated cell killing. CCL2, CCL3 and CCL5 but not CCL4 significantly increase neutrophil cytotoxicity. Similarly, SDF1 (CXCL12), CXCL16 and to a lesser extent CXCL1 significantly increase neutrophil cytotoxicity.

Example X

This is an exemplary description for optimizing a protocol for in vitro anti-metastatic entrainment of neutrophils.

The inventors contemplate a need for increasing the number of entrained neutrophils for use in treatment methods of the present inventions. Preliminary data described herein obtained during the development of the present inventions indicates that TENs have anti-metastatic properties while nave neutrophils do not. Therefore a protocol for efficient collection and In vitro entrainment of neutrophils for optimization of number of entrained neutrophils is provided herein.

Thus in one embodiment, the inventors contemplate a method of pre isolation, pre-entrainment, in vivo neutrophil expansion comprising at least one agent. In one preferred embodiment, the agent is granulocyte colony-stimulating factor, G-CSF. Granulocyte colony-stimulating factor, G-CSF, induces neutrophil proliferation and maturation and increases neutrophil levels in the circulation. It is widely used to treat patients in cases of neutropenia.

However, the inventors found that although G-CSF can mobilize neutrophils, it was not shown to induce an anti-metastatic response of the present inventions. Therefore further activation of neutrophils is contemplated. In one contemplated embodiment, G-CSF will be used in vivo to increase neutrophil numbers prior to purification from the circulation. After isolation these in vivo expanded neutrophil populations will be entrained and tested for induction of the anti-metastatic response in vitro.

As shown herein, neutrophil entrainment was achieved using CCL2 and/or CCL5 in vitro with evidence of enhancement by an agent for inducing TGF-β signaling blockade. In one embodiment for developing an exemplary method, a mouse model, such as Balb/C mice, will be treated with G-CSF in order to increase (i.e. mobilize) neutrophils in circulation contemplated to enhance neutrophil numbers in the circulation. Daily administration of 250 ug/kg/day s.c. for 4 consecutive days increased circulating neutrophil numbers in mice by 2-4 fold. In one embodiment, a known agent that may be used to enhance human neutrophil numbers in human circulation is Filgrastim/NEUPOGEN®, i.e. G-CFS, see, prescribing information from AMGEN.

Neutrophils will be purified from the donor mice and treated with CCL2, CCL5 or a combination of both in the presence or absence of TGF-β blockers (such as SB 431542, Tocris Biosciences) to induce an anti-metastatic response. The stimulated neutrophils will be introduced, via the tail-vein, to recipient Balb/C mice previously injected with luciferase labeled tumor cells. Control mice of matching genotypes will also be injected with G-CSF primed, uninduced neutrophils and luciferase labeled tumor cells. The readout for this experiment will be the formation of metastatic lesions in the lung as monitored by luciferase imaging and histology.

Example XII

This is an exemplary description for assessing the benefits of supplementing conventional chemotherapy with TENs therapy.

The inventors contemplate a preclinical mouse Luciferase-labeled 4T1 breast cancer model in syngeneic Balb/C female mice. Orthotopically (mammary fat pad) injected 4T1 tumors are highly metastatic and primarily form metastases in the lungs. Using this model actual treatment of breast cancer patients by resecting the primary tumor and administering chemotherapy (Paclitaxel) will be simulated in mice. To assess the benefits of entrained neutrophil therapy on metastatic progression-neutrophils from tumor bearing Balb/C donor mice will be transfused at different time points; post operative, during chemotherapy and once chemotherapy cycles have ended. Metastatic progression will then be followed as described herein. Using the same experimental design TGF-b blockade prior to TENs transfusion will be tested to find out whether it can further potentiate neutrophil anti metastatic activity. In addition, neutrophils mobilized by GCSF treatment, purified and treated with CCL2 and CCL5 (alone and in combination) in the presence or absence of TGF-beta blockers will be tested in the same assays. Once an effective neutrophil therapy protocol has been established in mice, the safety of the procedure in another species (canine or swine) will be established. This will serve as the basis for a phase I clinical trial on human cancer patients.

We claim:
1. A method, comprising,
  a) providing,
    i) a patient at risk for developing metastatic cancer, wherein said patient comprises a neutrophil, wherein said neutrophil is capable of being cytotoxic to a tumor cell; and
    ii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing said neutrophil cytotoxicity;
  b) isolating said neutrophil from said patient; and
  c) contacting said neutrophil with said chemokine under conditions for increasing cytotoxic activity of said neutrophil.
2. The method of claim 1, wherein said contacting further comprises contacting with a transforming growth factor-beta inhibitor.
3. The method of claim 1, further comprising a test tumor cell, wherein said neutrophil has increased cytotoxicity towards said test tumor cell after said contacting.
4. The method of claim 1, wherein said increasing cytotoxicity is increasing cytotoxicity for mediating killing of a tumor cell.
5. The method of claim 1, wherein said increasing cytotoxicity is increasing capability to induce apoptosis in a tumor cell.
6. The method of claim 1, wherein said increasing cytotoxicity is increasing oxidative activity of said neutrophil for providing an oxidative burst capable of killing a tumor cell.
7. The method of claim 1, wherein said patient is administered granulocyte colony-stimulating factor prior to said isolation of said neutrophil.
8. The method of claim 1, wherein said neutrophil comprises a matrix metallopeptidase 9 marker.
9. A method, comprising,
  a) providing,
    i) a patient comprising at least one tumor cell capable of metastasis, wherein said patient further comprises a neutrophil, wherein said neutrophil is capable of being cytotoxic to said tumor cell;
    ii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing cytotoxicity of said neutrophil;
  b) isolating said neutrophil from said patient;
  c) contacting said neutrophil with said chemokine under conditions for increasing cytotoxic activity of said neutrophil; and
  d) administering said contacted neutrophil to said patient under conditions such that said tumor cell is inhibited from metastasis.
10. The method of claim 9, wherein said contacting further comprises contacting with a transforming growth factor-beta inhibitor.
11. The method of claim 9, wherein said tumor cell is selected from the group consisting of breast cancer, colon cancer, prostate cancer and lung cancer.
12. The method of claim 9, wherein said neutrophil comprises a matrix metallopeptidase 9 marker.
13. The method of claim 9, wherein said increasing cytotoxicity is increasing cytotoxicity for mediating killing of a tumor cell.
14. The method of claim 9, wherein said increasing cytotoxicity is increasing capability to induce apoptosis in a tumor cell.
15. The method of claim 9, wherein said increasing cytotoxicity is increasing oxidative activity of said neutrophil for providing an oxidative burst capable of killing a tumor cell.

16. The method of claim 9, wherein said method further comprises administering a granulocyte colony-stimulating factor to said patient prior to said isolation of said neutrophil.

17. The method of claim 9, wherein said administering of said neutrophil is prior to detection of said tumor cell metastasis.

18. The method of claim 9, wherein said administering of said neutrophil is after detection of said metastasis.

19. A method, comprising,
   a) providing,
      i) a pharmaceutical composition, comprising an agent for increasing the number of neutrophils in a blood sample;
      ii) a patient comprising a tumor cell and circulating neutrophils;
      iii) a chemokine selected from the group consisting of Chemokine (C-C motif) ligand 2, Chemokine (C-C motif) ligand 3, Chemokine (C-C motif) ligand 5, chemokine (C-X-C motif) ligand 1, chemokine (C-X-C motif) ligand 12, chemokine (C-X-C motif) ligand 16, capable of increasing cytotoxicity of a neutrophil;
   b) administering said pharmaceutical composition under conditions such that said circulating neutrophils are increased in a blood sample of said patient;
   c) isolating said neutrophils from a blood sample of said patient;
   d) contacting said neutrophils with said chemokine under conditions for increasing cytotoxic activity of said neutrophil; and
   e) administering said contacted neutrophils to said patient under conditions such that said tumor cell is inhibited from metastasis.

20. The method of claim 19, wherein said agent is granulocyte colony-stimulating factor.

* * * * *

UNITED STATES PATENT AND TRADEMARK OFFICE
CERTIFICATE OF CORRECTION

PATENT NO.        : 9,199,028 B2                                    Page 1 of 1
APPLICATION NO.   : 13/521982
DATED             : December 1, 2015
INVENTOR(S)       : Robert Benezra It is certified that error appears in the above-identified patent and that said Letters Patent is hereby corrected as shown below:

Specification

In column 1, at line 20, please insert:

-- This invention was made with government support under grant number CA094060 awarded by National Institutes of Health. The government has certain rights in the invention. --

Signed and Sealed this
Seventeenth Day of May, 2016

Michelle K. Lee
*Director of the United States Patent and Trademark Office*